United States Patent
Lockwood et al.

(10) Patent No.: US 7,022,113 B2
(45) Date of Patent: Apr. 4, 2006

(54) CONTROL OF VACUUM LEVEL RATE OF CHANGE

(75) Inventors: Jeffrey S. Lockwood, Batesville, IN (US); Robert Petrosenko, Charleston, SC (US); James Robert Risk, Jr., Fountaintown, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 135 days.

(21) Appl. No.: 10/192,894

(22) Filed: Jul. 11, 2002

(65) Prior Publication Data

US 2003/0014022 A1    Jan. 16, 2003

Related U.S. Application Data

(60) Provisional application No. 60/304,990, filed on Jul. 12, 2001.

(51) Int. Cl.
  *A61M 27/00* (2006.01)
  *A61M 1/00* (2006.01)
  *A61H 7/00* (2006.01)

(52) U.S. Cl. ...................... 604/313; 604/543; 604/320; 604/327; 601/6

(58) Field of Classification Search ................ 604/289, 604/304, 313, 315–319, 327, 543, 320, 355, 604/356; 601/6–14; 602/41; 417/43, 44.2
See application file for complete search history.

(56) References Cited

U.S. PATENT DOCUMENTS

| | | | |
|---|---|---|---|
| 774,529 A | 11/1904 | Nieschang | |
| 1,000,001 A | 8/1911 | Holz | |
| 1,355,846 A | 10/1920 | Rannells | |
| 1,385,346 A | 7/1921 | Taylor | |
| 1,936,129 A | 11/1933 | Fisk | |
| 2,195,771 A | 4/1940 | Estler | |
| 2,221,758 A | 11/1940 | Elmquist | |
| 2,338,339 A | 1/1944 | La Mere et al. | |
| 2,443,481 A | 6/1948 | Sene | |
| 2,573,791 A | 6/1951 | Howells | |
| 2,577,945 A | 12/1951 | Atherton | |
| 2,632,443 A | 3/1953 | Lesher | |

(Continued)

FOREIGN PATENT DOCUMENTS

DE    372727    3/1923

(Continued)

OTHER PUBLICATIONS

Davydov, et al., Vestn. Khir., Sep. 1988, "Vacuum Therapy in the Treatment of Acute Suppurative Diseases of Soft Tissues and Suppurative Wounds" (English translation by R. McElroy Translation Co, Austin, Texas).

(Continued)

*Primary Examiner*—Tatyana Zalukaeva
*Assistant Examiner*—Michael G. Bogart
(74) *Attorney, Agent, or Firm*—Barnes & Thornburg LLP

(57) ABSTRACT

A wound treatment apparatus has a vacuum bandage covering a wound of a patient, a vacuum source coupled to the vacuum bandage, and a controller that operates the vacuum source to apply negative pressure to the wound through the bandage in a controlled manner. The controller is programmed to limit the rate of change of the negative pressure applied to the wound. A caregiver has the ability to change one or more negative pressure setpoint values and the controller of the wound treatment apparatus controls the rate of change of the negative pressure to reduce patient discomfort.

20 Claims, 49 Drawing Sheets

U.S. PATENT DOCUMENTS

| | | | |
|---|---|---|---|
| 2,682,873 | A | 7/1954 | Evans et al. |
| 3,026,874 | A | 3/1962 | Stevens |
| 3,315,665 | A | 4/1967 | MacLeod |
| 3,367,332 | A | 2/1968 | Groves |
| 3,382,867 | A | 5/1968 | Reaves |
| 3,520,300 | A | 7/1970 | Flower, Jr. |
| 3,528,416 | A | 9/1970 | Chamberlain |
| 3,610,238 | A | 10/1971 | Rich, Jr. |
| 3,648,692 | A | 3/1972 | Wheeler |
| 3,782,377 | A | 1/1974 | Rychlik |
| 3,812,972 | A | 5/1974 | Rosenblum |
| 3,814,095 | A | 6/1974 | Lubens |
| 3,874,387 | A | 4/1975 | Barbieri |
| 3,903,882 | A | 9/1975 | Augurt |
| 3,935,863 | A | 2/1976 | Kilger |
| 3,954,105 | A | 5/1976 | Nordby et al. |
| RE29,319 | E | 7/1977 | Nordby et al. |
| 4,080,970 | A | 3/1978 | Miller |
| 4,112,947 | A | 9/1978 | Nehring |
| 4,139,004 | A | 2/1979 | Gonzalez, Jr. |
| 4,149,541 | A | 4/1979 | Gammons et al. |
| 4,191,204 | A * | 3/1980 | Nehring ................ 137/205 |
| 4,224,941 | A | 9/1980 | Stivala |
| 4,250,882 | A | 2/1981 | Adair |
| 4,275,721 | A | 6/1981 | Olson |
| 4,297,995 | A | 11/1981 | Golub |
| 4,341,209 | A | 7/1982 | Schaar |
| 4,373,519 | A | 2/1983 | Errede et al. |
| 4,382,441 | A | 5/1983 | Svedman |
| 4,399,816 | A | 8/1983 | Spangler |
| 4,457,755 | A | 7/1984 | Wilson |
| 4,465,062 | A | 8/1984 | Versaggi et al. |
| 4,469,092 | A | 9/1984 | Marshall et al. |
| 4,525,166 | A | 6/1985 | Leclerc |
| 4,533,352 | A | 8/1985 | Van Beek et al. |
| 4,540,412 | A | 9/1985 | Van Overloop |
| 4,553,967 | A | 11/1985 | Ferguson et al. |
| 4,569,674 | A | 2/1986 | Phillips et al. |
| 4,573,965 | A | 3/1986 | Russo |
| 4,579,555 | A | 4/1986 | Russo |
| 4,605,399 | A | 8/1986 | Weston et al. |
| 4,608,041 | A | 8/1986 | Nielsen |
| 4,624,656 | A | 11/1986 | Clark et al. |
| 4,633,863 | A | 1/1987 | Filips et al. |
| 4,637,819 | A | 1/1987 | Ouellette et al. |
| 4,641,643 | A | 2/1987 | Greer |
| 4,655,754 | A | 4/1987 | Richmond et al. |
| 4,661,093 | A | 4/1987 | Beck et al. |
| 4,664,652 | A | 5/1987 | Weilbacher |
| 4,667,666 | A | 5/1987 | Fryslie |
| 4,679,590 | A | 7/1987 | Hergenroeder |
| 4,717,382 | A | 1/1988 | Clemens et al. |
| 4,733,659 | A | 3/1988 | Edenbaum et al. |
| 4,743,232 | A | 5/1988 | Kruger |
| 4,747,166 | A | 5/1988 | Kuntz |
| 4,759,354 | A | 7/1988 | Quarfoot |
| 4,765,316 | A | 8/1988 | Marshall |
| 4,778,446 | A | 10/1988 | Jensen |
| 4,778,456 | A | 10/1988 | Lokken |
| 4,820,265 | A | 4/1989 | DeSatnick et al. |
| 4,820,284 | A | 4/1989 | Hauri |
| 4,834,110 | A | 5/1989 | Richard |
| 4,872,450 | A | 10/1989 | Austad |
| 4,890,608 | A | 1/1990 | Steer |
| 4,897,081 | A | 1/1990 | Poirier et al. |
| 4,906,240 | A | 3/1990 | Reed et al. |
| 4,917,112 | A | 4/1990 | Kalt |
| 4,921,492 | A | 5/1990 | Schultz et al. |
| 4,941,882 | A | 7/1990 | Ward et al. |
| 4,953,565 | A | 9/1990 | Tachibana et al. |
| 4,969,880 | A | 11/1990 | Zamierowski |
| 4,969,881 | A | 11/1990 | Viesturs |
| 4,988,336 | A | 1/1991 | Kohn |
| 4,990,144 | A | 2/1991 | Blott |
| 4,991,574 | A | 2/1991 | Pocknell |
| 4,997,425 | A | 3/1991 | Shioya et al. |
| 5,002,528 | A | 3/1991 | Palestrant |
| 5,002,529 | A | 3/1991 | Cunningham |
| 5,003,971 | A | 4/1991 | Buckley |
| 5,014,389 | A | 5/1991 | Ogilvie et al. |
| 5,034,003 | A | 7/1991 | Denance |
| 5,034,006 | A | 7/1991 | Hosoda et al. |
| 5,042,978 | A | 8/1991 | Quenin et al. |
| 5,060,662 | A | 10/1991 | Farnswoth, III |
| 5,073,172 | A | 12/1991 | Fell |
| 5,086,763 | A | 2/1992 | Hathman |
| 5,086,764 | A | 2/1992 | Gilman |
| 5,100,396 | A | 3/1992 | Zamierowski |
| 5,101,808 | A * | 4/1992 | Kobayashi et al. ........... 601/44 |
| 5,106,362 | A | 4/1992 | Gilman |
| 5,106,629 | A | 4/1992 | Cartmell et al. |
| 5,135,518 | A | 8/1992 | Vera |
| 5,147,338 | A | 9/1992 | Lang et al. |
| 5,149,331 | A | 9/1992 | Ferdman et al. |
| 5,152,757 | A | 10/1992 | Eriksson |
| 5,160,322 | A | 11/1992 | Scheremet et al. |
| 5,167,613 | A | 12/1992 | Karami et al. |
| 5,170,781 | A | 12/1992 | Loomis |
| 5,176,663 | A | 1/1993 | Svedman et al. |
| 5,176,667 | A | 1/1993 | DeBring |
| 5,215,539 | A | 6/1993 | Schoolman |
| 5,228,431 | A | 7/1993 | Giarretto |
| 5,230,350 | A | 7/1993 | Fentress |
| 5,261,893 | A | 11/1993 | Zamierowski |
| 5,263,922 | A | 11/1993 | Sova et al. |
| 5,298,015 | A | 3/1994 | Komatsuzaki et al. |
| 5,330,452 | A | 7/1994 | Zook |
| 5,344,415 | A | 9/1994 | DeBusk et al. |
| 5,349,965 | A | 9/1994 | McCarver |
| 5,358,494 | A | 10/1994 | Svedman |
| 5,376,252 | A | 12/1994 | Ekstrom et al. |
| 5,395,315 | A | 3/1995 | Griep |
| 5,419,768 | A * | 5/1995 | Kayser ................ 604/119 |
| 5,431,662 | A | 7/1995 | Nicholas |
| 5,437,651 | A | 8/1995 | Todd et al. |
| 5,445,604 | A | 8/1995 | Lang |
| 5,451,215 | A | 9/1995 | Wolter |
| 5,478,333 | A | 12/1995 | Asherman, Jr. |
| 5,484,427 | A | 1/1996 | Gibbons |
| 5,487,889 | A | 1/1996 | Eckert et al. |
| 5,520,652 | A * | 5/1996 | Peterson ................ 604/119 |
| 5,527,293 | A | 6/1996 | Zamierowski |
| 5,531,670 | A | 7/1996 | Westby et al. |
| 5,542,918 | A | 8/1996 | Atkinson |
| 5,549,584 | A | 8/1996 | Gross |
| 5,556,375 | A | 9/1996 | Ewall |
| 5,578,022 | A | 11/1996 | Scherson et al. |
| 5,607,388 | A | 3/1997 | Ewall |
| 5,628,735 | A | 5/1997 | Skow |
| 5,636,643 | A | 6/1997 | Argenta et al. |
| 5,645,081 | A | 7/1997 | Argenta et al. |
| 5,655,258 | A | 8/1997 | Heintz |
| 5,656,027 | A | 8/1997 | Ellingboe |
| 5,662,598 | A | 9/1997 | Tobin |
| 5,662,624 | A | 9/1997 | Sundstrom et al. |
| 5,662,625 | A | 9/1997 | Westwood |
| 5,678,564 | A | 10/1997 | Lawrence et al. |
| 5,697,920 | A | 12/1997 | Gibbons |
| 5,735,833 | A | 4/1998 | Olson |
| 5,762,640 | A | 6/1998 | Kajiwara et al. |
| 5,782,871 | A | 7/1998 | Fujiwara et al. |
| 5,817,145 | A | 10/1998 | Augustine et al. |
| 5,827,246 | A * | 10/1998 | Bowen ................ 604/313 |
| 5,911,222 | A | 6/1999 | Lawrence et al. |

| | | | | | | |
|---|---|---|---|---|---|---|
| 5,919,476 | A | 7/1999 | Fischer et al. | GB | 1549756 | 8/1979 |
| 5,921,972 | A | 7/1999 | Skow | GB | 2329127 A | 3/1999 |
| 5,928,174 | A | 7/1999 | Gibbins | GB | 2333965 A | 8/1999 |
| 5,941,859 | A | 8/1999 | Lerman | GB | 2336546 A | 10/1999 |
| 5,947,914 | A | 9/1999 | Augustine | GB | 2342584 A | 4/2000 |
| 5,954,680 | A | 9/1999 | Augustine | GB | 2344531 A | 6/2000 |
| 5,961,480 | A | 10/1999 | Augustine | GB | 2351025 A | 12/2000 |
| 5,964,721 | A | 10/1999 | Augustine | SE | 84485 | 10/1935 |
| 5,964,723 | A | 10/1999 | Augustine | SU | 587941 | 1/1978 |
| 5,986,163 | A | 11/1999 | Augustine | SU | 1268175 A1 | 11/1986 |
| 6,010,527 | A | 1/2000 | Augustine et al. | WO | WO 89/04158 | 5/1989 |
| 6,045,518 | A | 4/2000 | Augustine | WO | WO 90/11795 | 10/1990 |
| 6,045,541 | A | 4/2000 | Matsumoto et al. | WO | WO 91/00718 | 1/1991 |
| 6,071,254 | A | 6/2000 | Augustine | WO | WO 91/16030 | 10/1991 |
| 6,071,267 | A | 6/2000 | Zamierowski | WO | WO 92/19313 | 11/1992 |
| 6,071,304 | A | 6/2000 | Augustine et al. | WO | WO 92/20299 | 11/1992 |
| 6,080,189 | A | 6/2000 | Augustine et al. | WO | WO 93/09727 | 5/1993 |
| 6,080,243 | A | 6/2000 | Insley et al. | WO | WO 94/0009 | 1/1994 |
| 6,093,160 | A | 7/2000 | Augustine et al. | WO | WO 94/20041 | 9/1994 |
| 6,095,992 | A | 8/2000 | Augustine | WO | WO 96/05873 | 2/1996 |
| 6,110,197 | A | 8/2000 | Augustine et al. | WO | WO 96/15745 | 5/1996 |
| 6,113,561 | A | 9/2000 | Augustine | WO | WO 99/13793 | 3/1999 |
| 6,117,111 | A | 9/2000 | Fleischmann | WO | WO 00/07653 | 2/2000 |
| 6,135,116 | A | 10/2000 | Vogel et al. | WO | WO 00/15277 | 3/2000 |
| 6,142,982 | A | 11/2000 | Hunt et al. | WO | WO 00/21586 * | 4/2000 |
| 6,143,945 | A | 11/2000 | Augustine et al. | WO | WO 00/26100 | 5/2000 |
| 6,174,306 | B1 | 1/2001 | Fleischmann | WO | WO 00/30567 | 6/2000 |
| 6,203,563 | B1 | 3/2001 | Fernandez | WO | WO 00/32247 | 6/2000 |
| 6,207,875 | B1 | 3/2001 | Lindqvist et al. | WO | WO 00/38755 | 6/2000 |
| 6,213,965 | B1 | 4/2001 | Augustine et al. | WO | WO 00/38552 | 7/2000 |
| 6,213,966 | B1 | 4/2001 | Augustine | WO | WO 00/59418 | 10/2000 |
| 6,217,535 | B1 | 4/2001 | Augustine | WO | WO 00/59424 | 10/2000 |
| 6,235,009 | B1 | 5/2001 | Skow | WO | WO 00/61206 | 10/2000 |
| 6,235,047 | B1 | 5/2001 | Augustine et al. | WO | WO 00/64394 | 11/2000 |
| 6,241,697 | B1 | 6/2001 | Augustine | WO | WO 01/34223 A1 | 5/2001 |
| 6,241,698 | B1 | 6/2001 | Augustine | WO | WO 01/37922 A2 | 5/2001 |
| 6,248,084 | B1 | 6/2001 | Augustine et al. | WO | WO 01/49233 A1 | 7/2001 |
| 6,254,557 | B1 | 7/2001 | Augustine et al. | WO | WO 01/85248 A1 | 11/2001 |
| 6,254,580 | B1 | 7/2001 | Svedman | WO | WO 03/005943 A3 * | 1/2003 |
| 6,264,622 | B1 | 7/2001 | Augustine | | | |
| 6,264,979 | B1 | 7/2001 | Svedman | | | |
| 6,267,740 | B1 | 7/2001 | Augustine et al. | | | |
| 6,283,931 | B1 | 9/2001 | Augustine | | | |
| 6,284,941 | B1 | 9/2001 | Cox et al. | | | |
| 6,290,685 | B1 | 9/2001 | Insley et al. | | | |
| 6,293,917 | B1 | 9/2001 | Augustine et al. | | | |
| 6,345,623 | B1 | 2/2002 | Heaton et al. | | | |
| 6,663,349 | B1 * | 12/2003 | Discenzo et al. .......... 417/44.1 | | | |
| 6,685,681 | B1 * | 2/2004 | Lockwood et al. ......... 604/305 | | | |
| 6,749,592 | B1 * | 6/2004 | Lord .......................... 604/319 | | | |
| 2001/0029956 | A1 | 10/2001 | Argenta et al. | | | |

FOREIGN PATENT DOCUMENTS

| | | |
|---|---|---|
| DE | 2809828 | 9/1978 |
| DE | 3102674 A1 | 9/1982 |
| DE | 3539533 A1 | 5/1987 |
| DE | 4111122 A1 | 4/1993 |
| DE | 29504378 U1 | 10/1995 |
| DE | 19722075 C1 | 10/1998 |
| DK | 64055 | 10/1945 |
| EP | 01117632 | 9/1984 |
| EP | 0424165 A1 | 4/1991 |
| EP | 0485657 A1 | 5/1992 |
| EP | 0547496 A1 | 12/1992 |
| EP | 0777504 B1 | 6/1997 |
| EP | 0853950 A1 | 7/1998 |
| EP | 0880953 A2 | 12/1998 |
| EP | 1 088569 A2 | 4/2001 |
| FR | 500253 | 3/1920 |
| FR | 1303238 | 7/1962 |
| GB | 3090 | 6/1902 |
| GB | 641061 | 8/1950 |

OTHER PUBLICATIONS

Davydov, et al., Khirugiia, Jun. 1990, "Pathenogenic Mechanism of the Effect of Vacuum Therapy on the Course of the Wound Process" (English translation by R. McElroy Translation Co., Austin, Texas).

Davydov, et al., Vestn. Khir., Nov. 1986, "Vacuum Therapy in the Treatment of Suppurative Lactation Mastitis" (English translation by R. McElroy Translation Co., Austin, Texas).

Davydov, et al., Vestn, Khir., Oct. 1988, "Bacteriological and Cytological Evaluation of the Vacuum Therapy of Suppurative Wounds" (English translation by R. McElroy Translation Co., Austin, Texas).

Davydov, et al., Vestn. Khir., Mar. 1990, "Basis of the Use of Forced Early Secondary Suture in the Treatment of Suppurative Wounds by the Vacuum Therapy Method" (English translation by R. McElroy Translation Co., Austin Texas).

Mirazimov, et al., Ortop Travmatol Protez., Oct. 1966, Free Skin Graft of the Foot with Preparation of the Wound Surface by Vacuum Treatment (English translation by R. McElroy Translation Co., Austin, Texas).

Borzov, et al., Vestn. Dermatol. Venerol., Aug. 1965, "Vacuum Therapy of Some Skin Diseases" (English translation by R. McElroy Translation Co., Austin, Texas).

Jeter, et al., Chronic Wound Care; 27: pp. 240-246, "Managing Draining Wounds and Fistulae: New and Established Methods".

Mulder, et al., Wound Healing Publications 1991, "Clinicians' Pocket Guide to Chronic Wound Repair".

Valenta, AIN Apr. 1994; pp. 44-45, "Using the Vacuum Dressing Alternative for Difficult Wounds".

Wolthuis, et al., Physiological Reviews Jul. 1974; vol. 54, No. 3, pp. 566-595, "Physiological Effects of Locally Applied Reduced Pressure in Man".

Fleischmann, WundForum Spezial IHW 1994; pp. 54-55, "Vacuum Sealing for Treatment of Problematical Wounds" (English translation provided).

Bucalo, et al., Wound Repair and Regeneration; Jul.-Sep. 1993; pp. 181-186, "Inhibition of Cell Proliferation by Chronic Wound Fluid".

Olenius, et al., Plastic and Reconstructive Surgery Feb. 1993: pp. 213-215, "Mitotic Activity in Expanded Human Skin".

Viljanto, et al., Br. J. Surg. 1976; vol. 63: pp. 427-430, "Local Hyperalimentation of Open Wounds".

Dunlop, et al., Br. J. Surg. May, 1990; vol. 77: pp. 562-563, "Vacuum Drainage of Groin Wounds after Vascular Surgery: A Controlled Trial".

Comment-Dunlop et al., Apr. 1991, pp. 505-506 on "Vacuum Drainage of Groin Wounds after Vascular Surgery".

Landis, et al., Alternate Suction and Pressure, pp. 925-961—"The Effects of Alternative Suction and Pressure on Blood Flow to the Lower Extremities".

Morykwas, et al., Extracellular Matric and Healing 1993; pp. 800—"Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds".

Chariker, et al., Contemporary Surgery Jun. 1989; vol. 34: pp. 59-63—"Effective Management of Incisional and Cutaneous Fistulae with Closed Suction Wound Drainage".

Tittel, et al., Eingag und Annahme des Manuskripts Jan. 7, 1987; pp. 104-107—"New Standards in Postoperative Wound Drainage".

Genecov, et al., Annals of Plastic Surgery Mar., 1998; vol. 40, No. 3: pp. 219-225—"A Controlled Subatmospheric Pressure Dressing Increases the Rate of Skin Graft Donor Site Reepithelialization".

Morykwas, et al., Annals of Plastic Surgery Jun. 1997; vol. 38, No. 6—"Vacuum-Assisted Closure: A New Method for Wound Control and Treatment: Animal Studies and Basic Foundation".

Argenta, et al., Annals of Plastic Surgery Jun., 1997; vol. 38, No. 6:—"Vacuum-Assisted Closure: A New Method for Wound Control and Treatment: Clinical Experience".

Patent Application and Drawings—"Method of Treating Tissue Damage and Apparatus for Same", consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499-502—"A New Dressing Method for Free Skin Grafting in Hands".

Medical Industry Week—article "KCI Offers New Treatment for Non-Healing Wounds".

Nakayama, et al., Plast. Reconstr. Surg., Dec. 1990.; vol. 86, No. 6: pp. 1216-1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).

Teder, et al., J. Invest. Surg.1990; vol. 3: pp. 399-407—"Continuous Wound Irrigation in the Pig".

Wood, et al., Br. J. of Surg. 1977; vol. 64: pp. 554-557—"Foam Elastomer Dressing in the Management of Open Granulating Wounds: Experience with 250 Patients".

Neumann, et al., J. of Biomed. Materials Research 1981, vol. 15: pp. 9-18—"Gelatin-Based Sprayable Foam as a Skin Substitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta Physiol. Scand. 1989, vol. 136: pp. 403-409—"Transmission of Externally Applied Negative Pressure to the Underlying Tissue. A Study on the Upper Arm of Man".

Brochure—Aeros—Instavac Aspirator.
Brochure—Pleur-evac Adult-Pediatric-Non-Metered Disposable "3-Bottle" Unit, A-4000.
Brochure—Hiblow Air Pump.
Brochure—Aeros—Care-E-Vac.
Brochure—Aeros—Moblvacll.
Brochure/Instruction Manual—Creative Medical Laboratories, Inc.—TUGS (Transportable Universal Gradient Suction) System.
Brochure—Wells Johnson Company—Point 5 Aspirator.
Brochure—Microtek Heritage, Inc.—The Wound-Evac ET, Closed Wound Suction System.
Brochure—KCI—The V.A.C. (Vacuum Assited Closure).
Brochure—Augustine Medical, Warm-Up Active Wound Therapy Wound Covers, 1999.
Brochure—Series 55—Emerson Post-Operative Suction Pumps.
Brochure—Emerson Transport Suction Unit.

* cited by examiner

| FIG. 7A | FIG. 7B |

FIG. 7

| FIG. 8A(1) | | |
|---|---|---|
| FIG. 8A(2) | FIG. 8B | FIG. 8C |
| FIG. 8D | FIG. 8E | |

FIG. 8

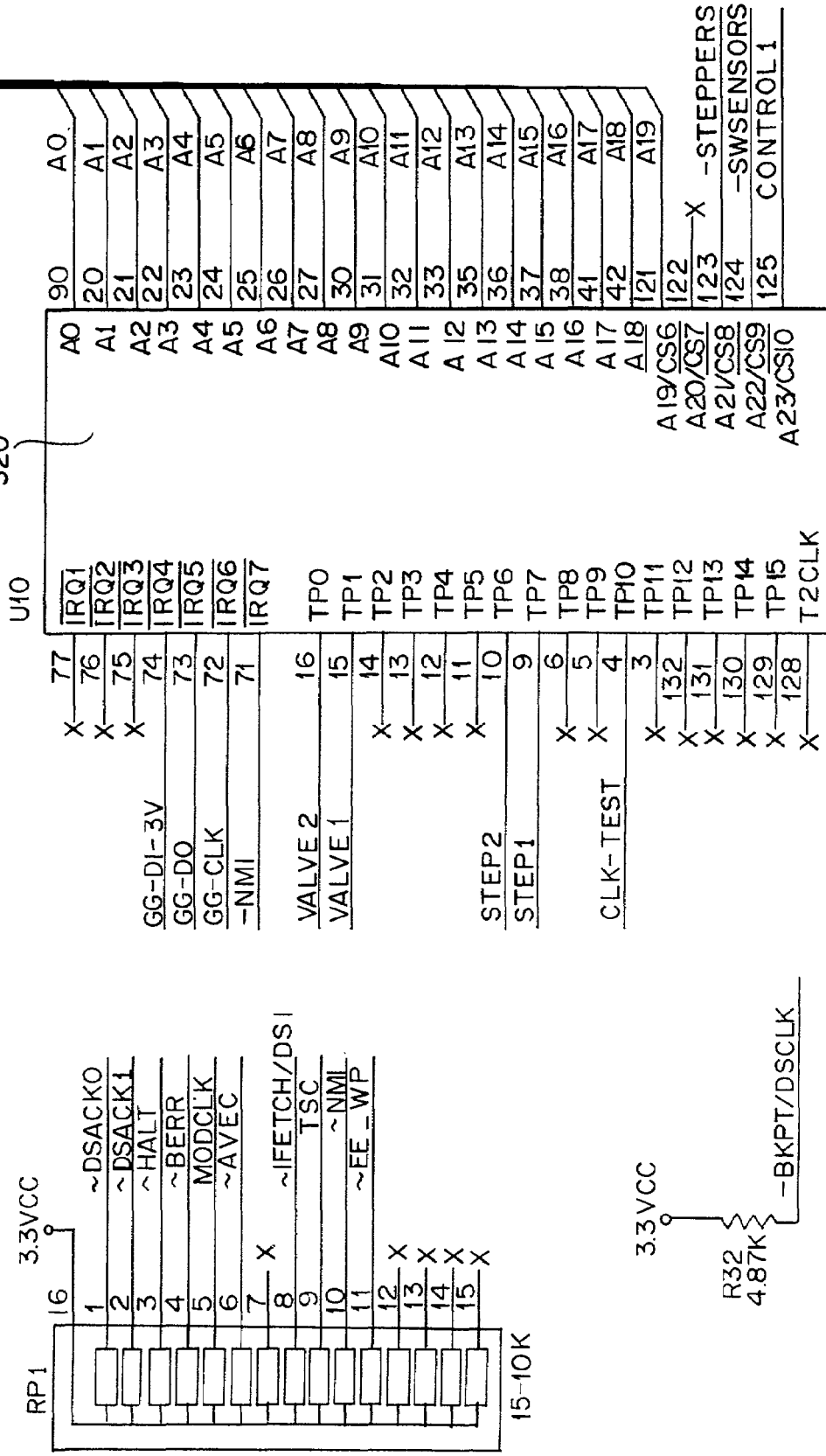
FIG 8A (1)

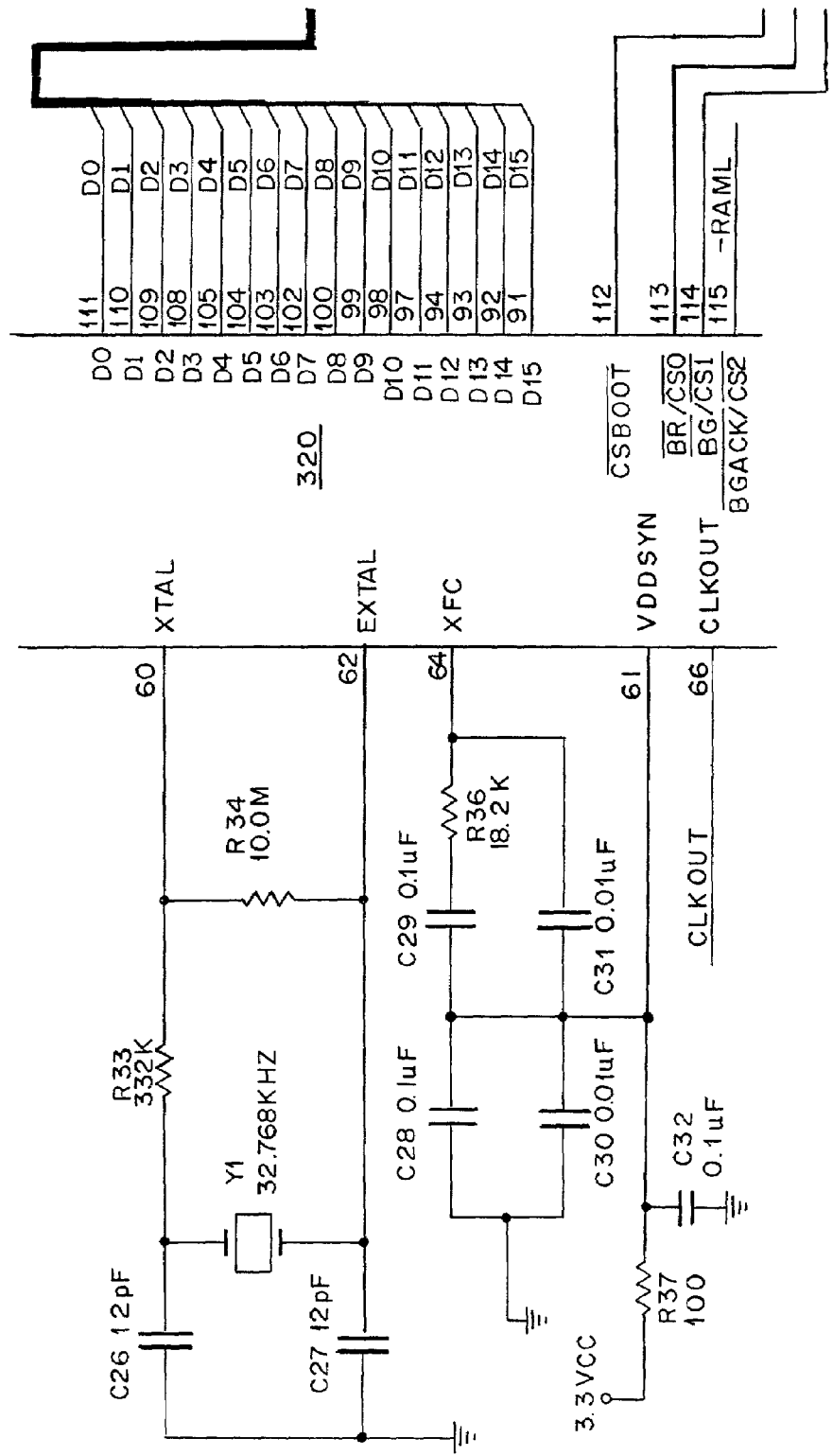
FIG. 8A(2)

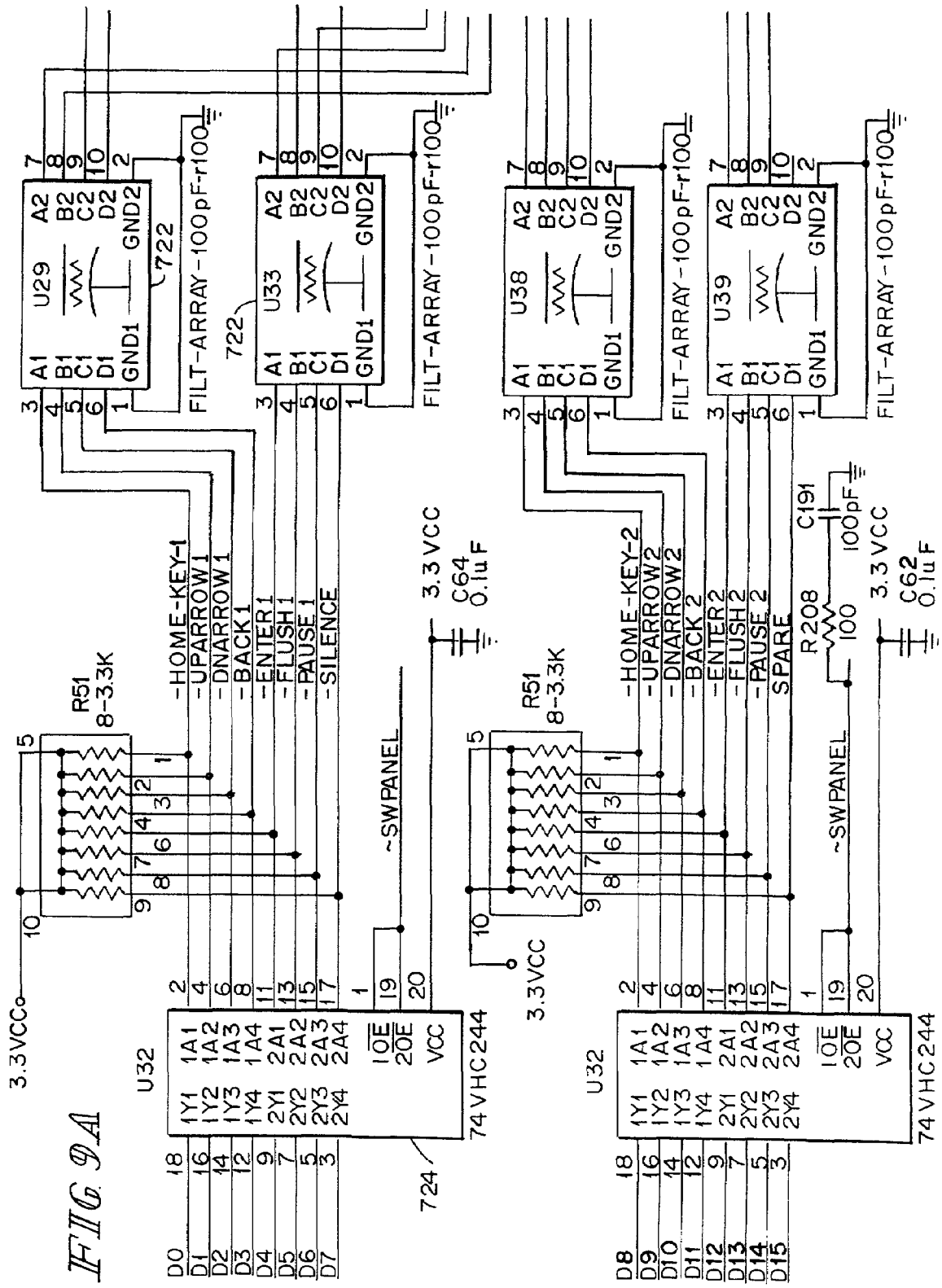

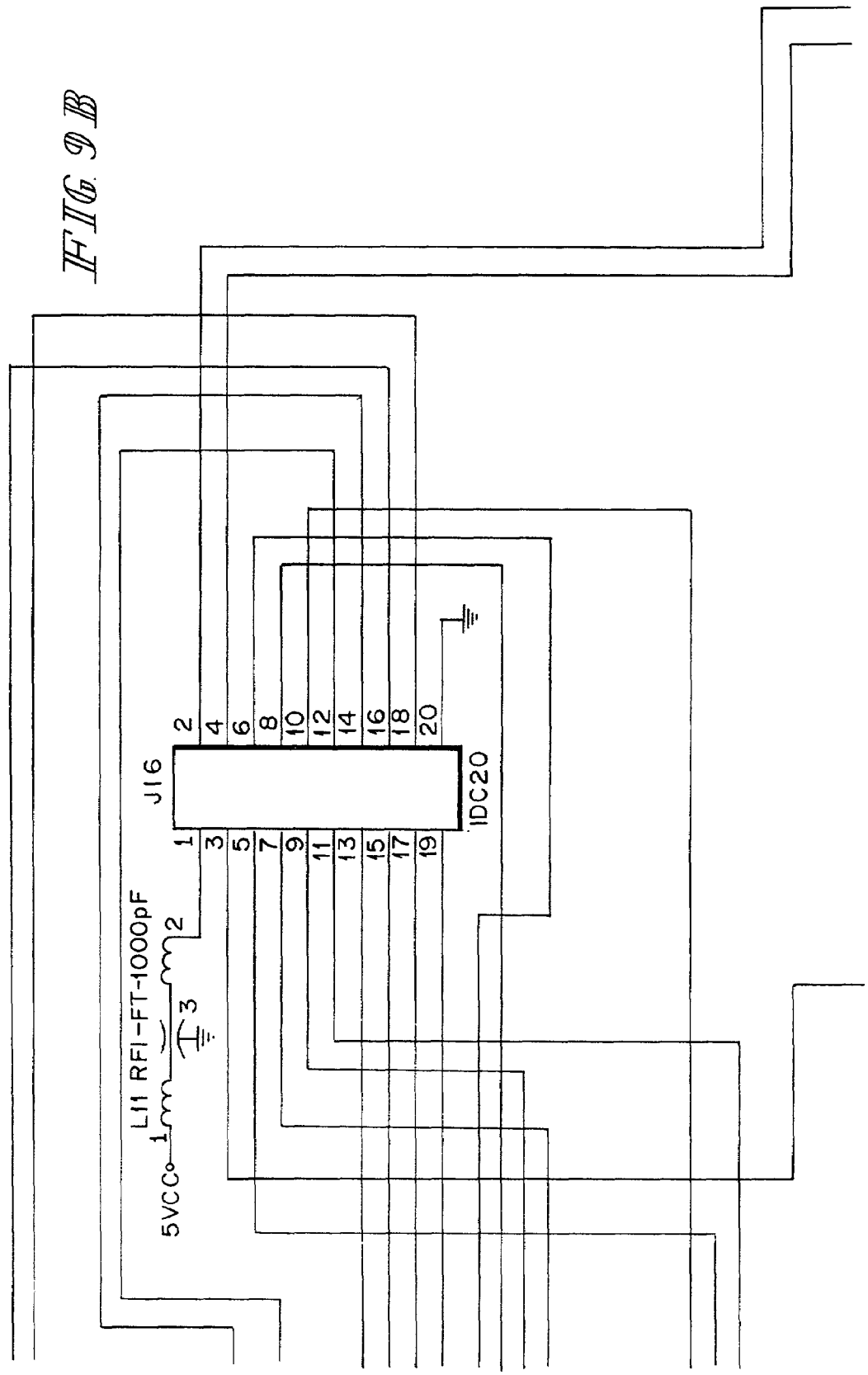

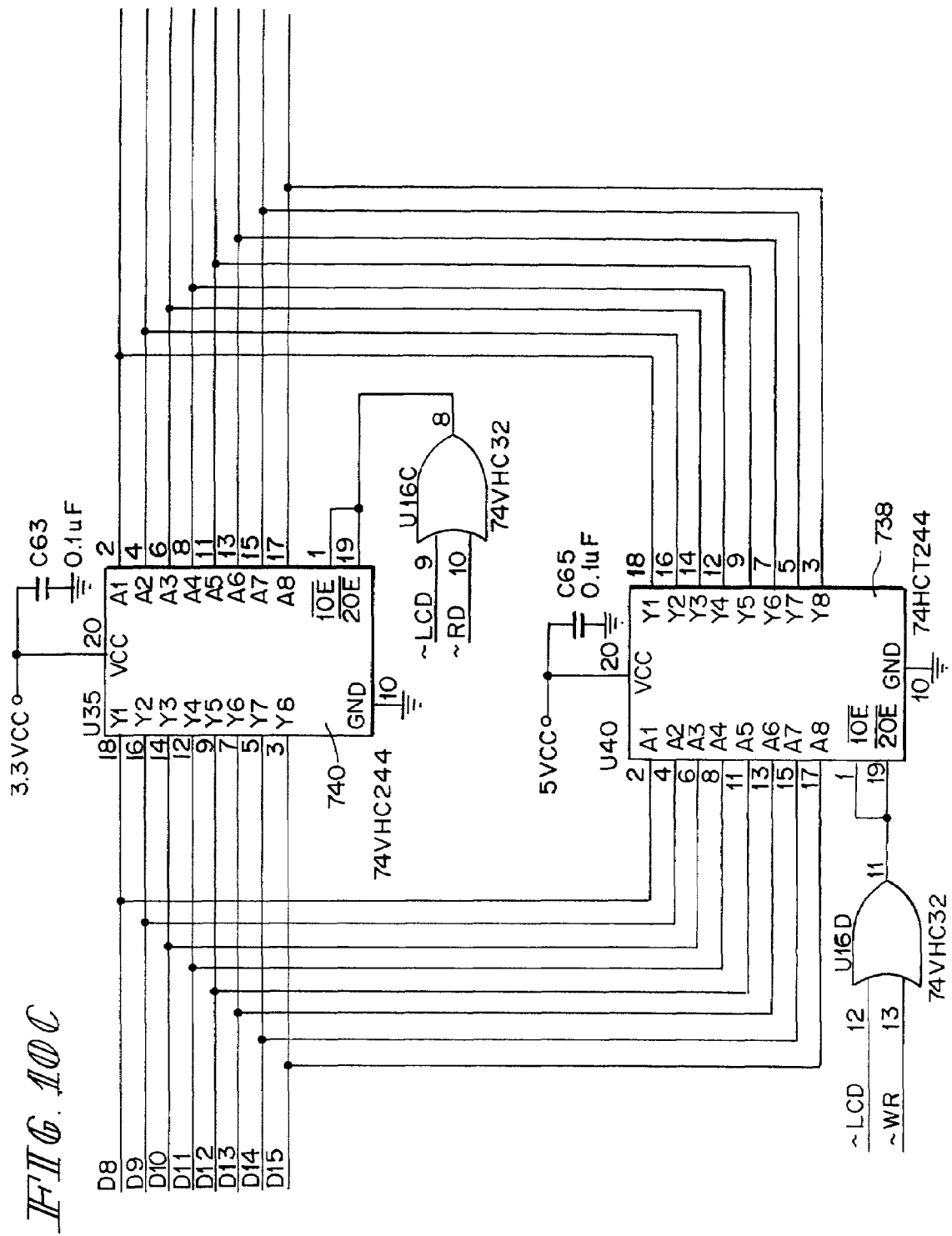

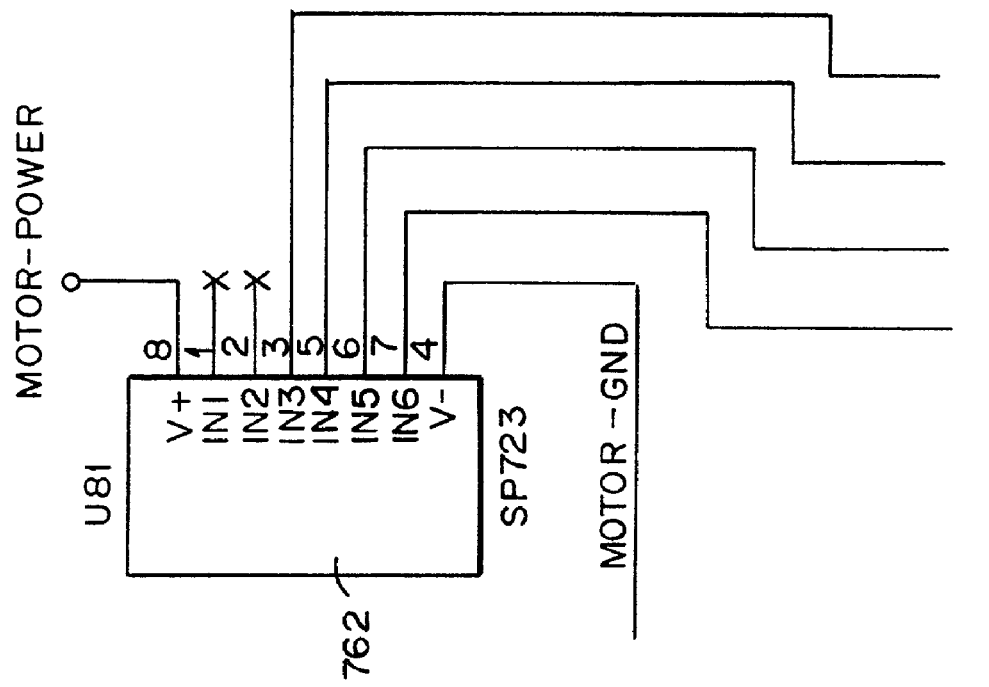
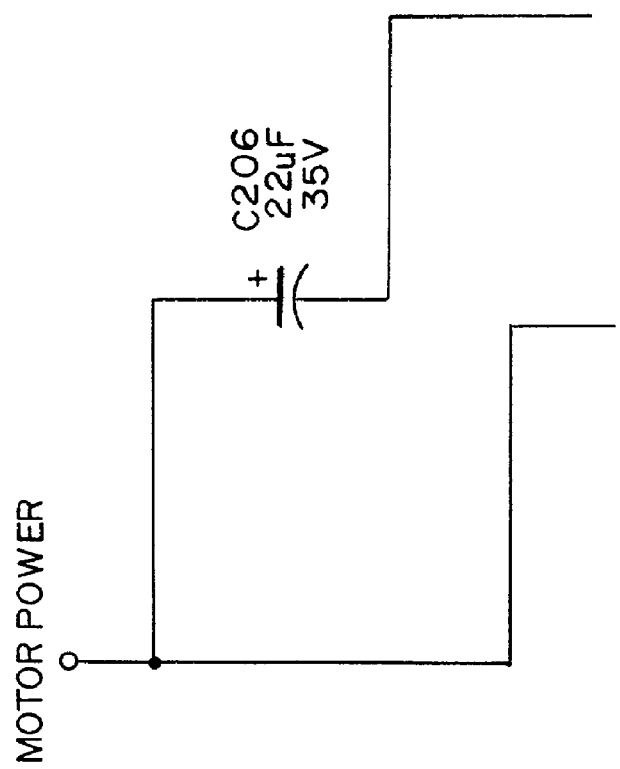
FIG. 11A

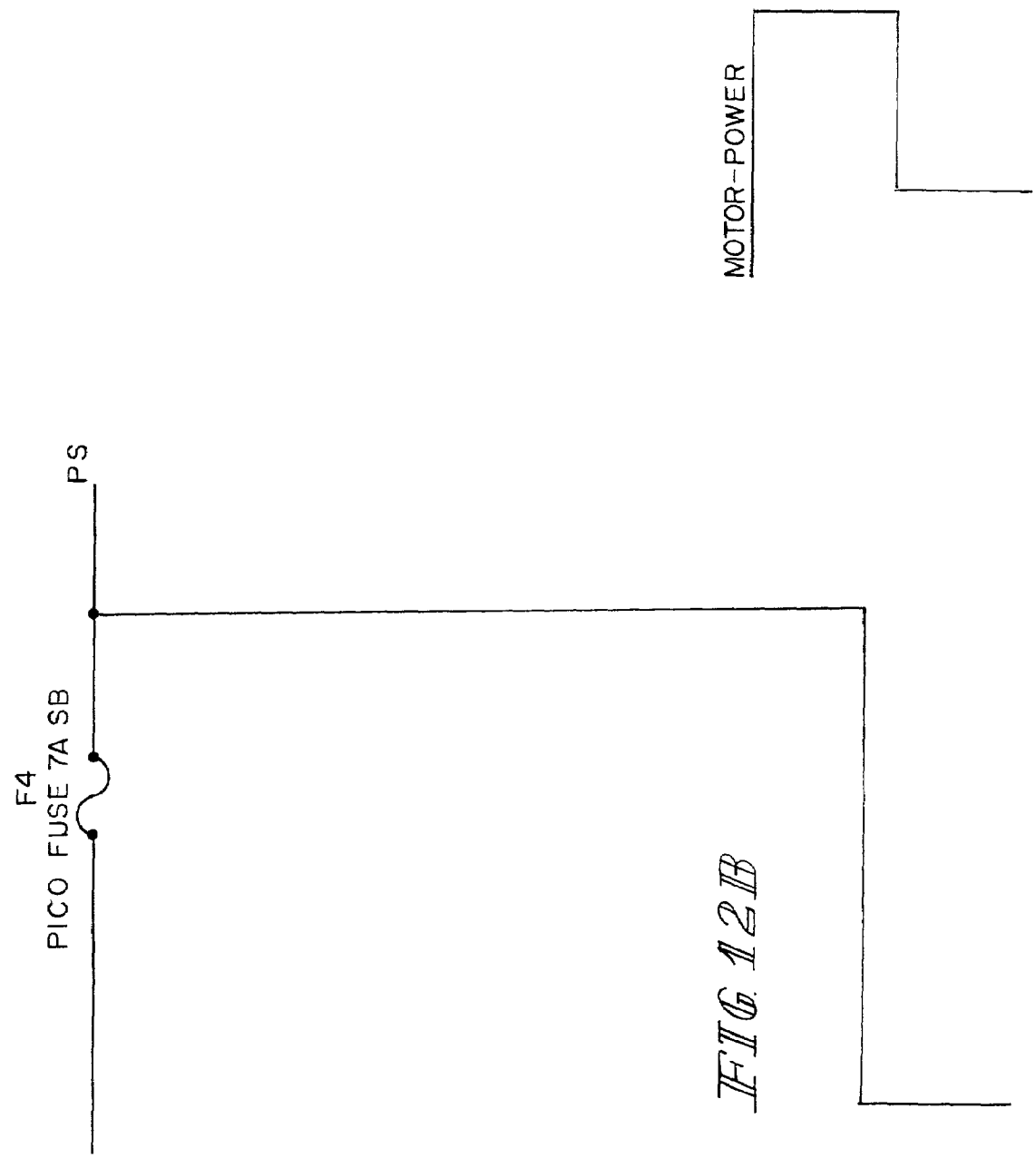

SCALE IS 1 VOLT PER 4 amps WITH A 3.0 VOLT OFFSET.

4 amp CHARGE = 4 VOLTS 1 amp CHARGE = 3.25 VOLTS

0 CURRENT = 3 VOLTS 4 amp DISCHARGE = 2.0 VOLTS 8 amp DISCHARGE = 1 VOLTS 10 amp DISCHARGE = 1.5 VOLTS 12 amp DISCHARGE = 0 VOLTS

| FIG. 13A | FIG. 13B |
|---|---|
| FIG. 13C | FIG. 13D |

FIG. 13

CONTROL OF VACUUM LEVEL RATE OF CHANGE

CROSS-REFERENCE TO RELATED APPLICATIONS

This application claims priority under 35 U.S.C. § 119(e) to U.S. Provisional Patent Application Ser. No. 60/304,990, filed on Jul. 12, 2001, the disclosure of which is hereby incorporated by reference herein.

BACKGROUND

The present invention relates to aggressive wound therapy devices, and more particularly to vacuum wound therapy devices. Even more particularly the invention relates to controlling the vacuum applied by vacuum wound therapy devices.

Medical professionals, such as nurses and doctors, routinely treat patients having surface wounds of varying size, shape, and severity. Aggressive wound therapy, as opposed to passive wound therapy, takes advantage of environmental modifications to actively induce healing. It is known that controlling the topical atmosphere adjacent a wound can enhance the healing process. Several aggressive wound therapy strategies are known including hyperbaric therapy, thermal therapy and negative pressure therapy.

In negative pressure therapy, a wound bed is subjected to an air pressure lower than the ambient air pressure. Applying a negative pressure or vacuum to a wound draws out exudate, which might contain dirt and bacteria, from the wound to further promote healing. Some dressings include an apparatus attached thereto for applying a vacuum through the bandage to the wound to draw exudate and promote healing. However, it has been found that rapid changes in negative pressure levels applied to open wounds (chronic wounds) can cause discomfort to patients.

It is also known to use a vacuum treatment bandage for accelerating wound healing. A vacuum bandage is a bandage having a cover for sealing about the outer perimeter of the wound and under which a vacuum is established to act on the wound surface. This vacuum applied to the wound surface accelerates healing of chronic wounds. Typically, suction tubes are provided for drawing exudate away from the wound, and the suction tubes may be used to create the vacuum under the cover. If the cover is a flexible cover, which is typically more comfortable for the patient, a porous packing may be provided under the cover to provide the space in which the vacuum is formed. Additionally, it is known a heater within a wound treatment apparatus to promote healing. The following U.S. Patents establish the nature of vacuum and/or heat treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum or heat treatment of wounds.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and nonapplication. In a preferred embodiment, pressure is applied in 5-minute periods of application and non-application.

The following pending applications, assigned to the same assignee as the present application is licensed, are also specifically incorporated herein by reference: U.S. patent application Ser. No. 09/369,113 filed Aug. 5, 1999 and titled Wound Treatment Apparatus, U.S. patent application Ser. No. 09/725,352 filed Nov. 29, 2000 (Publication No. US-2002-0065494-A1 published May 30, 2002) and titled Vacuum Therapy and Cleansing Dressing for Wounds, and U.S. patent application Ser. No. 09/725,666 filed Nov. 29, 2000 and titled Wound Treatment Apparatus.

Various prior art references teach the value of the vacuum bandage or the provision of vacuum to the surface of a chronic wound. Several Russian language articles exist that establish the efficacy of vacuum therapy. Examples of such prior art articles, each of which discusses the use of application of vacuum to a wound to promote healing, are as follows: *Vacuum therapy in the treatment of acute suppurative diseases of soft tissues and suppurative wound*, Davydov, et al. Vestn. Khir., September 1988 ("the September 1988 article"); *Pathenogenic mechanism of the effect of vacuum therapy on the course of the wound process*, Davydov, et al. Khirurigiia, June 1990 ("the June 1990 article"); and *Vacuum therapy in the treatment of suppurative lactation mastitis*, Davydov, et al., Vestn. Khir., November 1986 ("the November 1986 article").

The Russian articles distinguish wound drainage from use of vacuum therapy for healing, and they report that vacuum therapy results in faster cleansing of the wound and more rapid detoxification than with the traditional incision-drainage method. The November 1986 article describes the vacuum therapy protocol as 0.8–1.0 atmosphere for 20 minutes at the time of surgery, and subsequent 1.5 to 3 hour treatments at a vacuum of 0.1 to 0.15 atmosphere, twice daily. These Russian articles teach that use of negative pressure accelerates healing. The Russian articles further teach using this vacuum method to decrease the number of microbes in the wound. The June 1990 article teaches that vacuum therapy provides a significant antibacterial effect. The June 1990 article describes the stepped up inflow of blood to the zone around the wound, which leads to an increase in the number of leukocytes reaching the focus of inflamation. Moreover, the Russian articles teach improvement of local blood circulation using vacuum therapy. The September 1988 article teaches improved inflow of blood into the wound zone, which intensifies the repair processes. The June 1990 article teaches that vacuum therapy promotes mobilization of blood plasma, intertissue fluid, and lymph into the wound. The June 1990 article reports that cellular and non-cellular elements of connective tissue appear twice as quickly in wounds treated with vacuum therapy. Subsequent articles and patents further develop the benefits obtained with vacuum therapy. The prior art, therefore, teaches the benefit and value of a vacuum bandage.

SUMMARY

The device disclosed herein limits the rate of change for the negative pressure applied to the wound. The caregiver has the ability to change the negative pressure value and the device controls the rate of change of the negative pressure to reduce patient discomfort.

Accordingly, an illustrative embodiment provides a negative pressure source, a variable flow orifice, a pressure transducer, a vacuum bandage, a controller, and a caregiver interface. The caregiver interface is configured to allow a caregiver to select a negative pressure setpoint. The caregiver enters a desired or setpoint value of negative pressure to be applied to the wound through the caregiver interface. The controller monitors the pressure transducer and compares the value with the setpoint. Based on this comparison, the controller adjusts the variable flow orifice. When a new setpoint is input by the caregiver, the controller limits the input to the variable flow orifice to produce the allowable rate of change of negative pressure as monitored by the pressure transducer.

Additionally, the illustrative embodiment comprises a waste canister operably coupled to the negative pressure source. The canister is coupled to the bandage such that, when a vacuum is applied to the canister, the vacuum is applied to the bandage. In some embodiments the waste canister is a disposable waste canister.

Illustrative embodiments further provide a plurality of valves, canisters and vacuum pumps. Each valve connects one of the vacuum pumps to an associated waste canister. The controller adjusts each valve to establish the level of vacuum in each of the associated canisters. A plurality of vacuum regulators is also provided, each coupled to a respective one of the valves. Each of the regulators is configured to define a maximum level of vacuum. Each of the regulators also comprises an air intake for supplying additional air to an associated one of the pumps. A plurality of transducers is provided. Each transducer is coupled between a respective valve and an associated waste canister for measuring vacuum.

Additional features and advantages of the apparatus will become apparent to those skilled in the art upon consideration of the following detailed description exemplifying the best mode of carrying out the apparatus as presently perceived.

BRIEF DESCRIPTION OF THE DRAWINGS

The illustrative apparatus will be described hereinafter with reference to the attached drawings, which are given as non-limiting examples only, in which:

FIGS. 6, 7A, 7B, 8A–8E, 9A–9D, 10A–10F, 11A–11C, 12A–12E, 13A–13D, 14, 15A–15D, 16 and 17 illustrate an electric circuit realization of the controller of the wound treatment apparatus.

DETAILED DESCRIPTION OF THE DRAWINGS

Figure 1:
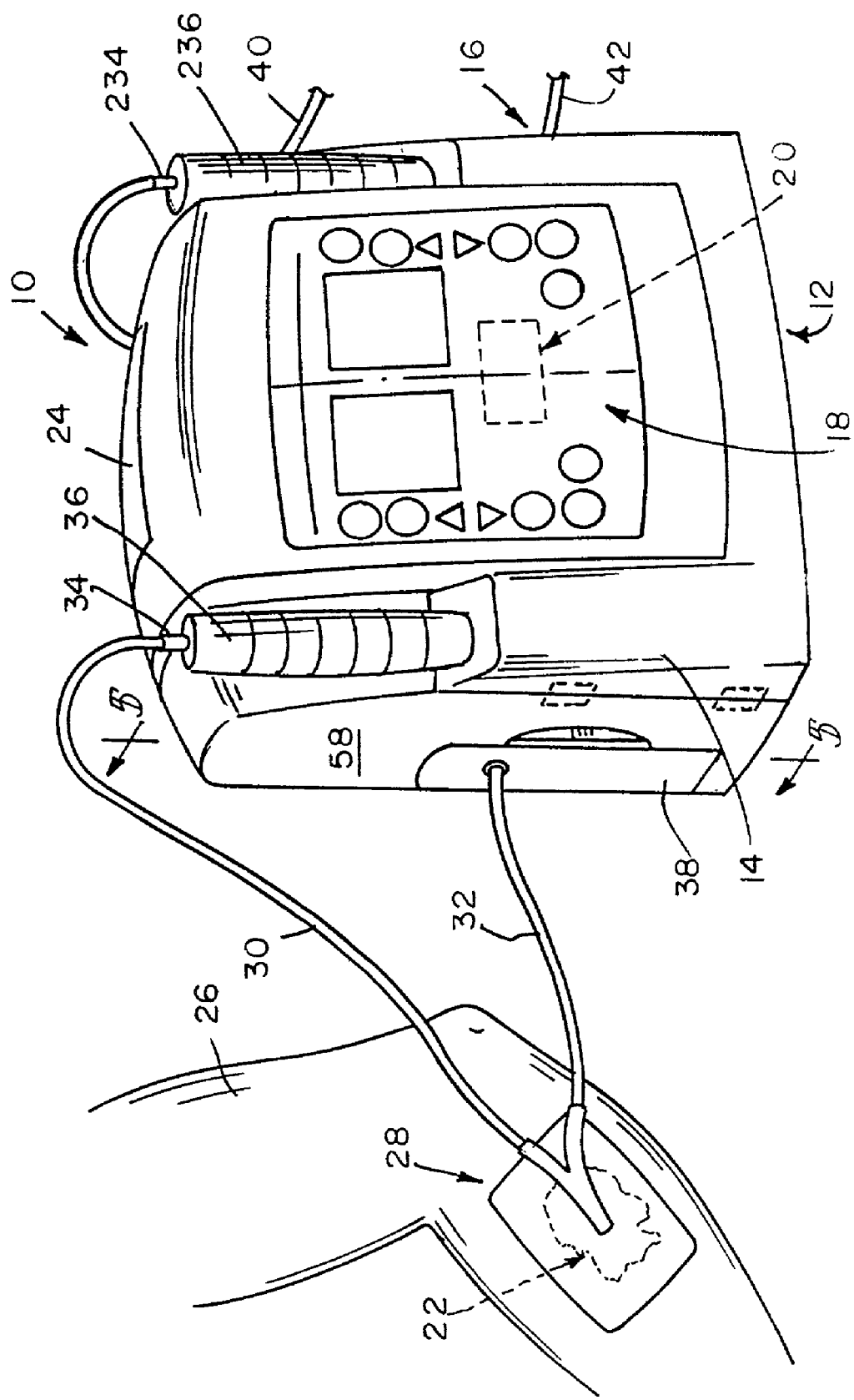
FIG. 1 is a perspective view of a wound treatment apparatus coupled to a bandage attached to a patient.
Figure 2:
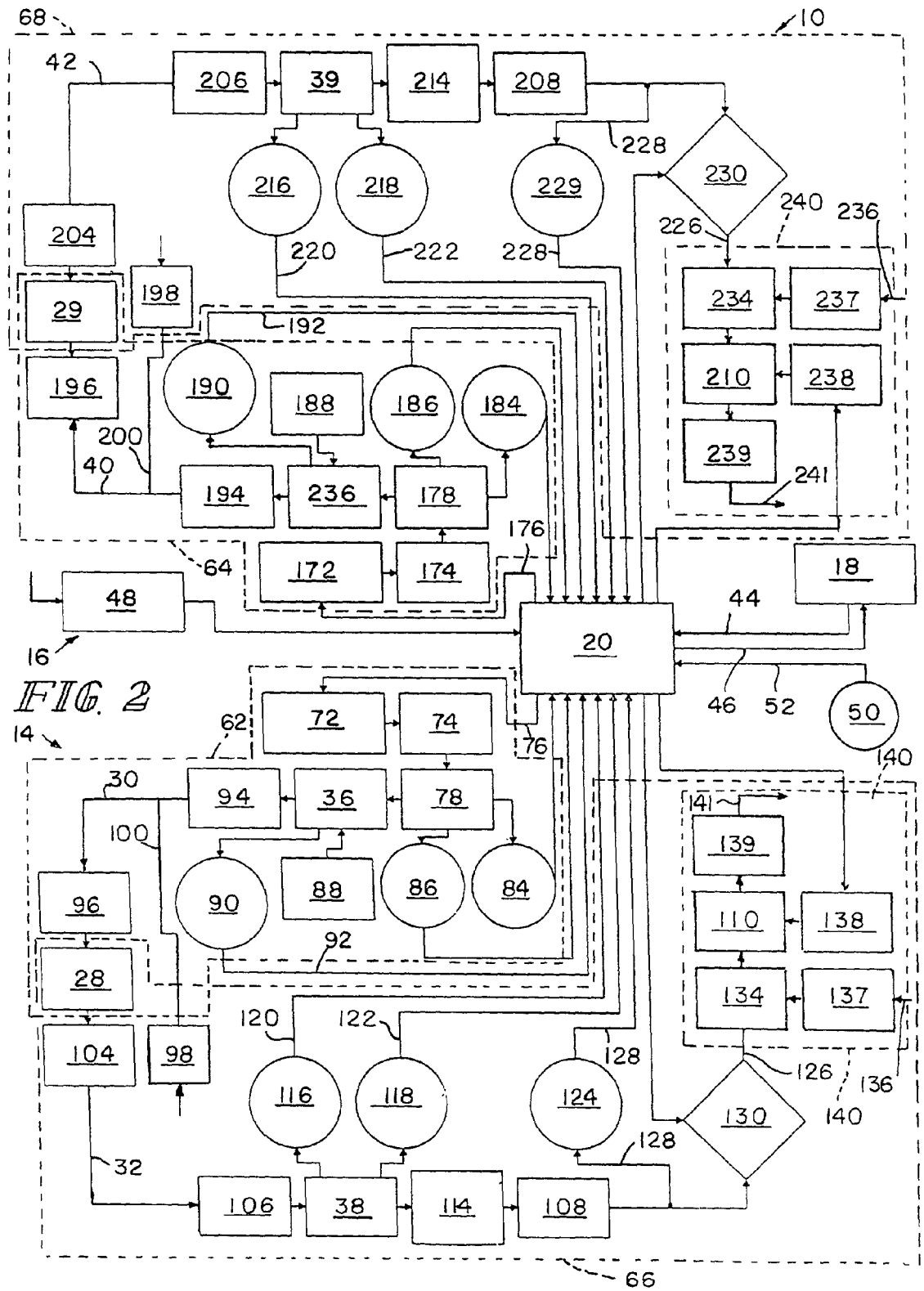
FIG. 2 is a block diagram of the wound treatment apparatus of FIG. 1.
Figure 3:
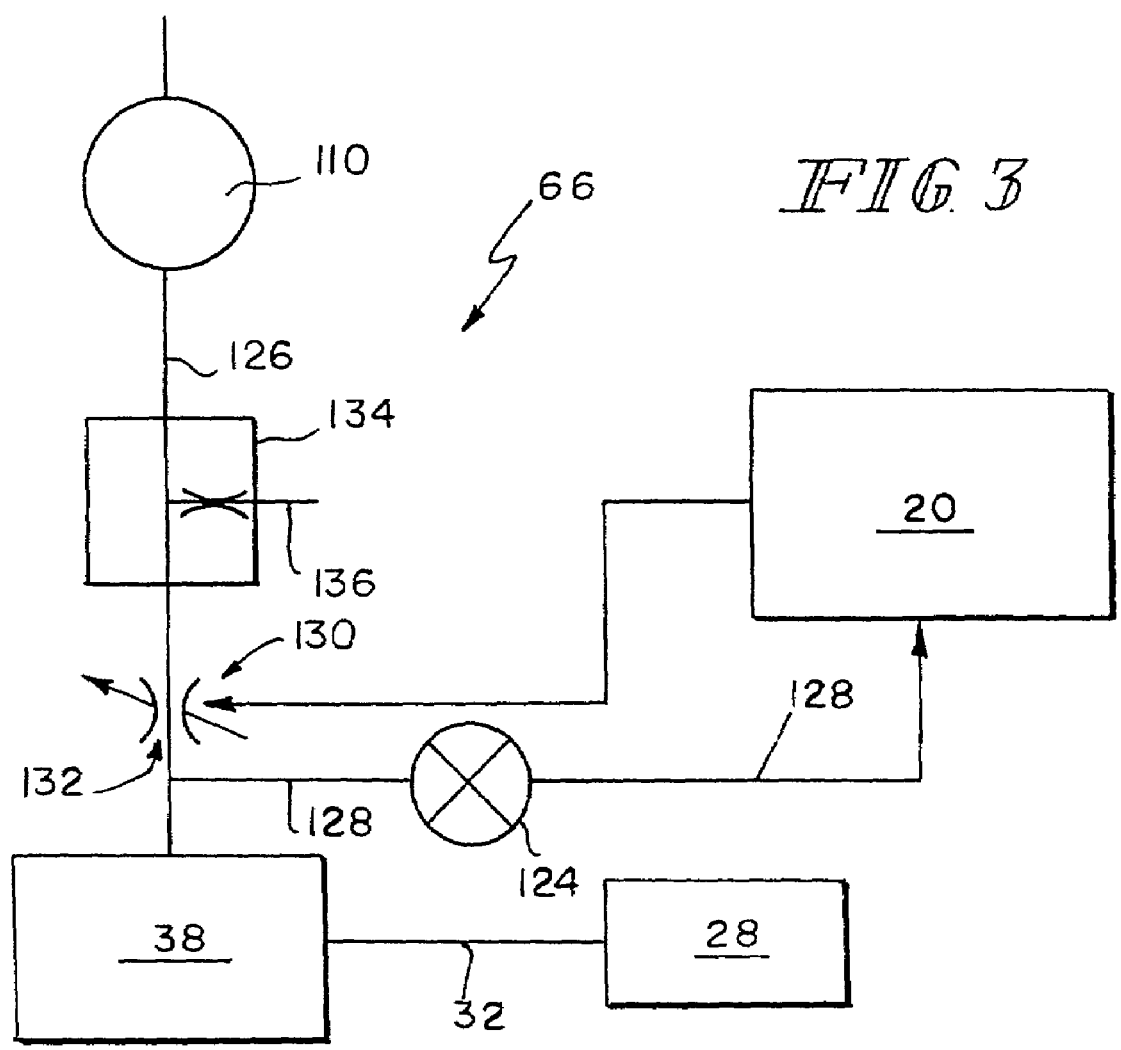
FIG. 3 is a schematic block diagram of the vacuum evacuating sub-system of the wound treatment apparatus of FIG. 1.

An embodiment of a wound treatment apparatus 10 utilizing a vacuum level rate of change controller 20 is shown in FIGS. 1 and 2. This embodiment utilizes a vacuum level rate of change controller 20 with a wound treatment apparatus 10 having wound irrigation subsystems and wound evacuation subsystems. Appropriate wound treatment apparatus which can be modified to use controller 20 are disclosed more particularly in U.S. patent application Ser. No. 09/725,666 filed on Nov. 29, 2000 and U.S. patent application Ser. No. 09/725,352 filed on Nov. 29, 2000 (U.S. publication no. US-2002-0065494-A1 published May 30, 2002, the disclosures of which have been previously incorporated by reference into this disclosure.

Wound treatment apparatus 10 comprises a central unit housing 12, having wound treatment systems 14, 16 appended to each side of housing 12. A user interface 18 is shown positioned between each treatment system 14, 16. Central unit housing 12 is configured to be a portable unit allowing a caregiver to move apparatus 10 to wherever the patient 26 is located and to close proximity to the wound or wounds 22. Housing 12 is shown having a handle portion 24 to assist the caregiver in moving housing. FIG. 1 also shows wound treatment system 14 coupled to a bandage 28 attached to a leg of a patient 26. Evacuating tube 32 is coupled to both bandage 28 and system 14. Also shown is a dispensing tube 30 coupled to a luer-lok port 34 extending from a syringe 36 to allow irrigation and/or medication of the wound 22. Syringe 36 is filled with a fluid, typically saline, that empties through tube 30 and into bandage 28, and ultimately onto a wound 22 positioned under bandage 28. Exudate from wound 22 are drawn from bandage 28 through evacuating tube 32 and into a waste canister 38 where it is collected. It is contemplated that the canister 38 can be discarded when filled and replaced with a new canister.

Apparatus 10 comprises a second system 16 on the opposite side of housing 12 from system 14. This configuration allows two wounds to be treated simultaneously with separate bandages 28, 29, yet, under the control of a single controller 20 located in a single housing 12. Second bandage 29, as part of system 16, is coupled to a dispensing tube 40 and an evacuating tube 42, to perform the same functions as described for system 14. (See FIG. 2.) User interface 18 is provided to allow the caregiver to provide setpoint and mode information used by controller 20 to control either or both systems 14, 16, to dispense fluid from either or both syringes 36, 236, and to evacuate from either or both bandages 28, 29. It is contemplated that each wound treatment system 14, 16 will work independent of the other, thus, allowing the caregiver flexibility to apply an appropriate and, yet, possibly different level of treatment to each wound 22. The arrangement of systems relative to user interface 18 on housing 12 allows convenient interaction between systems 14, 16 and the caregiver. Those skilled in the art will recognize that while two systems 14, 16 are illustrated, the teachings of this disclosure are applicable to a single system or to a plurality of systems.

The portability of apparatus 10 allows a caregiver to position it near the patient 26 in preparation for treatment wherever the patient 26 is located. To prepare apparatus 10 for treatment, the caregiver couples tube 30 to bandage 28 and waste canister 38, for treatment of one wound. The caregiver then couples tube 42 to bandage 29 and waste canister 39, for treatment of a second wound. (See also FIG. 2.) The caregiver, through the use of user interface 18, can treat the patient 26 by drawing exudate from the wounds.

A diagram depicting how wound apparatus 10 operates is shown in FIG. 2. A controller 20 is provided in housing 12. Illustratively, controller 20 is an electronic control unit that controls apparatus 10. Controller 20 receives user input from and provides feedback to user interface 18 through lines 44, 46, respectively. It is contemplated that controller 20 will process information from both systems 14, 16, and provide appropriate and independent input to each system 14, 16. Controller 20 also monitors the status of all various sensors, and provides input for the valves and motors to control the value of the negative pressure and the rate of change of the negative pressure, as discussed in further detail herein. Illustratively, user interface 18 is composed of a conventional graphic liquid crystal display (LCD) and a membrane switch panel.

A power supply 48 provides power to controller 20 and all the attendant systems in housing 12. Power supply 48 can be a conventional external wall socket supply (not shown), or be a battery pack supply (also not shown), or even be variations of both (e.g., a wall socket supply with a battery pack supply). Illustratively, power supply 48 is a medical grade power supply providing an output of about 65 watts and a voltage of about 12VDC. It is contemplated that the power supply 48 can be configured for 120V/60 Hz or 220–240V/50 Hz depending on whether apparatus 10 is used in America or Europe. Illustratively, the battery power provides the device with power to operate for about 60 minutes without connection to an external power source. It is further contemplated that the batteries can be rechargeable, and store energy when the device is connected to an external wall socket.

An attitude sensor 50 is provided in communication with controller 20 through line 52. Attitude sensor 50 is, illustratively, a tilt switch which provides feedback to controller 20. If the switch is, illustratively, in the closed position, controller 20 will continue to operate, but if the switch opens, controller 20 will shut systems 14, 16 down. For example, sensor 50 disables systems 14, 16 if housing 12 tilts at or greater than a predetermined amount, such as 45° from vertical in any direction.

It is contemplated that controller 20, user interface 18, power supply 486, and attitude sensor 50 are all common to and all operate with both systems 14, 16. Each system 14, 16 further comprises fluid dispensing sub-systems 62, 64 and vacuum evacuating sub-systems 66, 68. Fluid dispensing sub-system 62 comprises a syringe 36 having a plunger. Syringe 36 is, illustratively, a standard 60-ml medical syringe utilizing a luer-lok port 34. Plunger is a conventional plunger that extends into syringe 36 to dispense fluid through luer-lok port 34. A syringe drive motor 72 is, illustratively, a 12VDC brushless electric motor or stepper motor configured to provide rotational energy to a syringe drive 74. When a signal is sent from controller 20 along line 76 to syringe drive motor 72, motor 72 applies torque and angular velocity to syringe drive 74 which is, illustratively, a power screw. Power screw translates rotational movement of the syringe drive motor 72 into translational movement. The drive has a guide to limit a plunger interface 78 to motion along one axis. In the illustrated embodiment, syringe drive 72 provides about 5.25 inches (13.3 cm) of travel of plunger interface 78 to evacuate the fluid contained in syringe 24. Furthermore, syringe drive motor 72 and syringe drive 74, as a system, provide about 27 pounds of linear force at a velocity of 1.45 inches (3.7 cm) per second to the plunger interface 78. The resulting force created by the fluid exiting syringe 36 creates, illustratively, 4-PSIG to 6-PSIG positive pressure at wound 22.

A syringe home sensor 84 receives information from plunger interface 78, and provides feedback to controller 20 when syringe capture mechanism 88 reaches its home position. A syringe full travel sensor 86 determines when syringe 36 is fully evacuated by sensing when plunger interface 78 has reached full travel. After sensor 86 has been activated, controller 20 resets plunger interface 78 to home position once syringe 36 is removed.

Syringe capture mechanism 88 holds syringe 36 in place when the caregiver places syringe 36 in apparatus 10. Capture mechanism 88 is also configured to allow the caregiver to release syringe 36 from apparatus 10 when it is empty. Capture mechanism 88 further includes a syringe sensor 90 that provides feedback to controller 20 through line 92 when syringe 36 is properly held in capture mechanism 88. Controller 20 prevents system 14 from operating if sensor 90 does not detect syringe 36 being properly held in capture mechanism 88.

Connectors 94, 96 are provided at opposed ends of dispensing tube 30. Either one or both connectors 94, 96, when closed, block flow from syringe 36 to bandage 28. Such connectors 94, 96 allow the patient 26 to be disconnected from apparatus 10 without having to remove bandage 28 or even shut apparatus 10 down.

A manual port 98 is also attached to dispensing tube 30 by an auxiliary tube 100. Port 98 permits the caregiver to attach a dispensing container to the system to manually dispense fluid into bandage 28. It is appreciated, however, that port 98 is configured to be closed while no syringe is attached to maintain a closed system.

The syringe and drive are illustrated as one approach for providing a fluid source and a drive for irrigating a wound bed. It will be appreciated that containers other than syringes may be operated by a drive to expel irrigation fluid toward a wound surface. For example, any type of container of fluid may be squeezed or reduced in volume by a drive mechanism to expel fluid. Also, a container may be held at an elevated position to provide head pressure for irrigation fluid.

Connectors 104, 106, similar to connectors 94, 96, are provided at opposed ends of evacuating tube 32. Either one or both connectors 104, 106, when closed, block flow from bandage 28 to waste canister 38. Such connectors 104, 106 also allow the patient 26 to be disconnected from apparatus 10 without having to remove bandage 28 or having to shut down apparatus 10.

Waste canister sensors 116, 118 are engaged when waste container 38 is properly seated in apparatus 10. This prevents apparatus 10 from operating without canister 38 seated properly in apparatus 10. As depicted in FIG. 2, both sensors 116, 118 provide feedback to controller 20 through lines 120, 122, confirming to the caregiver that canister 38 is seated properly in apparatus 10.

In the illustrated embodiment, waste canister 38 is a disposable unit that "snaps into" side portion 58 of housing 12. (See also FIG. 1.) Illustratively, canister 38 includes a window (not shown) to allow monitoring of the fluids. Illustratively, the fluid capacity of canister 38 is about 500-ml.

The illustrated embodiment of waste canister 38 further includes a hydrophobic filter 108 that is in communication with both evacuating tube 32 and vacuum pump 110. Such filter 108 is configured to allow air, but not liquid, to pass. Accordingly, as fluid is drawn into canister 38, fluid is deposited into waste canister 38 while the vacuum continues through filter 108 and pump 110. Illustratively, filter 108 is a 0.2-micron hydrophobic bacteria filter fixed into rear wall 407 of canister 38. Hydrophobic filter 108 also serves as a canister full mechanism 114 or valve that shuts off the vacuum supply to the canister 38 when the fluid level exceeds the "full" level. Because hydrophobic filter 108 prevents fluid from passing, once fluid covers filter 108, vacuum is prevented from passing as well. Illustratively, the absence of any vacuum in the system causes the system to shut down.

Vacuum pump 110 creates the negative pressure that is present through canister 38. For monitoring and controlling such negative pressure, the vacuum is present through several devices, including a vacuum pressure transducer 124. Transducer 124 is coupled to line 128, extending from canister 38. Transducer 124 measures the negative pressure that is present through canister 38. Transducer 124 then provides feedback to controller 20 through line 128. Controller 20 monitors the negative pressure by comparing the measured value from transducer 124 with the caregiver-defined or setpoint value entered into controller 20 through user interface 18.

Figure 5:
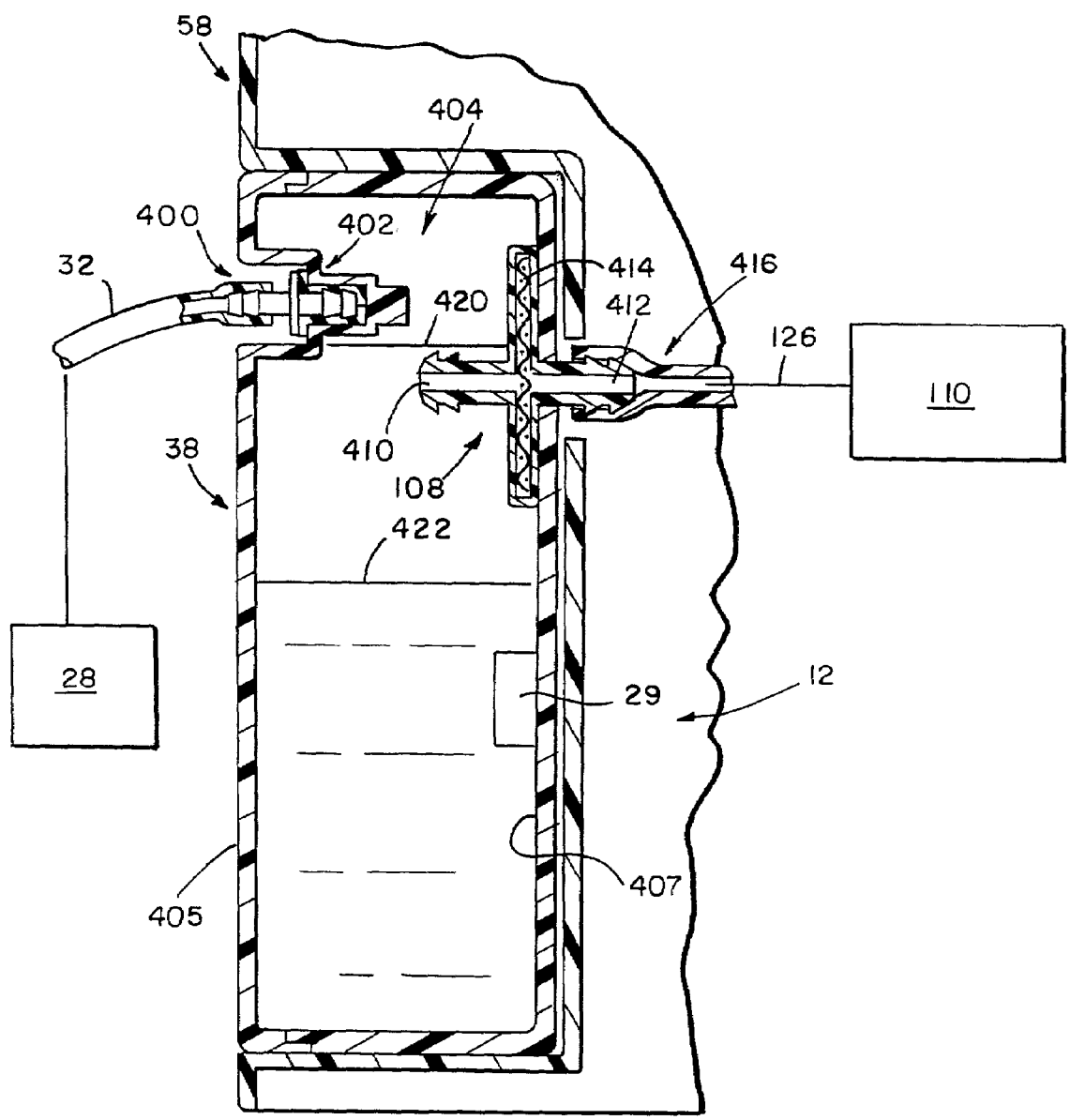
FIG. 5 is a cross-sectional view of a waste disposal canister of the wound treatment apparatus along the lines 5—5 of FIG. 1.

A proportional valve 130 is connected to line 126, through which the negative pressure is present, and which comprises a flow orifice 132. (See also FIG. 5.) Illustratively, proportional valve 130 is solenoid controlled. Flow orifice 132 selectively dilates or constricts, thereby controlling the negative pressure level through sub-system 66. Specifically, controller 20 provides a signal input to proportional valve 130 based on the level of the vacuum pressure determined from feedback of transducer 124 and comparing that level to the caregiver-defined level. Orifice 132 then dilates or constricts, as necessary, to produce the appropriate level of negative pressure. Illustratively, proportional valve 130 is fully constricted or closed when receiving no signal from controller 20, and dilates or opens to allow an illustrative maximum of two liters per minute at 250-mmHg (4.83-PSIG) vacuum when the proper signal from controller 20 is applied. Illustrative examples of a solenoid control valve 130 are the series of standard normally closed proportional solenoid valves available from the Pneutronics Division of Parker Hannifin Corporation, of Hollis, N.H., and having part nos. of the form VSONC-_-_-___-__ wherein the blanks are filled with alphanumeric symbols for the model numbers, body series, elastomer material, coil resistance, electrical interface, and pneumatic interface, respectively. Those skilled in the art will recognize that other controllable valves may be used within the teaching of the disclosure. Also, control may be exercised over other components of the system to adjust the pressure presented to the vacuum bandage 28 and the rate of change of the pressure present at the vacuum bandage 28 within the teaching of the disclosure.

A vacuum regulator 134 is provided in line 126 between proportional valve 130 and pump 110 as a mechanical limit control for pump 110. Regulator 134 mechanically establishes a maximum level of negative pressure that is present in the system. Thus, vacuum pump 110 will not physically be able to draw a vacuum from bandage 28 beyond the maximum pressure. Illustratively, such maximum negative pressure or vacuum is 250-mmHg (4.83-PSIG). In addition, when proportional valve 130, pursuant to a signal from controller 20, creates a negative pressure less than the maximum negative pressure level, a port 136, coupled to regulator 134, opens so that pump 110 can draw more air to maintain a sufficient flow through pump 110, to prevent it from becoming damaged. A first air filter 137 is illustratively associated with port 136, between port 136 and pump 110, to filter particulates from the air prior to reaching pump 110. Illustratively, filter 137 is constructed of glass microfibers with a filtration rating of 25 microns. A second filter 139 is associated with pump 110 and an outlet 141. Filter 139 serves as an exhaust muffler for the air evacuated from pump 110.

Vacuum pump 110 is, illustratively, a diaphragm-type compressor that flows about two liters per minute at 250-mmHg (4.83-PSIG) vacuum. Illustratively, vacuum pump 110 is mounted on the end of a single 12VDC brushless motor 138 to drive the pump. It is appreciated, however, that pump 110 can be of any other configuration, and mounted in any manner, so long as it draws a desired negative pressure through system 14. It is also contemplated that a vacuum pump external to the housing 12 may be a part of the control system. For example, most medical facilities have vacuum ports near where patients are treated, each of which is served by a system vacuum (suction) pump. It is contemplated, therefore, that the pump 110 in the housing 12 may be an appropriate fitting which is, in turn, connected to a facility vacuum pump to provide a vacuum source to the control system.

It is contemplated that port 136, filters 137, 139, electric motor 138, vacuum pump 110, and vacuum regulator 134 are all housed in a sound chamber 140. Illustratively, the interior of sound chamber 140 is lined with a damping foil like the 3M Company's damping foil number 2552, for example. Sound chamber 140 dampens vibration energy produced by these components, as well as assists in dissipating heat they generate.

As previously indicated, it is contemplated that controller 20, user interface 18, and power supply 48 are common to, and operate with, both fluid dispensing and vacuum evacuating sub-systems 62, 64 and 66, 68. Providing a second independently operable set of sub-systems 64, 68 allows the caregiver to treat two wounds using a single apparatus 10. Accordingly, second fluid dispensing and evacuating sub-systems 64, 68 also shown in FIG. 2, comprise identical components as discussed regarding sub-systems 62, 66 and are labeled in a corresponding manner. For example, syringe motor drive 72 in sub-system 142 is identified as syringe motor drive 172 in sub-system 64, and a vacuum pump 110 in sub-system 66 is identified as vacuum pump 210 in sub-system 68.

Vacuum 110 applies a negative pressure through waste canister 38 and bandage 14. Fluid and exudate are then drawn from wound 22 out through tube 32 and into canister 38. The hydrophobic filter 108, discussed in connection with FIG. 2, allows the vacuum to pass through waste canister 38, yet, prevents any of the fluid from escaping, and depositing the fluid into pump 110.

Figure 4:
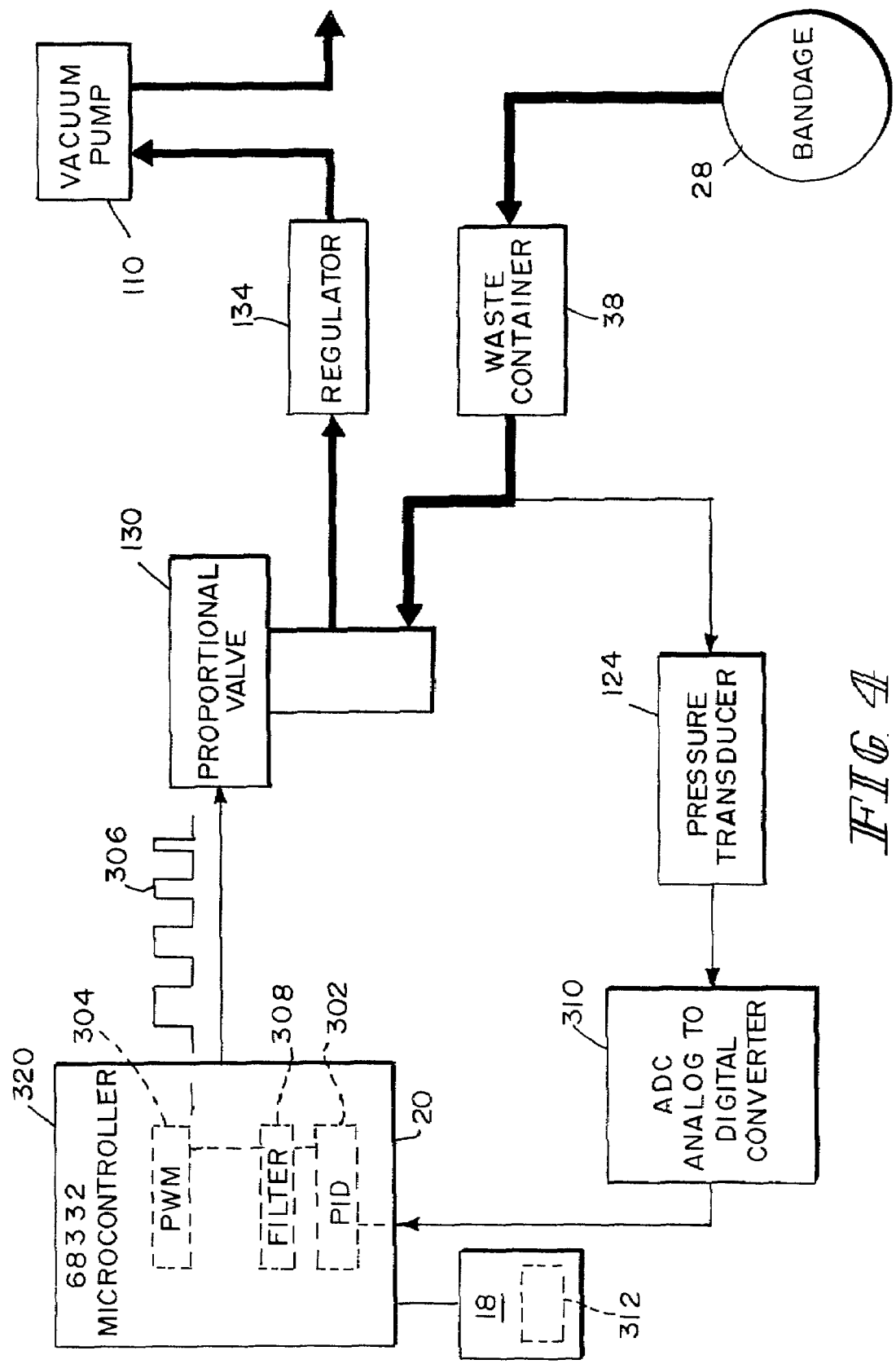
FIG. 4 is a block diagram of the vacuum evacuating subsystem of FIG. 1 showing the controller in more detail than is shown in FIG. 4.

A cross-sectional view of waste canister 38 located in cavity on side 58 of housing 12 is shown in FIG. 4. Tube 32 is connected to a check-valve assembly 400 coupled to recess 402 disposed in the front wall 405 of canister 38. Check valve 400 is configured to allow fluid and exudate from bandage 28 to enter canister 38 and deposit in holding space 404 within canister 38, yet prevent any fluid already in space 404 from exiting through valve 400. Check valve 400, thus prevents fluid from escaping when tube 32 is disengaged from valve 400. In addition, canister 38 can be discarded without any fluid escaping. Hydrophobic filter 108 is located on the rear wall 407 of canister 38. A liquid solidifier is provided in space 404 to decrease the fluidity of the exudate. This is a safety measure to lessen the chance of splashing or run-off if canister 38 (or 39) is opened or broken.

Filter 108 in canister 38 is shown having an inlet 410 provided in space 404 and an outlet 412 coupled to a connector 416 with a barrier of hydrophobic material 414 provided therebetween. As previously discussed, the hydrophobic material allows the vacuum to pass through inlet 410 and outlet 412, yet prevents any fluid from passing. Similar to check valve 400, hydrophobic filter 108 also prevents any fluid from escaping when canister 38 is removed from housing 12. Outlet 412 of filter 108 is in communication with connector 416. Connector 416 is configured to receive and seal outlet 412 when canister is positioned in cavity. Connector 416 is in communication with line 126 and ultimately with pump 110.

In the illustrated embodiment, hydrophobic filter 108 serves as both the canister full mechanism 114 that shuts off the vacuum supply to the canister 38 when the fluid level exceeds the "full" level as indicated by reference numeral 420. When the fluid level is below inlet 410, as indicated by reference numeral 422, fluid continues to enter space 404 through valve 400. When the fluid level 420 is above inlet 410, the fluid is acting as an air block. Fluid cannot pass through filter 108, but because the fluid level is above inlet 410, air cannot pass through either. This causes a dramatic pressure drop (vacuum increase) through line 126. Vacuum pressure transducer 124 is coupled to line 126 measuring the negative pressure passing through canister 38, as previously discussed. If such a dramatic pressure drop occurs, transducer 124 will provide such data to controller 20 through line 128. Controller 20 will then know to shut the system down until the full canister is replaced with either an empty or only a partially full canister.

Illustrative vacuum bandage 28 is designed to provide a protective environment around wound 22. Illustratively, such bandages last for up to 7 days without having to be replaced. Bandage 28 includes rinse and drain orifices (not shown) within the body of bandage 28 that communicate with tubes 30, 32, respectively. Such orifices are illustratively 0.070-inch (0.18 cm) diameter. Vacuum evacuating sub-system 66 cooperates with bandage to draw the fluid and exudate from the surface of wound 22, and collect the same into waste canister 38.

Examples of bandages 14 are shown and described in U.S. patent application Ser. No. 09/725352, entitled VACUUM THERAPY AND CLEANSING DRESSING FOR WOUNDS, filed on Nov. 29, 2000 and in U.S. patent application Ser. No. 10/144,504, also entitled VACUUM THERAPY AND CLEANSING DRESSING FOR WOUNDS, filed May 13, 2002, the complete disclosures of which are hereby expressly incorporated by reference herein. It is further contemplated that other bandages may be used with this control system, including bandages having separate irrigation and vacuum ports. Examples of such bandages are shown and described in U.S. patent application Ser. No. 09/369,113, entitled WOUND TREATMENT APPARATUS, filed on Aug. 5, 1999, (assigned to the same Assignee or Affiliated Assignee as the present disclosure), the complete disclosure of which is hereby expressly incorporated by reference hererin. Further details of wound treatment apparatus 10 and alternative embodiments thereof are shown and described in U.S. patent application Ser. No. 10/159,583, entitled WOUND TREATMENT APPARA-TUS, filed on May 31, 2002, the complete disclosure of which is hereby expressly incorporated by reference herein.

Illustratively, the caregiver may activate system 14, by means previously described, to draw exudate from wound 22 through channels and apertures of bandage member 28, packing and film, splitter tube and evacuating tube 32 to be deposited in canister 38. The negative pressure applied to wound 22 created by pump 110 can be applied for a period of time as determined by the caregiver. After a period of drawing, the caregiver may deactivate the negative pressure.

Apparatus 10 is a portable, easy to use topical system that is intended to provide a protective/occlusive environment with features to facilitate the administering of standard wound care. Apparatus 10 provides for the care of two independently controlled wounds. Apparatus 10 provides negative pressure to the wound bed 22, and the caregiver can set the level of negative pressure. Illustratively, the negative pressure is variable from 25-mmHg to 225-mmHg at increments of 10-mmHg. The caregiver can choose between continuous, intermittent (profile), and no negative pressure modes. It will be appreciated that apparatus 10 may be set up to provide various levels of vacuum at various times. Apparatus 10 controls the rate of negative pressure change to reduce discomfort to patient. Apparatus 10 may be provided with the ability to pause negative pressure therapy for set durations of time. The system may be set up to provide audible alarms to remind the caregiver to reset or start a new cycle of vacuum therapy.

The apparatus 10 is intended to provide an occlusive wound healing environment. The apparatus 10 provides an active therapy unit that delivers drainage and cleansing for aggressive wound healing. It is intended, for example, for use on all pressure ulcers (Stage II through Stage IV), surgical draining wounds and leg ulcers.

The controller 20 disclosed herein regulates the functions of a vacuum therapy apparatus that provides negative pressure to the wound bed 22 of a patient 26. The level of negative pressure can be set by a caregiver using a caregiver interface 18 in a range from 25-mmHg to 225-mmHg in increments of 10-mmHg. The controller 20 implements a proportional, integral, derivative ("PID") 302 control algorithm and pulse width modulation ("PWM") 304 to adjust the negative pressure applied to the bandage 28 to the setpoint level.

The caregiver can choose between continuous, no negative pressure, and intermittent (profile) modes using the caregiver interface 18. In continuous mode, the caregiver selects a desired negative pressure value from the range provided by the system. The desired negative pressure value or setpoint is reached by controlling the rate of change of negative pressure. Once the setpoint is reached, negative pressure approximately equal to the setpoint is applied to the wound bed 22 until interrupted. As the name implies, in the no negative pressure mode, no negative pressure is applied to the wound bed 22. In the profile mode, the controller 20 regulates the negative pressure provided to the wound bed site 22 between two caregiver selected negative pressure values in cycles.

Illustratively, the second negative pressure value during profile mode is less than the first negative pressure value and has a value between 25-mmHg and 10-mmHg less than the first caregiver negative pressure value. The difference between the first and second caregiver determined negative pressure values is set in increments of 10-mmHg when the range for the first caregiver determined negative pressure value is variable between 35-mmHg and 225-mmHg in 10-mmHg increments. Illustratively, the first caregiver determined negative pressure value is activated for ten minutes and the second caregiver determined negative pressure value is activated for three minutes during profile mode.

During initiation or termination of any mode, and during transition between cycles of profile mode, the controller 20 regulates the rate of change of the negative pressure applied to the wound bed 22 to provide a gradual increase or decrease in negative pressure. Thus the rate of change of the negative pressure applied to the wound bed 22 is controlled.

The vacuum subsystem 66 regulates negative pressure applied to a wound dressing 28. Pressure is regulated by a proportional valve 130 under microprocessor 320 control. The proportional valve 130 controls pressure by restricting flow. The microprocessor 320 controls valve position by applying a PWM signal 306 to the solenoid of the proportional valve 130. The PWM signal 306 induces the solenoid to open and close the valve rapidly and as a result of hysteresis and time averaging of the open periods an average position or constriction is approximated.

Vacuum pressure transducer 124 provides feedback to microprocessor 320. The output of the transducer 124 is amplified and filtered to remove high frequency noise such as pump oscillations The resulting voltage is proportional to wound vacuum pressure. The voltage is converted by a 12-bit analog to digital converter ("ADC") 310 sampled at 100 Hz.

Microprocessor 320 implements a PID control algorithm 302 to adjust the duty cycle of a PWM signal 306 to the solenoid of the proportional valve 130 until the setpoint pressure is achieved. The rise (or fall) time of a system controlled using PID control of a PWM driving signal inherently includes some aspect of control over the rate of change of the controlled parameter. This inherent control is dependent upon the proportional, integral and differential gains implemented in the PID controller 302. However, the disclosed controller further limits and controls the rate of change of negative pressure by filtering the control signal with a filter 308 implemented in the micro-controller 320 to ensure that the rate of change of negative pressure does not exceed a desired value. Thus, the actual negative pressure over the wound bed 22, indicated by the transducer signal, is raised or lowered slowly to the setpoint.

In the illustrated embodiment, the vacuum therapy device 10 includes a vacuum source 110, a vacuum bandage 28, a regulator, a pressure transducer 124, setpoint circuitry 312, and a controller 20. Vacuum source 110 is fluidly coupled through line to vacuum bandage 28. Illustratively, pressure transducer 124 is positioned to sense the air pressure above a wound bed 22 over which vacuum bandage 28 is affixed. Pressure transducer 124 provides a pressure signal indicative of the air pressure adjacent the wound bed 22. Setpoint circuitry 312 provides a setpoint signal indicative of the desired air pressure above the wound bed 22. Setpoint circuitry 312 is incorporated into graphical user interface 18. Controller 20 is coupled to setpoint circuitry 312, pressure transducer 124, and regulator 130. Controller 20, in response to the setpoint signal and the pressure signal, controls regulator 130 to adjust the air pressure adjacent the wound bed 22.

As mentioned above, illustratively, controller 22 controls regulator 130 so that the air pressure adjacent the wound bed 22 ultimately is equal to, or substantially equal to, the desired pressure. Regulator 130 is controlled by controller 20 so that the rate of change of the air pressure adjacent the wound bed 22 is within desirable limits. In this manner, the air pressure adjacent the wound bed 22 is adjusted in a controlled fashion until the desired air pressure is achieved. By limiting the rate of change of the air pressure adjacent the wound bed 22, discomfort to a patient 26 receiving vacuum wound therapy is reduced.

Controller 20 is implemented on a microprocessor 320 programmed to run a control algorithm implementing the PID controller 302, a filter 308, and PWM signal generator 304. The program resident on the microprocessor 320 also runs other algorithms. The software consists of foreground and background tasks. The foreground tasks occur in an interrupt handler every 10 msec. Control of the vacuum is performed entirely in the foreground, while screen display and other items, such as BIT are done in background.

Illustratively, microprocessor 320 is a 68332 microcontroller with internal timer. Every 10 msec when the 68332 internal timer expires the ADC 310 is set up to read the analog input values. When it has read them all another interrupt goes off to inform the software. This interrupt handler takes the value from the ADC 310 and converts it to a pressure by utilizing a scale factor and an offset. The scale factor and offset are computed by using the calibration value for zero pressure (read at startup) and the factory stored calibration value for 225 mmHg.

The desired pressure set by the user and the pressure read from the ADC 310 provide the inputs for the control loop. However, the desired pressure does not immediately correspond to the user set value. Instead it slowly ramps up so as to avoid a sudden change that may cause discomfort for the patient. The desired pressure is computed by determining the elapsed time since the pressure was set and computing a delta value such that the pressure changes no more than 7.5 mmHg per second. For example, if the pressure at zero seconds is zero mmHg and the setpoint pressure is 125 mmHg, then the desired pressure is 7.5 mmHg after one second, 15 mmHg after two seconds, etc. The desired pressure is recomputed with each iteration of the control loop; i.e., every 10 msec so that each iteration increases the desired pressure by 0.075 mmHg.

The proportional valve 130 setting is controlled by adjusting the duty cycle of a 5 kHz square wave on the output of a TPU pin from the microcontroller 320. The setting, adjusted every 10 msec, is the result of an experimentally derived offset for the proportional valve 130 (the point at which the vacuum begins to operate) plus a proportional term and a integral term.

The proportional term is the result of the proportional gain (experimentally derived, currently set to 2) times the error signal where the error signal is the desired pressure minus the pressure read.

The integral term is the result of the integral gain (experimentally derived, currently set to 0.5) times the running sum of the error signal maintained across all iterations of the control loop. The integral term is not updated whenever the proportional valve 130 is at the maximum and the pressure is still too low or if it is at the minimum proportional valve setting and the pressure is still too high. This helps keep the integral term from causing the pressure to overshoot the target excessively. Whenever the pressure goes to zero, the integral term is reset.

The software is also set up to allow for a derivative term but the gain for this was experimentally chosen to be 0, so it no has effect on the control loop. It is within the teaching of the disclosure to implement any of the various methods available for the determination of proper gain constants for implementation of a PID control algorithm and such methods will likely provide a value for the derivative gain.

Mathematically, the described control algorithm can be represented as follows:

cal lo is read at startup to the adc 310 value when pressure is 0 mmHg
cal hi is set at the factory to the adc 310 value when pressure is 225 mmHg
cal range=cal hi-cal lo
pressure read=((raw input from adc-cal lo)*225)/cal range
delta t=elapsed timer ticks since pressure was changed (due to user, profile mode, alarm, etc)
delta p=(7.5 mmHg*delta t)/100 ticks per second
pressure desired=pressure set+/-delta p(+/- depending on whether pressure is being increased or decreased)
pressure desired is constrained so as to not allow it to overshoot pressure set
error signal=pressure desired-pressure read
prop term=PROP GAIN*error signal
if proportional valve 130 is at the maximum and the pressure is still too low, or if proportional valve 130 is at its minimum setting and the pressure is still too high, skip integral sum. otherwise,
integral sum integral sum+error signal
integral term=INT GAIN*integral sum
proportional valve output value=STARTUP OFFSET+ prop term+integral term An exemplary computer program written in C programming language to implement the PID control algorithm 302 and filter 308 to control the pressure adjustment is set forth below:

```
Drainset[WOUND1]
    .min_press_set=DEFAULT_MIN_PRESS;
Drainset[WOUND1].state=VAC_INIT;
Drainset[WOUND2].mode=MODE_OFF
Drainset[WOUND2].pause_time=0;
Drainset[WOUND2].press_set=DEFAULT_PRESSURE;
Drainset[WOUND2].
    min_press_set=DEFAULT_MIN_PRESS;
Drainset[WOUND2].state=VAC_INIT;
Drainage_timer_id[WOUND1]=NULL_TIMER_ID;
Drainage_timer_id[WOUND2]=NULL_TIMER_ID;
Pressure_read[WOUND1]=Pressure_set[WOUND1]=0;
Pressure_read[WOUND2]=Pressure_set[WOUND1]=0;
Pvalve_set[WOUND1]=0;
Pvalve_set[WOUND2]=0;
Profile_cnt[WOUND1]=0;
Profile_cnt[WOUND2]=0;
Time_clogged[WOUND1]=Time_loose[WOUND1]=0;
Time_clogged[WOUND2]=Time_loose[WOUND2]=0;
Integral_term[WOUND1]=0;
Integral_term[WOUND2]=0;
Last_error_signal[WOUND1]=0;
Last_error_signal[WOUND2]=0;
//for control loop
GAIN1=2;
GAIN2=0;
GAIN3=0;
}
/*********************************************
* FUNCTION :GetDrainage
* INPUTS :wid—Wound ID to get data for
* OUTPUTS :dval—Current settings for drainage.
* DESCRIPTION :Returns current drainage setting for
    specified wound.
*********************************************/
void GetDrainage(int wid, DRAINSET*dval)
{
WORD errcode;
if ((wid<WOUND1)||(wid>NOWOUND))
{
#ifndef_WINDOWS
#include "ascii.h"
#endif
#define PROFILE_CYCLE 13 // 10 minutes at max, 3 at min
#define PROFILE_MAX_MINUTES 10
#define SEC30 (TICKS_PER_SEC *30L)
#define PRESS_CHANGE 7 // max change 0.7 mmHg/100
    msec=>7 mmHg/sec (TBD want 7.5).
/*LITERALS & CONSTANTS*/
/*EXTERNAL PROCEDURES*/
/*INTERNAL & PUBLIC VARIABLES*/
STATIC DRAINSET Drainset[2]; // current drainage settings for each wound.
STATIC int Drainage_timer_id[2]; //timer id for drainage pause for each wound.
STATIC int Pressure_read[2]; // Most recent pressure readings
STATIC int Pvalve_set[2]; // Most recent prop. valve setting
STATIC int Pressure_set[2]; // Most recent pressure desired
STATIC WORD Profile_cnt[2]; // ticks in minutes since profile mode started
STATIC DWORD Time_clogged[2]; //timer value when clog detected
STATIC DWORD Time_loose[2]; //timer value when loose detected
STATIC int Integral_term[2]; // for integral control of prop. valve
STATIC int Last_error_signal[2]; // for derivative control of prop. valve
//for control loop, all values TBD
STATIC int GAIN1;
STATIC int GAIN2;
STATIC int GAIN3;
/*INTERNAL PROCEDURES*/
STATIC void AdjustPressure(int wid, int press);
#ifndef_WINDOWS
#pragma region("code=code")
#endif
/*********************************************
*FUNCTION :InitVacuum
*INPUTS :none
*OUTPUTS :none
*DESCRIPTION :Initialize ad vacuum variables
*********************************************/
void InitVacuum( )
{
Drainset[WOUND1].mode=MODE_CONTINUOUS;
Drainset[WOUND1].pause_time=0;
Drainset[WOUND1].press_set=DEFAULT_PRESSURE;
```

Execution of the above program by illustrative wound treatment apparatus 10 controls the rate of change of the negative pressure applied to the wound of the patient. The input parameters to the computer program include the desired pressure and an identification code for the wound to which the pressure is to be applied. Those skilled in the art will recognize that proper operation of the computer program requires access to the memory location in which the most recent digitally converted reading of the pressure read by the pressure transducer 124 has been stored.

The computer program first checks to ensure that a legitimate wound is identified as the wound to which the pressure is to be applied. If an appropriate wound is not identified, the function sends an error message to the user interface stating that an invalid wound has been identified. If an appropriate wound is identified, then the pressure error signal is calculated by using the most current pressure reading from the desired pressure. The function next determines if the desired pressure is attainable, i.e., if the maximum allowable pressure has already been reached and is still lower than the desired pressure or the minimum allowable pressure has been reached and the current pressure is still higher than the desired pressure. If either of these situations exists the integral term of the PID controller 302 is not updated. If neither of these situations exists, the integral term is updated by adding the current error term to the accumulated sum of error terms since the last reset of the integral term. The derivative term of the PID controller 302 is then calculated by subtracting the last value of the pressure error from the current value of the pressure error. The current value of the pressure error is then stored as the last value of the pressure error for use in the next loop.

Finally, the PID control 302 is implemented to provide an unfiltered output value for the duty cycle of the pulse width modulator. If the desired pressure is zero, the unfiltered output value for the duty cycle of the pulse width modulator 304 is set to zero. Otherwise, the unfiltered output value for the duty cycle of the pulse width modulator 304 is set to the sum of the last output value, the error signal times the proportional gain, the integral value times the integral gain, and the derivative value times the derivative gain. The unfiltered output value is then filtered to ensure that the output to the PWM does not induce a pressure change greater than the maximum allowable pressure change in any direction.

In the detailed descriptions that follow, several integrated circuits and other components are identified, with particular circuit types and sources. In many cases, terminal names and pin numbers for these specifically identified circuit types and sources are noted. This should not be interpreted to mean that the identified circuits are the only circuits available from the same, or any other, sources that will perform the described functions. Other circuits are typically available from the same, and other, sources which will perform the described functions. The terminal names and pin numbers of such other circuits may or may not be the same as those indicated for the specific circuits identified in the application.

Figure 6:
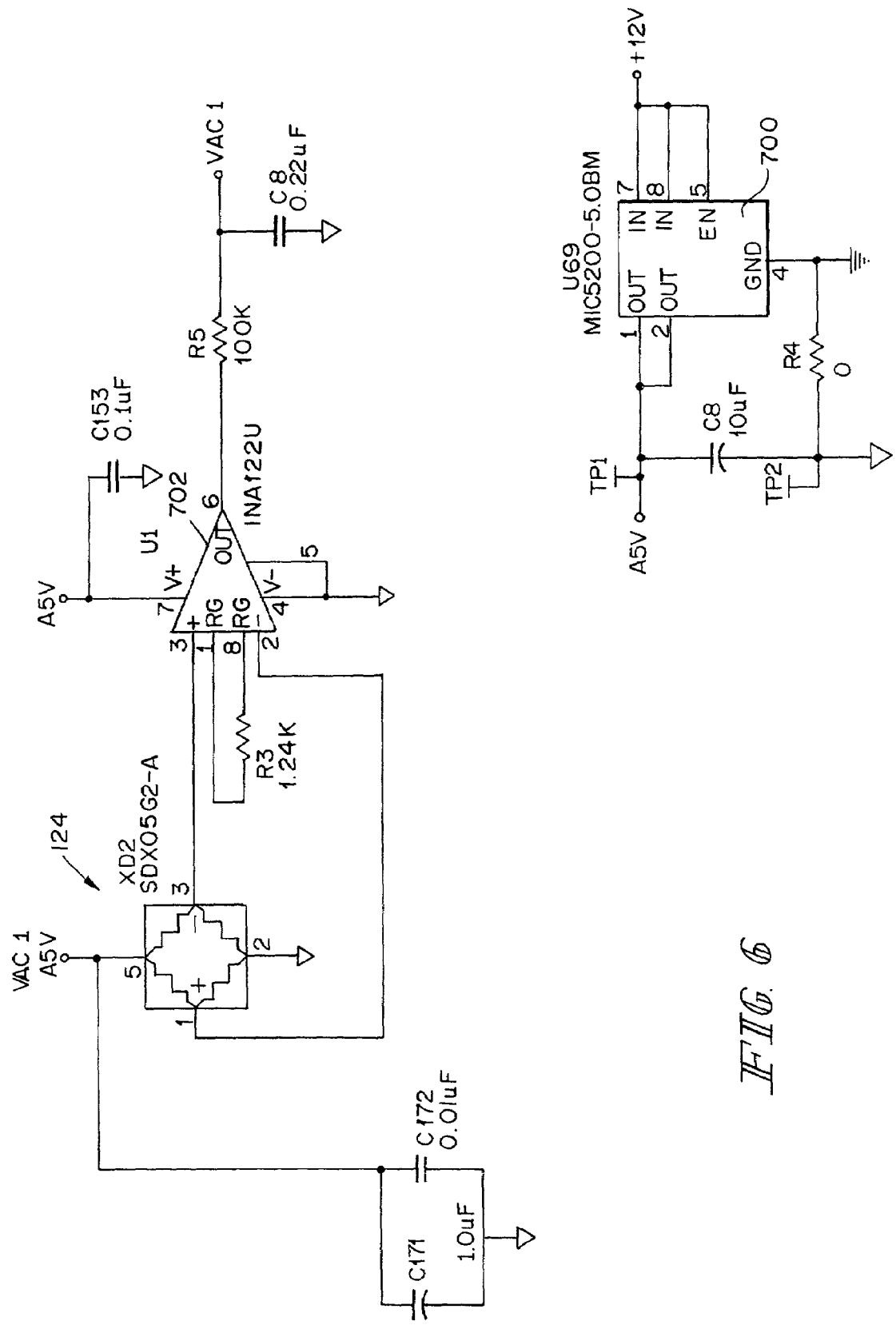

Turning now to FIG. 6, the pressure sensor circuitry for pressure transducer 124 is shown. As mentioned above, apparatus 10 has two parallel system circuits for sensing pressure in two different waste collection canisters 38, 39. Thus, the description below of circuitry associated with sensing pressure in one of canisters 38, 39 is applicable to both unless specifically noted otherwise. Pressure transducer 124 is illustratively a Sensyn SDX05G2-A pressure transducer, although other pressure transducers may be used, such as Motorola MPX5050GVP integrated pressure sensor.

A supply voltage terminal, pin 5, of pressure transducer 124 is coupled to a pair of OUTput terminals of a voltage regulator 700, illustratively a MIC5200 Low-Dropout Regulator. The OUTput terminals of voltage regulator 700 are also coupled to the V+ terminal of a differential amplifier 702 such as, for example, a Burr-Brown type INA122U low power instrumentation amplifier. Pin 5 of pressure transducer 124 is also coupled through a capacitance of about 11 microfarads (μF) to ground. Pin 2 of pressure transducer 124 is also coupled to ground. Output pin 1 of pressure transducer 124 is coupled to the inverting input terminal (−) of amplifier 702. Output pin 3 of pressure transducer 124 is coupled to the non-inverting input terminal (+) of amplifier 702.

V− and Ref terminals of amplifier 702 are coupled to ground. A 1.24 kilohm (Kohm) gain adjusting resistor is coupled across the RG terminals of amplifier 702. An output terminal, pin 6, of amplifier 702 is coupled through a 100 Kohm resistor to a VAC1 line. The VAC1 line is also coupled to ground through a 0.22 μF capacitor. A GrouND terminal of voltage regulator 700 is coupled to ground. INput and ENable terminals of voltage regulator 700 are coupled to +12V.

Figure 7A:
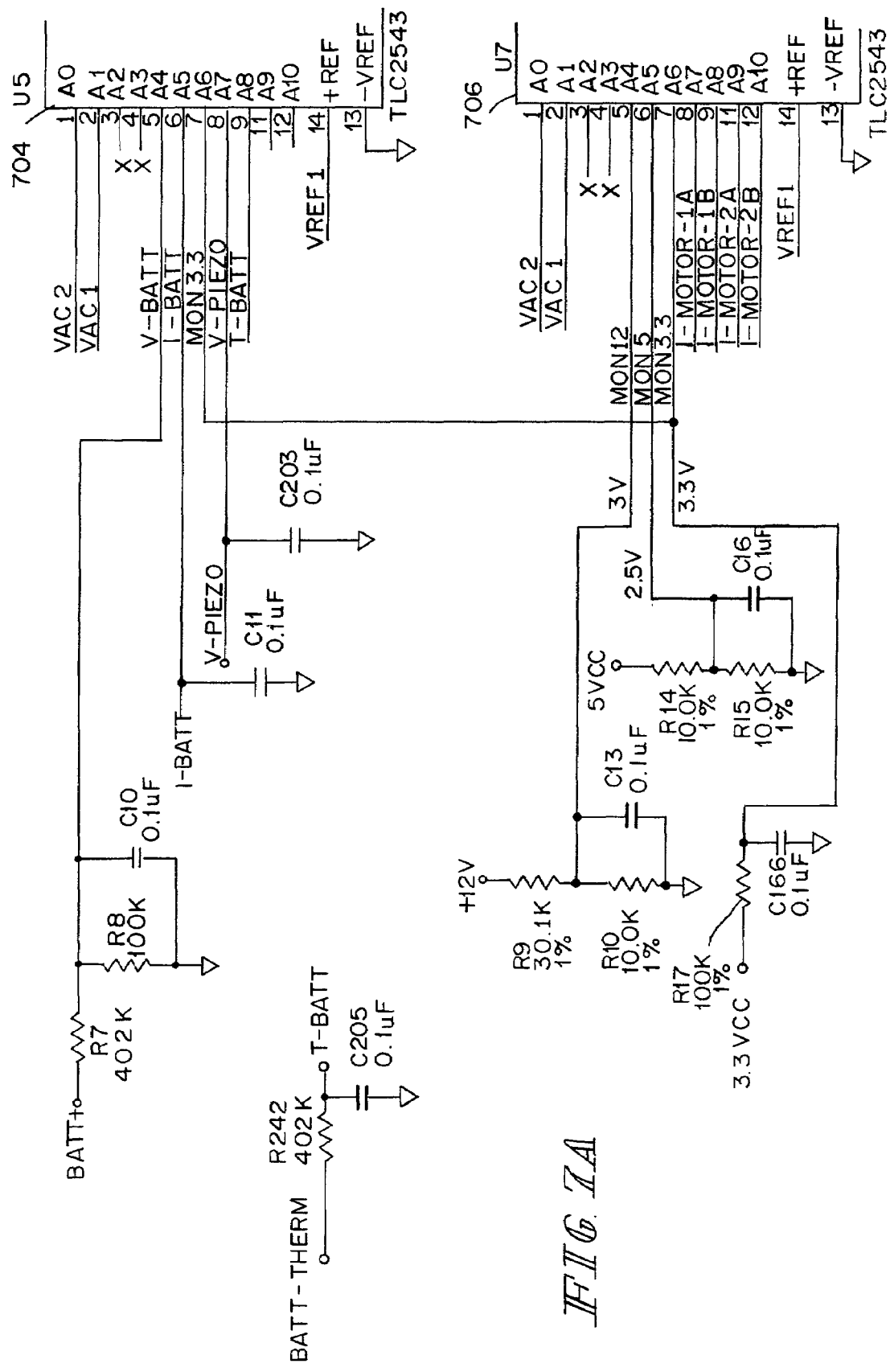
Figure 7B:
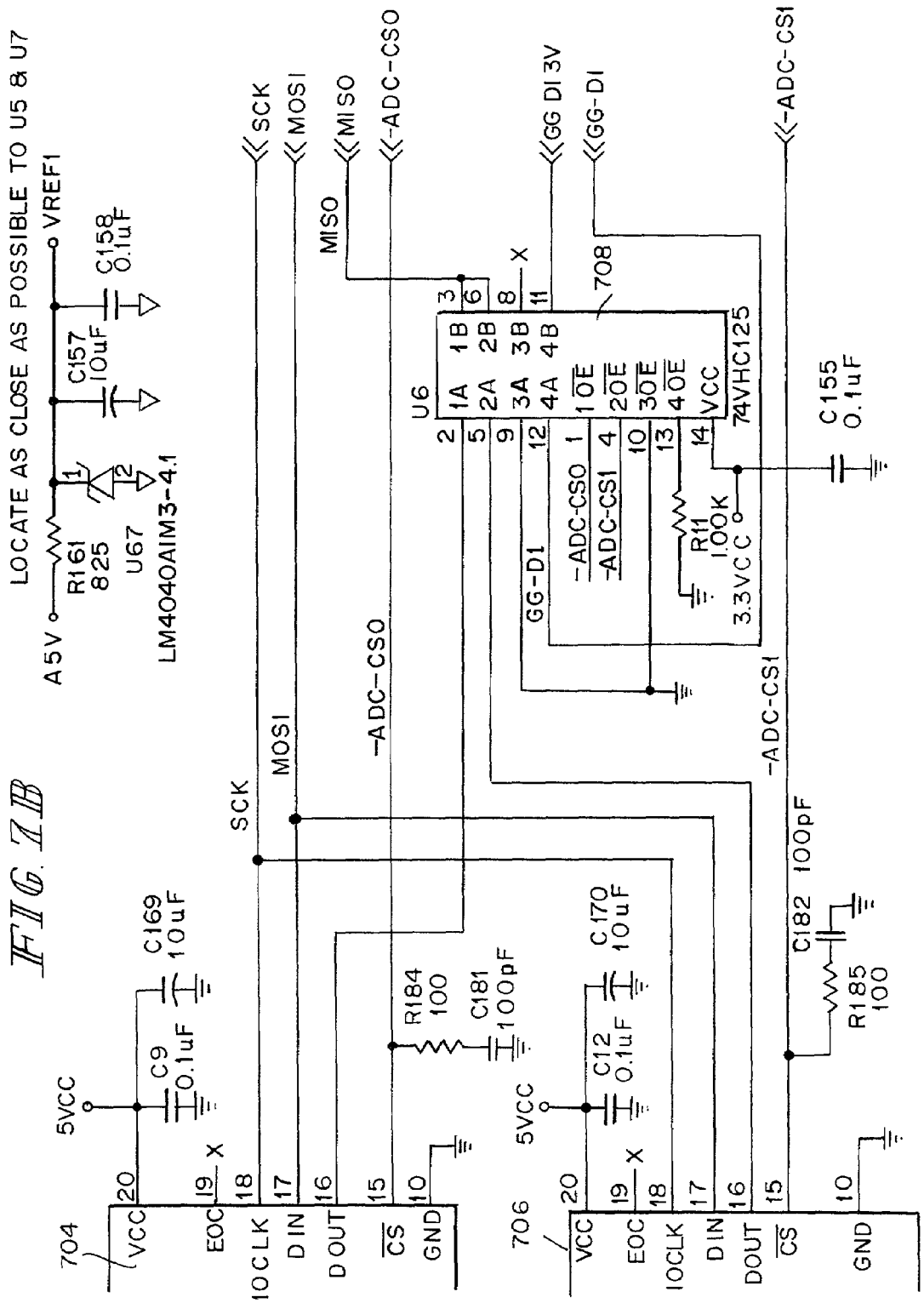
Figure 8C:
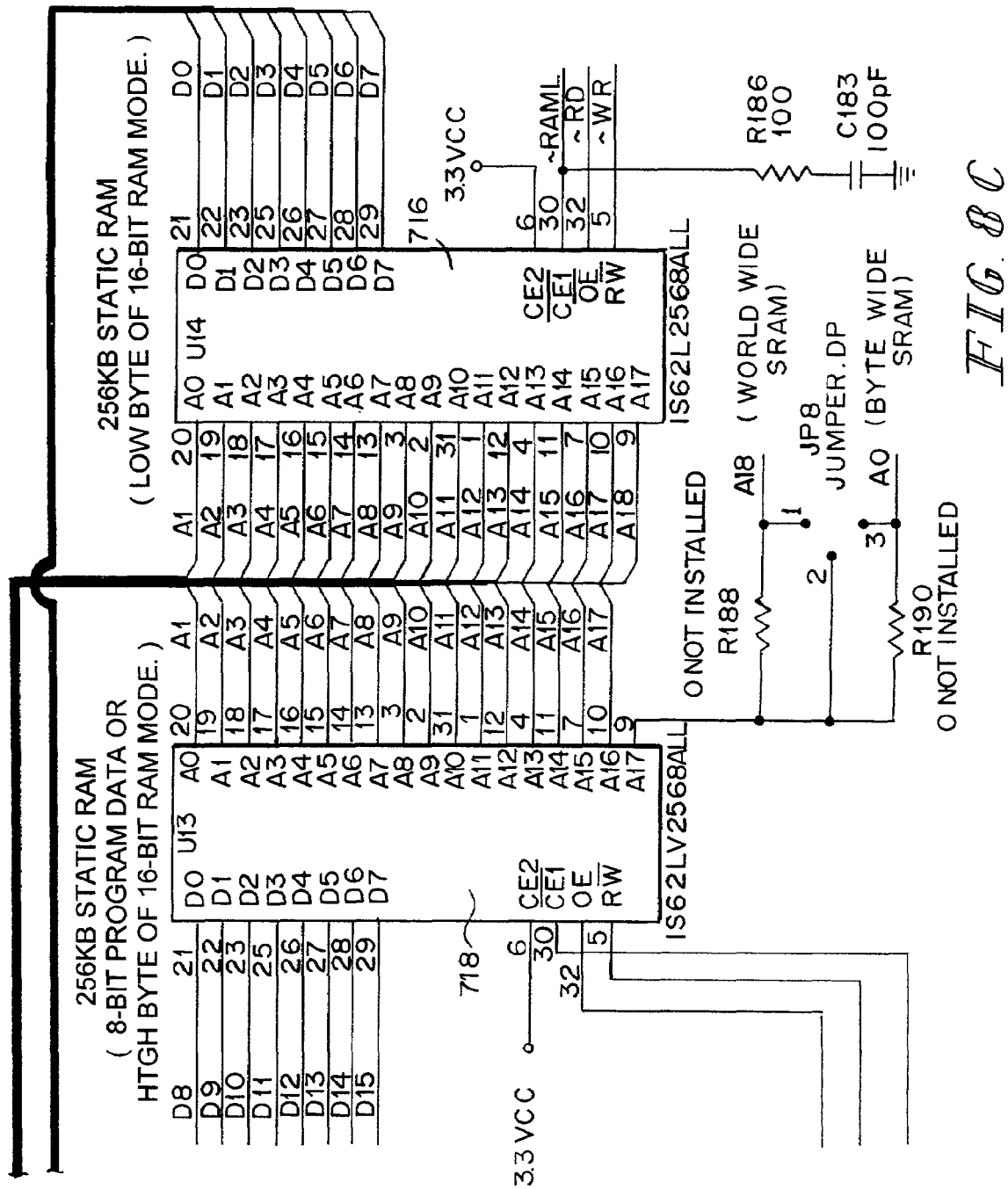
Figure 8D:
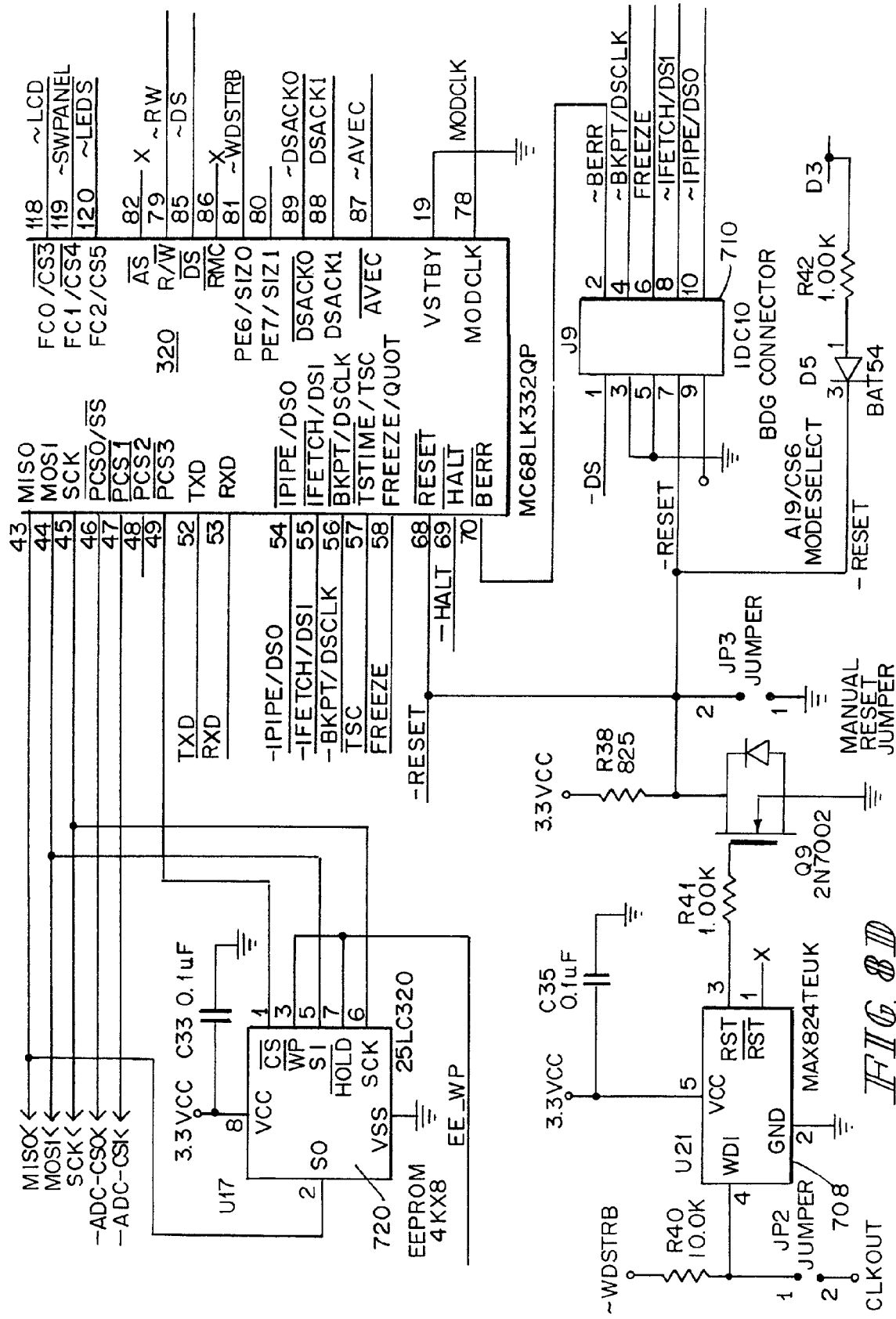
Figure 8E:
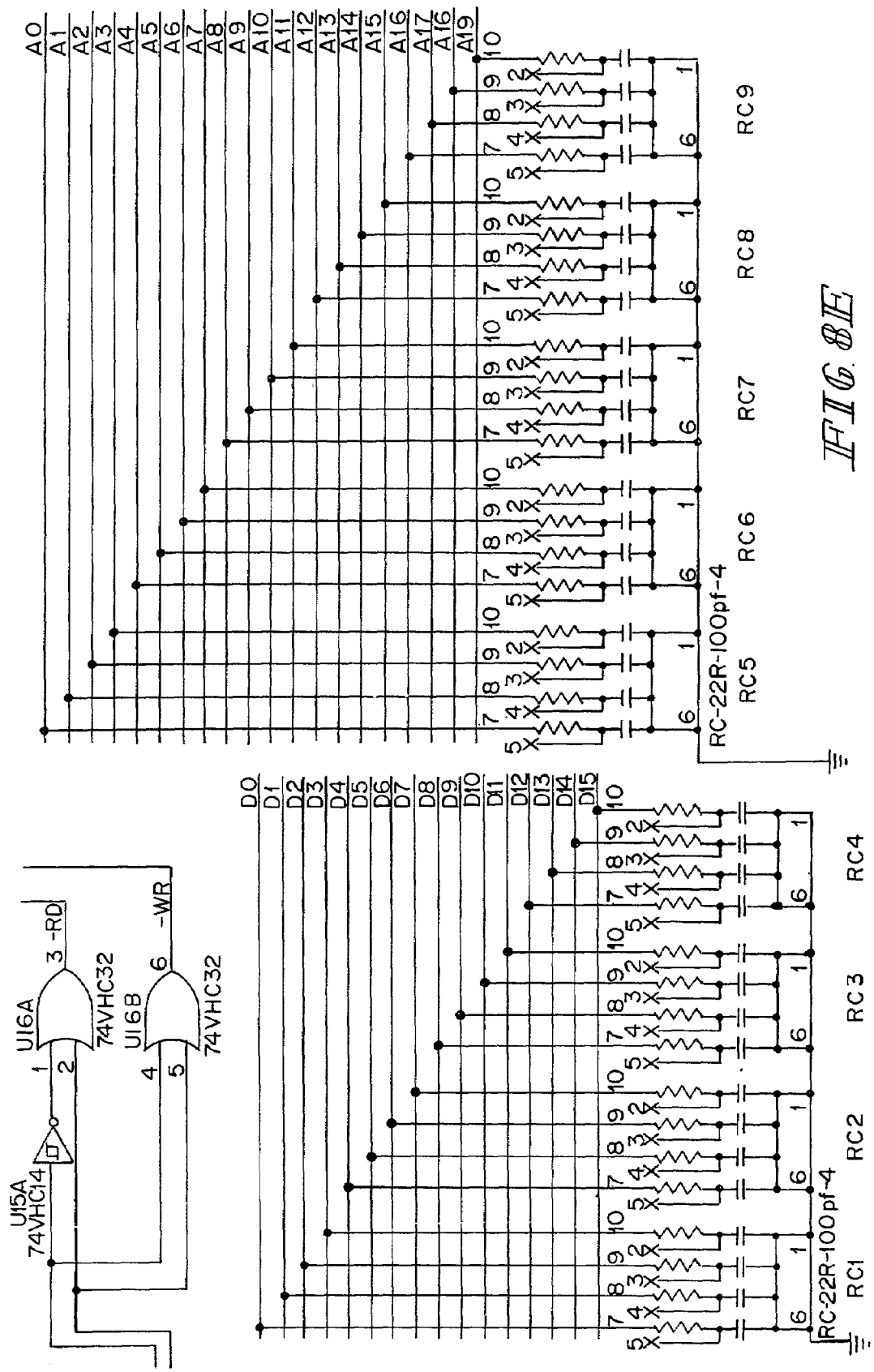
Figure 9:
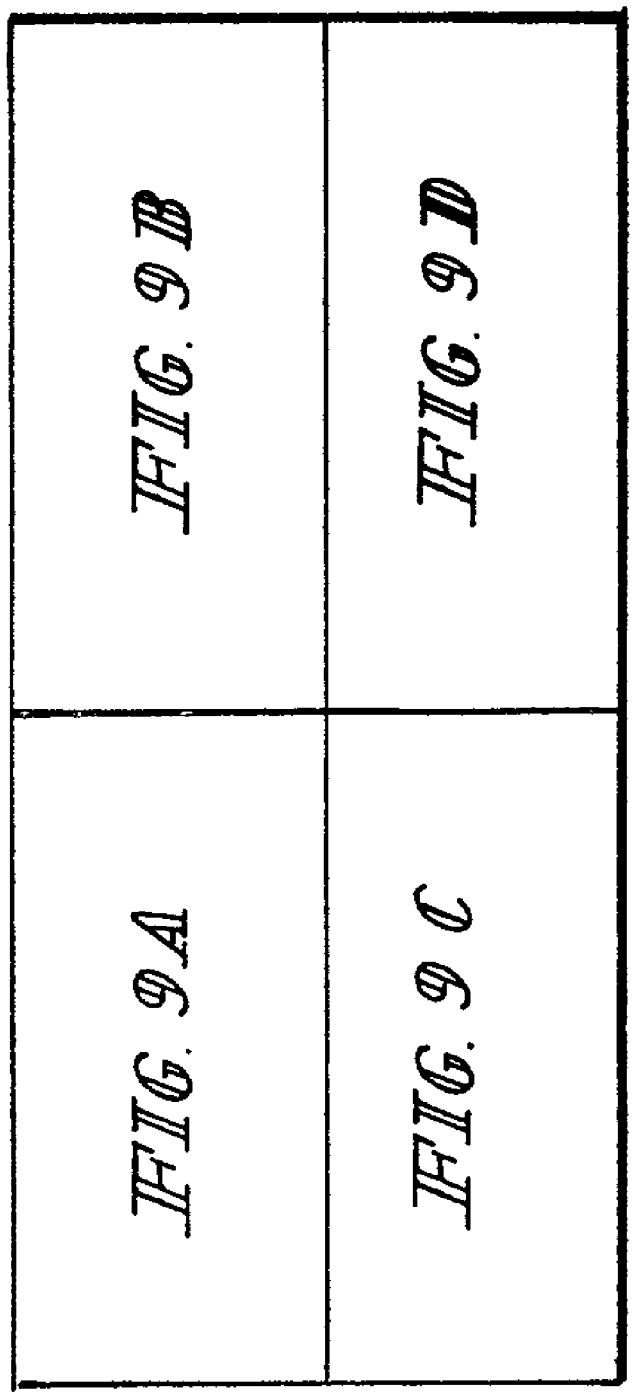
Figure 9C:
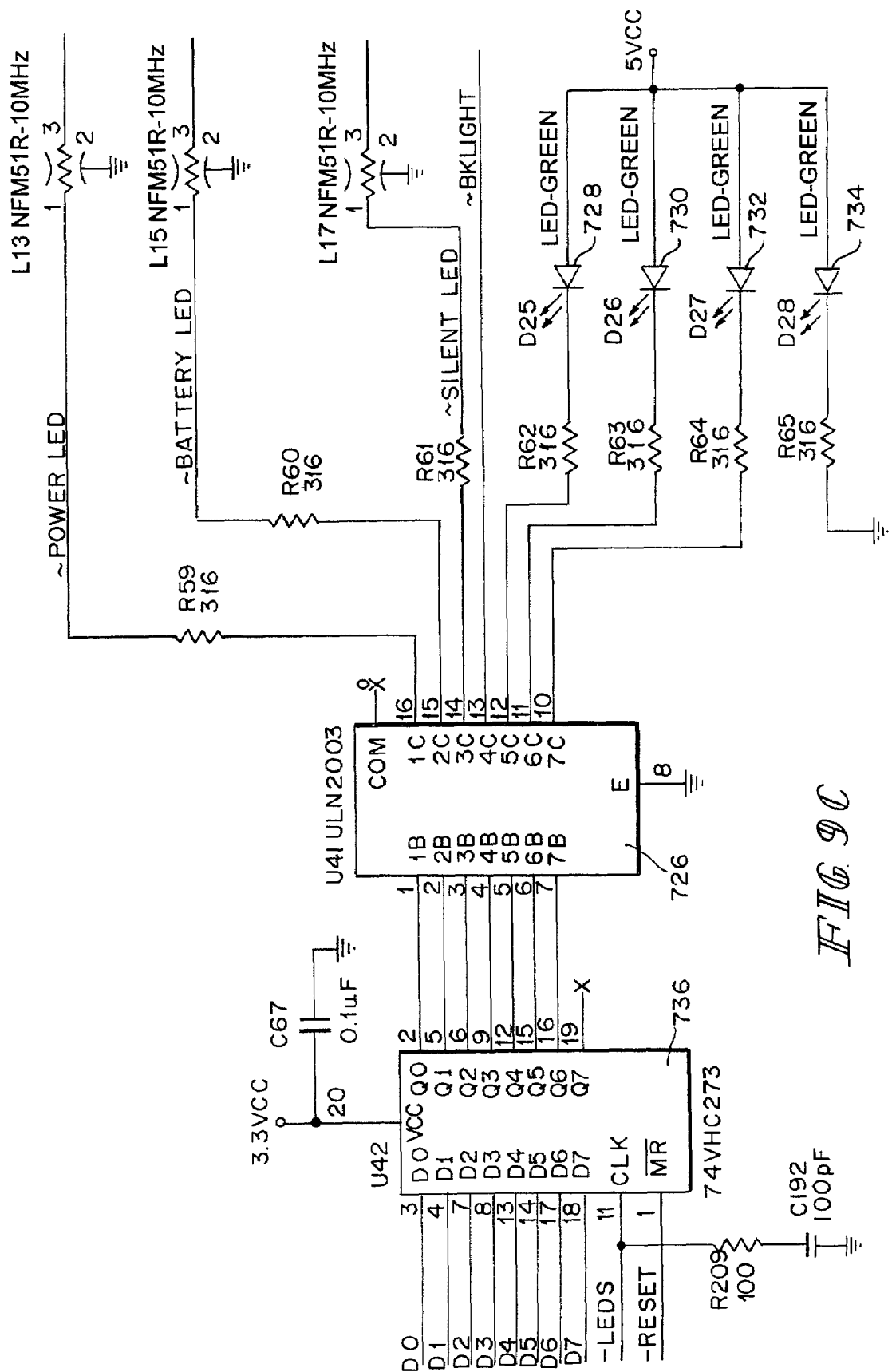
Figure 9D:
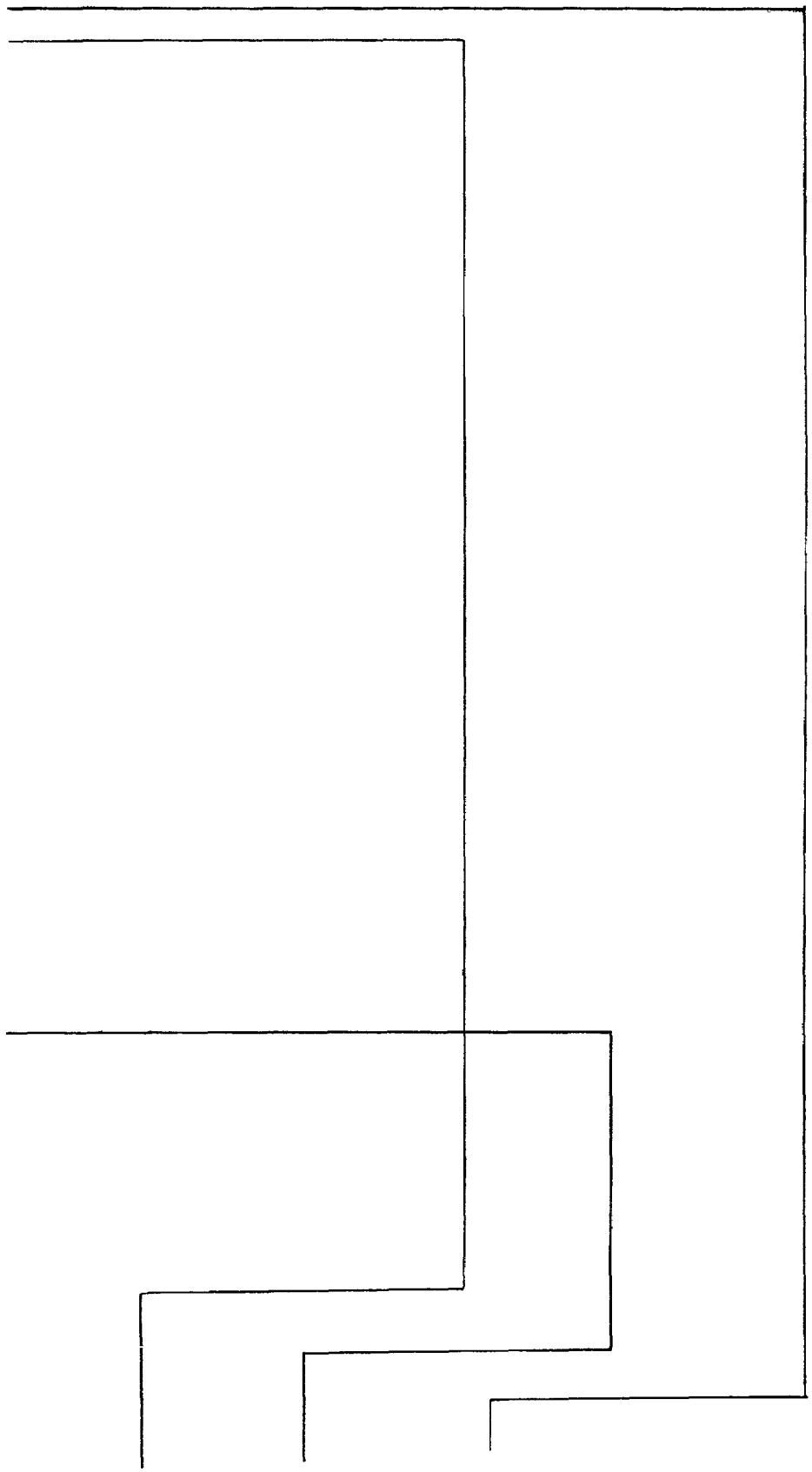
Figure 10:
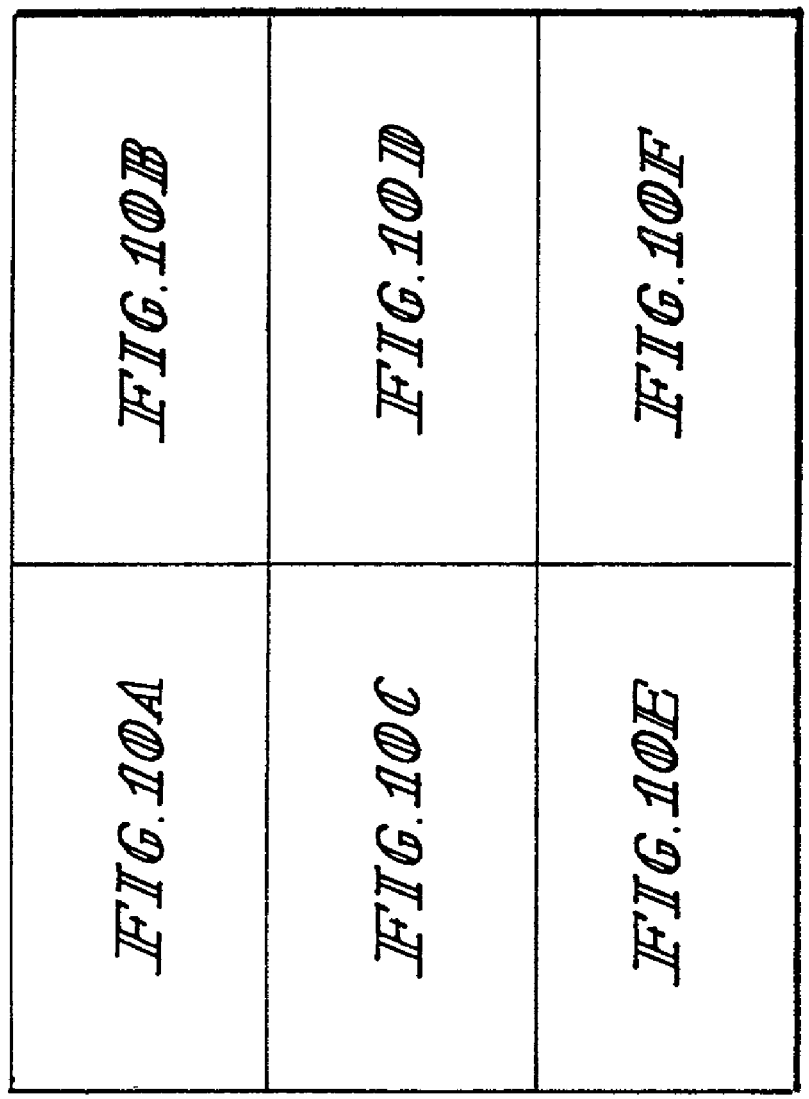
Figure 10A:
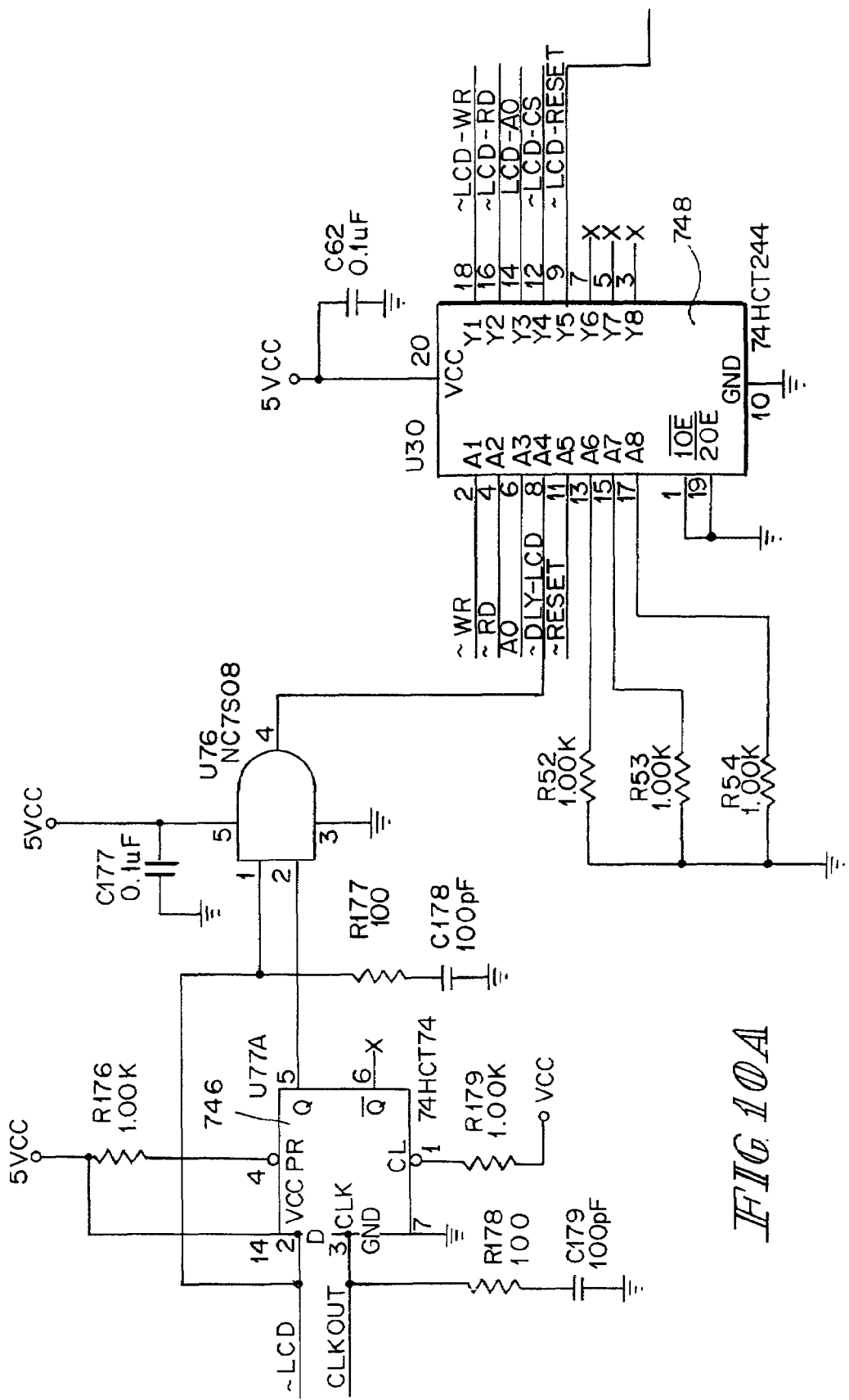
Figure 10B:
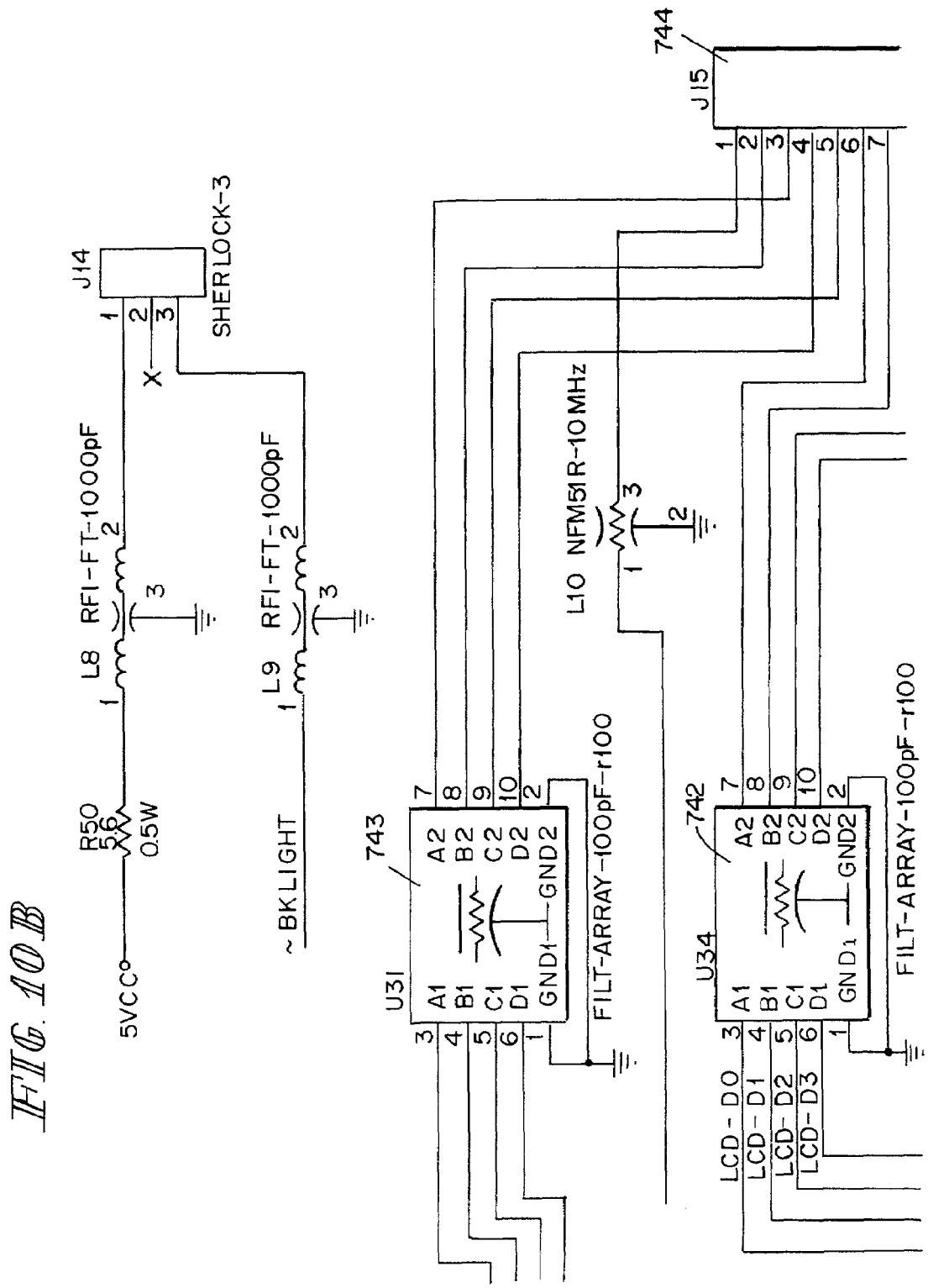
Figure 10D:
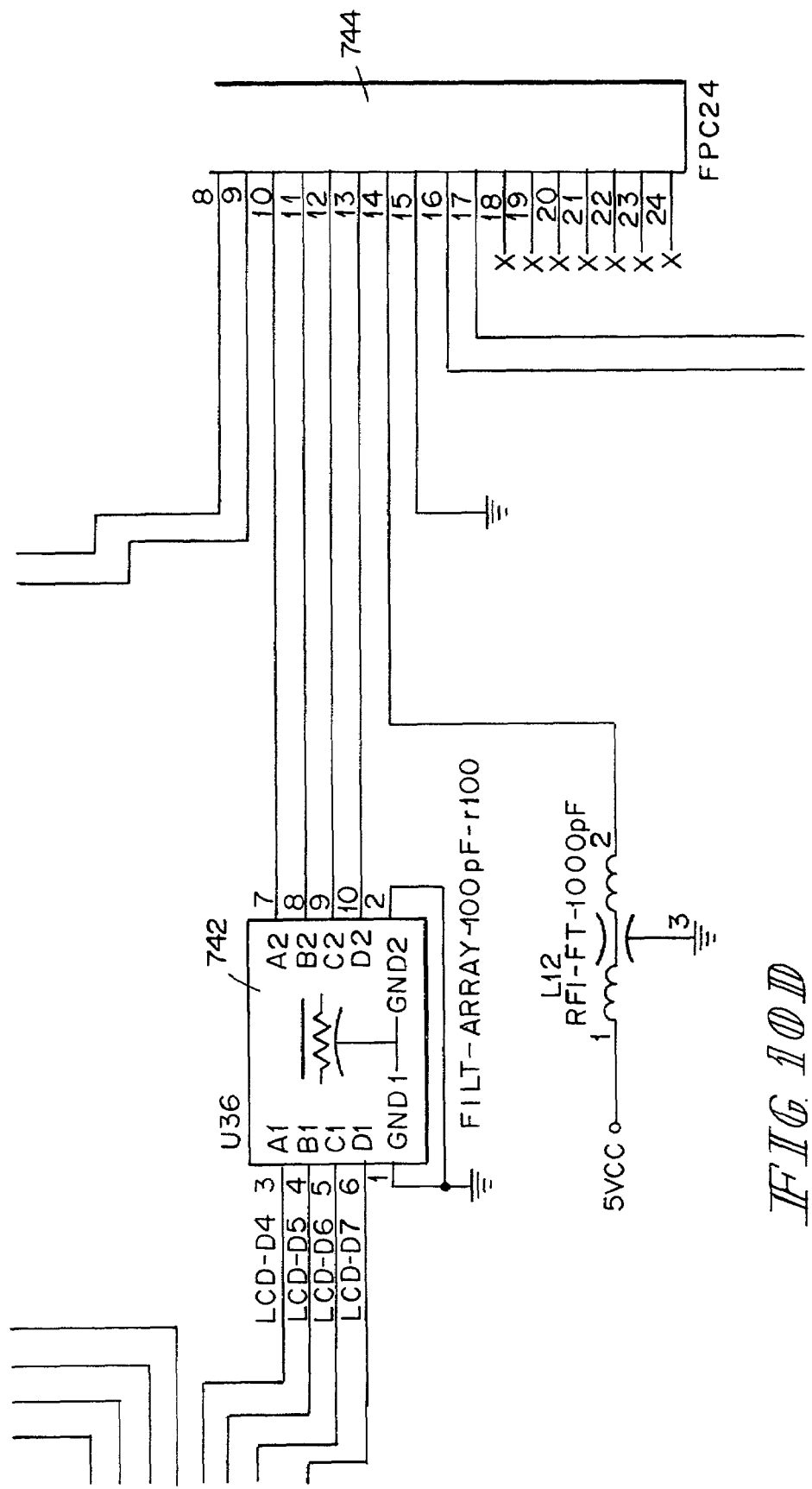
Figure 10E:
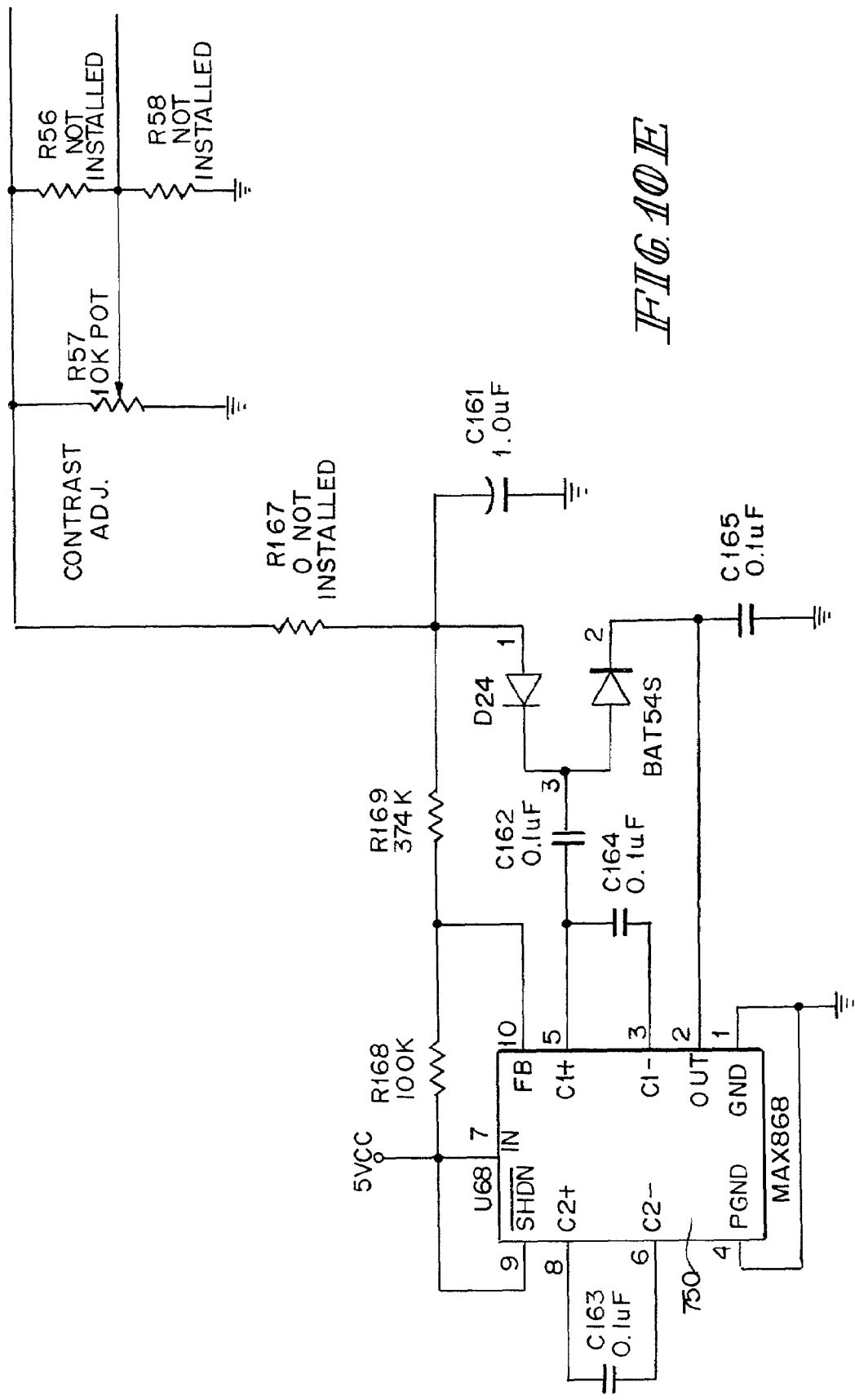
Figure 10F:
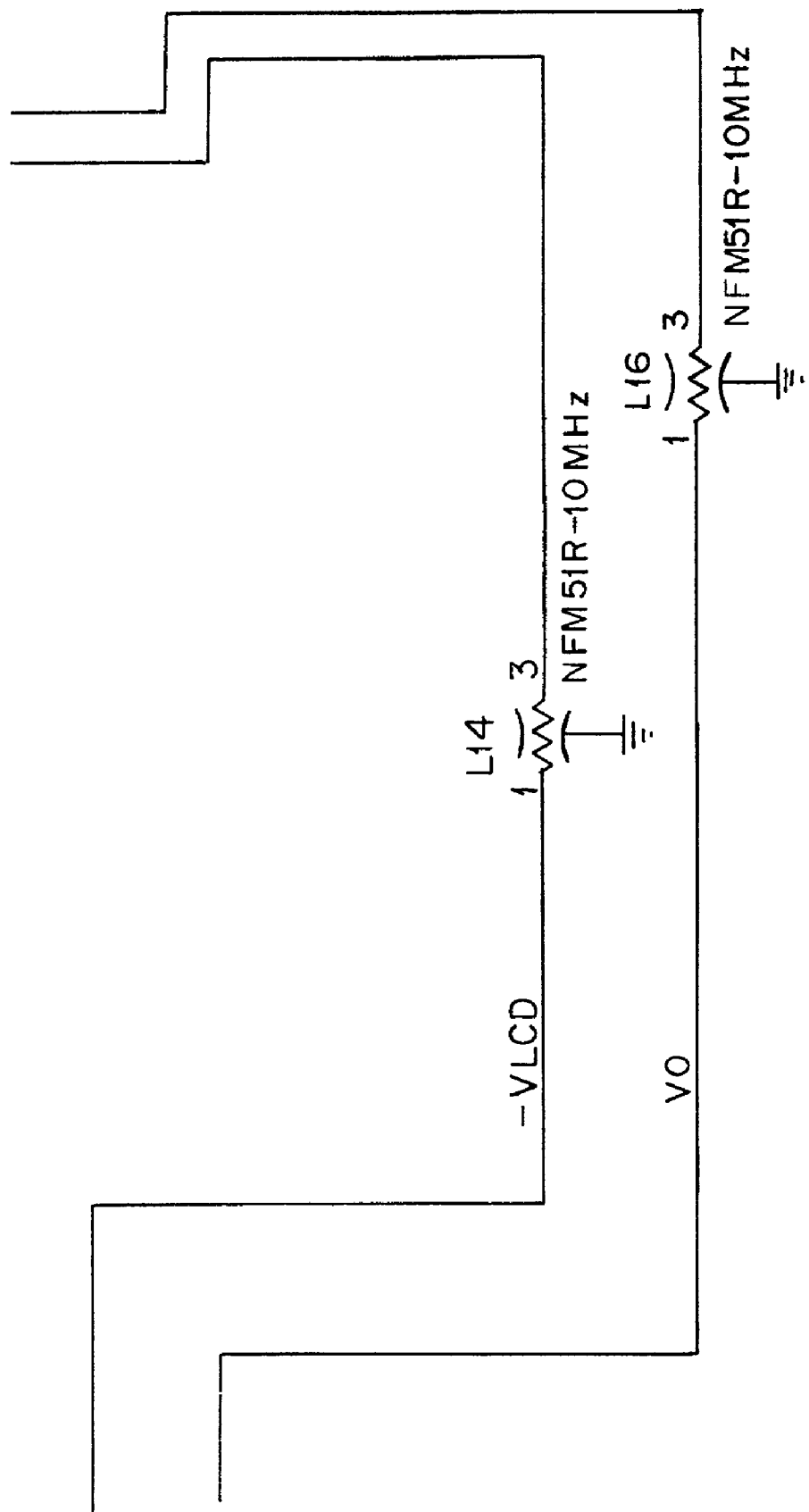

Referring now to FIGS. 7A–7B, the VAC1 line is coupled to an input terminal, A1, of each of two analog-to-digital converters (A/Ds) 704, 706. A/Ds 704, 706 illustratively are Texas Instruments TLC2543 A/Ds. A VAC2 line from pressure transducer 229 is coupled respective the A0 input terminals of A/Ds 704, 706. A GrouND terminal and a −REFerence terminals of each A/D 704, 706 are coupled to ground. The system VoltageREFerence1 line is coupled to +REFerence terminals of both A/Ds 704, 706. The system VREF1 line is also coupled to ground through a capacitance of about 10 μF and a 4.1 volt Zener diode. The system VREF1 line is also coupled to the system A5V line through an 825 ohm resistor.

The voltage supply terminals, VCC, of both A/Ds 704, 706 are coupled to the system 5VCC line and also coupled to ground through a capacitance of about 10 μF each. The system V-BATTery line, I-BATTery line, MONitor3.3 line, V-PIEZO line, T-BATTery line, MONitor12 line, MONitor5 line, MONitor3.3 line, I-MOTOR-1A line, I-MOTOR-1B line, I-MOTOR-2A line, and I-MOTOR-2B line are coupled to terminals A4 of A/D 704, A5 of A/D 704, A6 of A/D 704, A7 of A/D 704, A8 of A/D 704, A4 of A/D 706, A5 of A/D 706, A6 of A/D 706, A7 of A/D 706, A8 of A/D 706, A9 of A/D 706, and A10 of A/D 706, respectively.

The system V-BATT line is coupled to ground through a parallel R-C network consisting of a 0.1 μF capacitor and a 100 Kohm resistor. The V-BATT line is also coupled to the system BATTery+ line through a 402 Kohm resistor. The system T-BATT line is coupled to ground through a 0.1 μF capacitor and to the system BATTery-THERMal line through a 402 Kohm resistor. The system MON12 line is coupled to ground through a parallel combination of a 0.1 μF capacitor and a 10 Kohm resistor. The MON12 line is also coupled to the system +12 Volt line through a 30.1 Kohm resistor.

The system MON5 line is coupled to ground through a parallel R-C network consisting of a 0.1 μF capacitor and a 10 Kohm resistor. The MON5 line is also coupled to the system 5VCC line through a 10 Kohm resistor. The system MON3.3 line is coupled to ground through a 0.1 μF capacitor and to the system 3.3VCC line through a 100 Kohm resistor. A SerialClocK line is coupled to the InputOutputCLocK terminals of both of A/Ds 704, 706. The system MasterInSlaveOut line is coupled to the DataINput terminals of both of A/Ds 704, 706.

The system notAnalogtoDigitalConverterChipSelect0 and notAnalogtoDigitalConverterChipSelect1 lines are coupled to the notChipSelect terminals of A/Ds 704, 706, respectively. The system notADCCS0 and notADCCS1 lines are also individually coupled to ground through a serial combination of a 100 ohm resistor and a 100 pF capacitor. The DataOutput terminal of A/D 704 is coupled to an input terminal 1A of a non-inverting buffer amplifier, illustratively one fourth of a Fairchild type 74VHC125 quad buffer 708. The buffer 1notOutputEnable terminal of quad buffer 708 is coupled to the system notADC-CS0 line.

The DataOUTput terminal of A/D 706 is coupled to an input terminal 2A of a non-inverting buffer amplifier in buffer 708. The buffer 2notOutputEnable terminal of quad buffer 708 is coupled to the system notADC-CS1 line. The output terminals of these buffers, pins 3 and 6 of quad buffer 708, are coupled to the system MasterInSlaveOut line. The system GG-DataInput line is coupled to an input terminal, pin 12, of another of the buffers in quad buffer 708. GG-DI converted to 3V appears at the output terminal, pin 11, of this buffer. The notOutputEnable terminal of this buffer is coupled through a 1 Kohm resistor to ground. The final buffer input terminal 3A and 3notOutputEnable are coupled to ground.

Turning now to FIGS. 8A–8E, controller 20 includes a microprocessor (μP) 320, which illustratively is a Motorola type MC68LK332QP μP. The notInterruptReQuest4, notInterruptReQuest5, notInterruptReQuest6 and notInterruptReQuest7 terminals of μP 320 are coupled to the system GG-DI-3V, GG-DO, GG-CLK and notNMI lines, respectively. TP0, TP1, TP6, TP7 and TP10 terminals of μP 320 are coupled to the system VALVE2, VALVE1, STEP2, STEP1 and CLocK-TEST lines, respectively. A 32.768 kilohertz (KHz) clock circuit is coupled across the eXTernAL and EXTernAL terminals of μP 320. This circuit includes a 32.768 KHz crystal, one terminal of which is coupled to the EXTAL terminal and the other terminal of which is coupled through a 332 Kohm resistor to the XTAL terminal. Both terminals of the crystal are coupled to ground through separate 12 picofarad (pF) capacitors. The XTAL and EXTAL terminals are coupled together through a 10 megaohm (Mohm) resistor.

The XFC and VDDSYN terminals of μP 320 are coupled together through a parallel circuit, one leg of which includes a series 18.2 Kohm resistor and 0.1 μF capacitor and the other leg of which includes a 0.01 μF capacitor. Terminal VDDSYN is also coupled to ground through the parallel combination of a 0.1 μF capacitor, a 0.01 μF capacitor, and a 0.1 μF capacitor. Terminal VDDSYN is coupled to +3.3 VCC through a 100 ohm resistor.

The system CLKOUT, MISO, MOSI and SCK lines are coupled to the CLKOUT, MISO, MOSI and SCK terminals, respectively, of μP 320. The system notADC-CS0 and notADC-CS1 lines are coupled to the notPeripheralChipSelect0/notSlaveSelect and notPeripheralChipSelect1 terminals, respectively, of μP 320. The notPeripheralChipSelect3 terminal of μP 320 is coupled to the notChipSelect terminal of an electronically erasable programmable read only memory (EEPROM) module 720 such as, for example, a MicrochipTechnology type 25LC320 four kilobit (K) by eight bit serial electrically erasable PROM.

NotWriteProtect and notHOLD terminals of EEPROM 720 are coupled to the system notEE_WP line. SerialdataInput and SerialdataOutput terminals of EEPROM 720 are coupled to the system MOSI and MISO lines, respectively. A VCC terminal of EEPROM 720 is coupled to the system 3.3VCC line and to ground through a 0.1 μF capacitor. The VSS terminal of EEPROM 720 is also coupled to ground. The SCK terminal of EEPROM 720 is coupled to the system SCK line.

The system TransmitData (TXD) and ReceiveData (RXD) lines are coupled to the TXD and RXD terminals, respectively, of μP 320. The notInstructionPIPEline/DevelopmentSerialOut, notInstructionFETCH/DevelopmentSerialIn, notBreaKPoinT/DevelopmentSerialCLocK, TSTIME/ThreeStateControl, FREEZE/QUOtientouT, and notHALT terminals of μP 320 are coupled to the system notIPIPE/DSO, IFETCH/DSI, notBKPT/DSCLK, TSC, FREEZE and notHALT lines, respectively. The notRESET terminal of μP 320 is coupled to the system notRESET line and to ground through a manual reset jumper.

The notRESET terminal of μP 320 is also coupled to pin 7 of a common ribbon cable connector 710, illustratively an IDC10 connector, to the system 3.3VCC line through a 825 ohm resistor, to the data line D3 through a serial combination of a rectifier diode and a 1 Kohm resistor, and to the drain terminal of an N-channel enhancement mode field effect transistor (FET). The source terminal of the FET is coupled to ground while the gate terminal is coupled to the ReSeT terminal of a microprocessor supervisory circuit 708, illustratively a MAX824TELK integrated μP supervisory circuit, through a 1 Kohm resistor.

The voltage supply, VCC, and GrouND terminals of μP supervisory circuit 708 are coupled to the system 3.3VCC line and to ground, respectively. The WatchDogInput terminal of μP supervisory circuit 708 is coupled to the system notWatchDogSTRoBe line through a 10 Kohm resistor and to the system CLocKOUT line through a jumper.

The notBusERRor terminal of μP 320 is coupled to pin 2 of a connector 710. Pin 1, pins 3 and 5, pin 9, pin 4, pin 6, pin 8, and pin 10 of connector 710 are coupled to the system notDS, ground, 3.3VCC, notBKPT/DSCLK, FREEZE, notIFETCH/DSI, and notIPIPE/DSO lines, respectively. The Address terminals, A0–A19, of μP 320 are connected to the system address bus lines A0–A19, respectively. The Data terminals, D0–D15, of μP 320 are connected to the system data bus lines D0–D15, respectively.

The Address21/ChipSelect8, Address22/ChipSelect9 Address23/ChipSelect10 terminals of μP 320 are coupled to the system notSTEPPERS, notSWitchSENSORS, and CONTROL1 lines, respectively. The notChipSelectBOOT, notBusRequest/notChipSelect0, notBusGrant/ChipSelect1, and BusGrantACKnowledge/ChipSelect2 are coupled to the system notBOOT, notDATA, notRAM, notRAML lines, respectively. The FunctionCode0/notChipSelect3, FunctionCode1/notChipSelect4, FunctionCode2/notChipSelect5 terminals of μP 320 are coupled to the system notLCD, not SWitchPANEL, and notLEDS lines, respectively.

The Read/Write terminal of μP 320 is coupled to the input of a hex schmitt inverter, which illustratively is a Fairchild 74VHC14 Hex Schmitt Inverter. The output of the hex schmitt inverter is coupled to the first input of a first OR-gate, illustratively a 74VHC32 quad 2-input OR-gate. The second input terminal of the first OR-gate is coupled to the notDataStrobe terminal of μP 320 while the output terminal of the OR-gate is coupled to the system notReaD line. The R/W and DS terminals of μP 320 are also coupled to the two input terminals of a second 2-input OR-gate. The output terminal of the second OR-gate is coupled to the system notWRite line. PortE6/SIZe0, notDataSizeACKnowledge0, notDataSizeACKnowledge1, notAutoVECtor, and MODeCLocK terminals of μP 320 are coupled with the system notWatchDogSTRoBe, notDSACK0, notDSACK1, notAVEC, and MODCLK lines, respectively. Voltage STandBy terminal of μP 320 is coupled to ground.

Controller 20 includes four memory modules, one of which is a boot block flash memory module 712, illustratively an Intel TE28F800B3B 3-Volt Advanced Boot Block Flash Memory. The data terminals, D0–D15, of the boot block flash memory module 712 are coupled to the system data bus D0–D15 lines, respectively. The address terminals of memory module 712, A0–A18, are coupled to the system address bus A1–A19 lines, respectively. In addition, each of the A0–A19 lines and the D0–D15 lines are coupled to ground through respective series combinations of a 22 ohm resitor and a 100 pF capacitor. The voltage supply terminals, VCCQ and VoltageProgram/erasePower, of memory module 712 are coupled to the system 3.3VCC line. The notResetdeepPowerdown, notChipEnable, notOutputEnable, notWriteEnable terminals of memory module 712 are coupled to the system notRESET, notBOOT, notRD, and notWR lines, respectively. notWriteProtect terminal of module 712 is coupled to ground through a 10 Kohm resistor and to the system 3.3VCC line through a jumper.

Another memory module included in controller 20 is a Flash Programmable Erasable Read Only Memory (PEROM) module 714, illustratively an Atmel AT29LV256 PEROM. The data terminals, D0–D17, of the PEROM module 714 are coupled to the system data bus D8–D15 lines, respectively. The address terminals of memory module 714, A0–A14, are coupled to the system address bus A0–A14 lines, respectively. The notOutputEnable, notChip Enable, and VCC terminals of memory module 714 are coupled to the system notRD, notDATA, and 3.3VCC lines, respectively. The VoltageProgram/erasePower terminal of module 714 is coupled to either system 3.3VCC or notWR through a selectable jumper.

Controller 20 also includes two 256K static Random Access Memory modules 716, 718, illustratively two ISSI IS62LV2568ALL 256K 8 bit Static RAMs. The data terminals, D0–D7, of RAM modules 716, 718 are coupled to the system data bus D0–D7, D8–D15 lines, respectively. The address terminals, A0–A17, of RAM module 716 are coupled to the system address bus A1–A18 lines, respectively. The address terminals, A0–A16, of RAM module 718 are coupled to the system address bus A1–A17 lines, respectively. The address terminal A17 of RAM module 718 is coupled to either system address bus line A18 or A0 through a selectable jumper.

The ChipEnable2, OutputEnable, and Read/Write terminals of RAM modules 716, 718 are coupled to the system 3.3VCC line, notRD, and notWR lines, respectively. The ChipEnable1 terminals of RAM modules 716, 718 are coupled to the system notRAML and notRAM lines, respectively. The system notRD, notDATA, notWR, notRAM, and notRAML lines are each coupled to ground through respective series combinations of a 100 ohm resistor and a 100 pF capacitor.

Referring now to FIGS. 9A–9D, user interface 18 includes controls for each of the systems 14, 16. Only one of these sets of controls will be described, with the understanding that the other is substantially identical except where noted otherwise. The switches or buttons of a membrane switch panel are coupled to the system notHOME-KEY, notUPARROW, notDowNARROW, notBACK, notENTER, notFLUSH, notPAUSE and notSILENCE lines, respecitviely, through respective 100 pF/100 ohm filters of a pair of filter arrays 722, a first of the filter arrays 722 being associated with the notHOME-KEY, notUPARROW, notD-NARROW, and notBACK lines and a second of the filter arrays 722 being associated with the notENTER, notFLUSH, notPAUSE, and notSILENCE lines. These lines are coupled through respective 3.3 Kohm pull-up resistors to +3.3 V supply voltage. These lines are also coupled to respective input terminals 1A1, 1A2, 1A3, 1A4, 2A1, 2A2, 2A3 and 2A4 of a Fairchild type 74VHC244 octal buffer 724. The respective output terminals 1Y1, 1Y2, 1Y3, 1Y4, 2Y1, 2Y2, 2Y3 and 2Y4 of buffer 724 are coupled to the system D0–D7 lines, respectively. The respective output terminals of the other system 14, 16 are coupled to the system D8–D15 lines.

Certain indicators and panel lighting are common to the two systems 14, 16, including a power indicator, a battery indicator, a silence indicator and a backlight. The power switch is coupled through a filter tuned at approximately 10 MHz to the system notPOWER LED line which is, in turn, coupled through series 316 ohm resistor to the collector of a transistor, such as, for example, output terminal 1C of a Darlington-coupled pair in an Allegro Microsystems type ULN2003 Darlington array 726. The system notBATTERY LED line is coupled through a filter tuned at approximately 10 MHz to a series 316 ohm resistor which is, in turn, coupled to, for example, terminal 2C of array 726. The system notSILENCE LED line is coupled through a filter tuned at approximately 10 MHz to a series 316 ohm resistor which is, in turn, coupled to, for example, terminal 3C of array 726. The system notBacKLIGHT line is coupled to, for example, terminal 4C of array 726.

System +5 V 5VCC is coupled to the anodes of indicator LEDs 728, 730, 732, 734. The cathodes of LEDs 728, 730, 734 are coupled through respective series 316 ohm resistors to associated terminals 5C, 6C and 7C of array 726. The cathode of LED 734 is coupled through a 316 ohm resistor to ground.

The system D0–D7 lines are coupled to input terminals of respective flip-flops, such as, for example, input terminals D0–D7, respectively, of a Fairchild type 74VHC273 octal D-type flip-flop 736. The output terminals of the respective flip-flops, such as, for example, terminals Q0–Q6 of flip-flop 736, are coupled to the bases of respective transistors, such as the bases of the input transistors of Darlington array 726. The CLocK and notMasterReset terminals of flip-flop 736 are coupled to the system notLEDS and notRESET lines, respectively. The CLK terminal of flipflop 736 is also coupled to ground through a series combination of a 100 ohm resistor and a 100 pF capacitor. A VCC terminal of flip-flop 736 is coupled to 3.3 VCC and is coupled to ground through a 0.1 µF capacitor Referring now to FIGS. 10A–10F, the user interface 18 includes a LCD interface for displaying system information to and acquiring information from the caregiver. A first octal 3-state buffer arrays 738, for example a Fairchild 74HCT244 Octal Buffer/Line Driver with 3-State Outputs, and a second octal 3 state buffer array 740, for example, a Fairchild 74VHC244 Octal Buffer/Line Driver with 3-State Outputs, work in a parallel fashion to transfer input and output information from the LCD to the system data bus.

The input terminals, A1–A8, of buffer array 738 and the output terminals, Y1–Y8, of buffer array 740 are coupled to the system address bus D8–D15 lines, respectively. The output terminals, Y1–Y8, of buffer array 738 and the input terminals, A1–A8, of buffer array 740 are coupled to the system LCD-D0, LCD-D1, LCD-D2, LCD-D3, LCD-D4, LCD-D5, LCD-D6, and LCD-D7 lines, respectively. The system LCD-D0 through LCD-D7 lines are coupled through respective 100 pF/100 ohm filters of a pair of filter arrays 742 to pins 6–13, respectively, of a LCD connector 744.

The VCC and GrouND terminals of buffer arrays 738, 740 are coupled to the system 3.3VCC line and ground, respectively. In addition, the VCC terminals of buffer arrays 738, 740 are coupled to ground through respective 0.1 µF capacitors. The system notLCD and notWR lines are coupled to the inputs of a 2-input OR gate, the output of which is coupled to the not1OutputEnable and not2OutputEnable terminals of array buffer 738. Similarly, the system notLCD and notRD lines are coupled to the inputs of a 2-input OR gate, the output of which is coupled to the not1OutputEnable and not2OutputEnable terminals of array buffer 740.

The system notLCD line is also coupled to the input terminal, D, of a D-type flip-flop 746, illustratively a Fairchild 74HCT74 Dual D-Type Flip-Flop. The system CLK-OUT line is coupled to the CLocK terminal of flip-flop 746 and to ground through a series combination of a 100 ohm resistor and a 100 pF capacitor. The GRounD and VCC terminals of flip-flop 746 are coupled to ground and to the system 5VCC line, respectively. The CLeaR and PReset terminals of flip-flop 746 are coupled through respective 1 Kohm resistors to the system VCC and 5VCC lines, respectively.

The output terminal, Q, of flip-flop 746 and the system notLCD line are coupled to the inputs of a 2-input AND gate. The notLCD line is also coupled to ground through a series combination of a 100 ohm resistor and a 100 pF capacitor. The output of the AND gate is coupled to the system notDeLaY-LCD line. The system notWR, notRD, A0, notDLY-LCD, and notRESET lines are coupled to respective input terminals, A1–A5, of a octal buffer array 748, illustratively a Fairchild 74HCT244 octal Buffer with 3-State Outputs.

Input A6–A8 of buffer array 748 are coupled to ground through respective 1 Kohm resistors. not1OutputEnable, not2OutputEnable, and GRounD terminals of buffer array 748 are coupled to ground. The voltage terminal, VCC, of buffer array 748 is coupled to the system 5VCC line and to ground through a 0.1 µF capacitor. The output terminals, Y1–Y5, of buffer array 748 are coupled to the system notLCD-WRITE, notLCD-READ, LCD-A), notLCD-ChipSelect, and notLCD-RESET lines, which are, in turn, coupled through respective 100 pF/100 ohm filters (e.g. filters tuned at approximately 10 MHz) to pins 3, 2, 4, 5, and 1, respectively, of connector 744. Four of the filters are included in filter array 743.

Connector 744 includes connections for contrast adjustment. Power for contrast adjustment is provided by an inverting charge pump 750, for example a Maxim MAX868 Regulated, Adjustable −2x Inverting Charge Pump. The notSHutDoWn and voltageINput terminals of pump 750 are coupled to the system 5VCC line. The PowerGrouND and analogGrouND terminals of pump 750 are coupled to the system ground. Separate 0.1 µF capacitors are coupled between the flying Capacitor2+ and Capacitor2− terminals and the Capacitor1+ and Capaictor1− terminals of pump 750. The C1+ terminal of pump 750 is also coupled to the anode of a first rectifying diode and the cathode of a second rectifying diode through a 0.1 µF capacitor.

The cathode of the first diode is coupled to the OUTput terminal of pump 750 and to ground through a 0.1 µF capacitor. The anode of the second diode is coupled to ground through a 1.0 µF capacitor, to the first terminal of a 10 Kohm resistor pot, and to the FeedBack terminal of pump 750 through a 374 Kohm resistor. The FB terminal of pump 750 is also coupled to the system 5VCC line through a 100 Kohm resistor. The second terminal of the 10 Kohm pot is coupled directly to ground. The first terminal and sweep terminal of the 10 Kohm pot are coupled to pins 16 and 17, respectively, of connector 744 through separate filters tuned at approximately 10 MHz.

Figure 11:
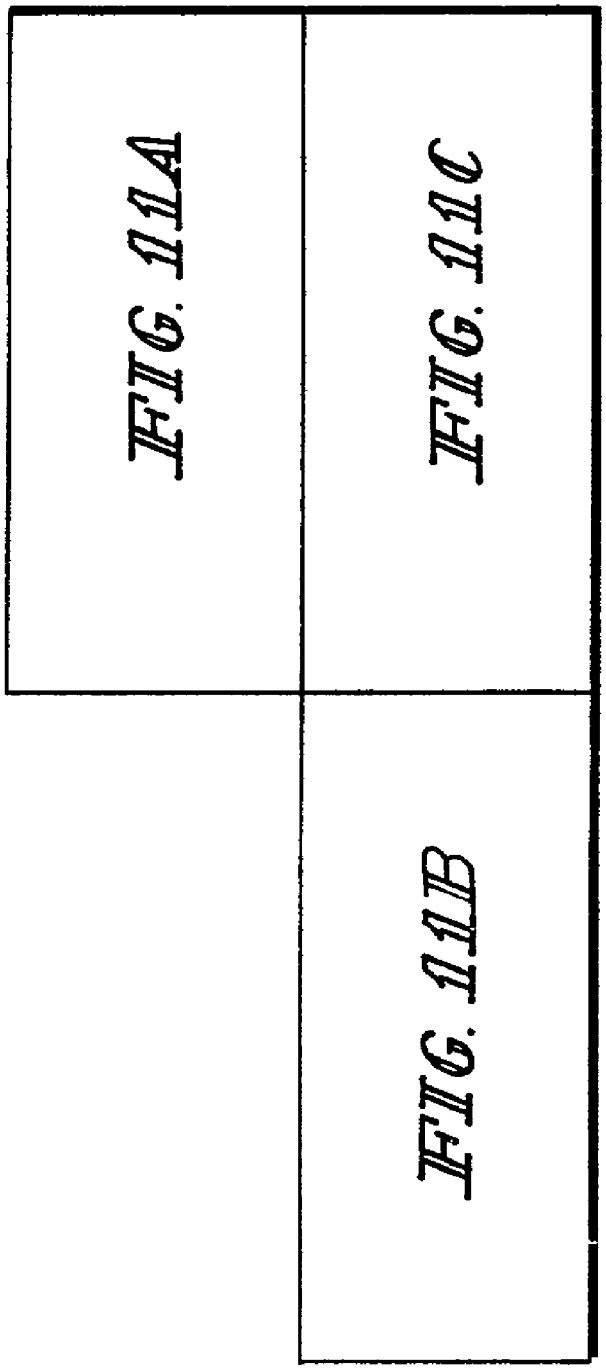
Figure 11B:
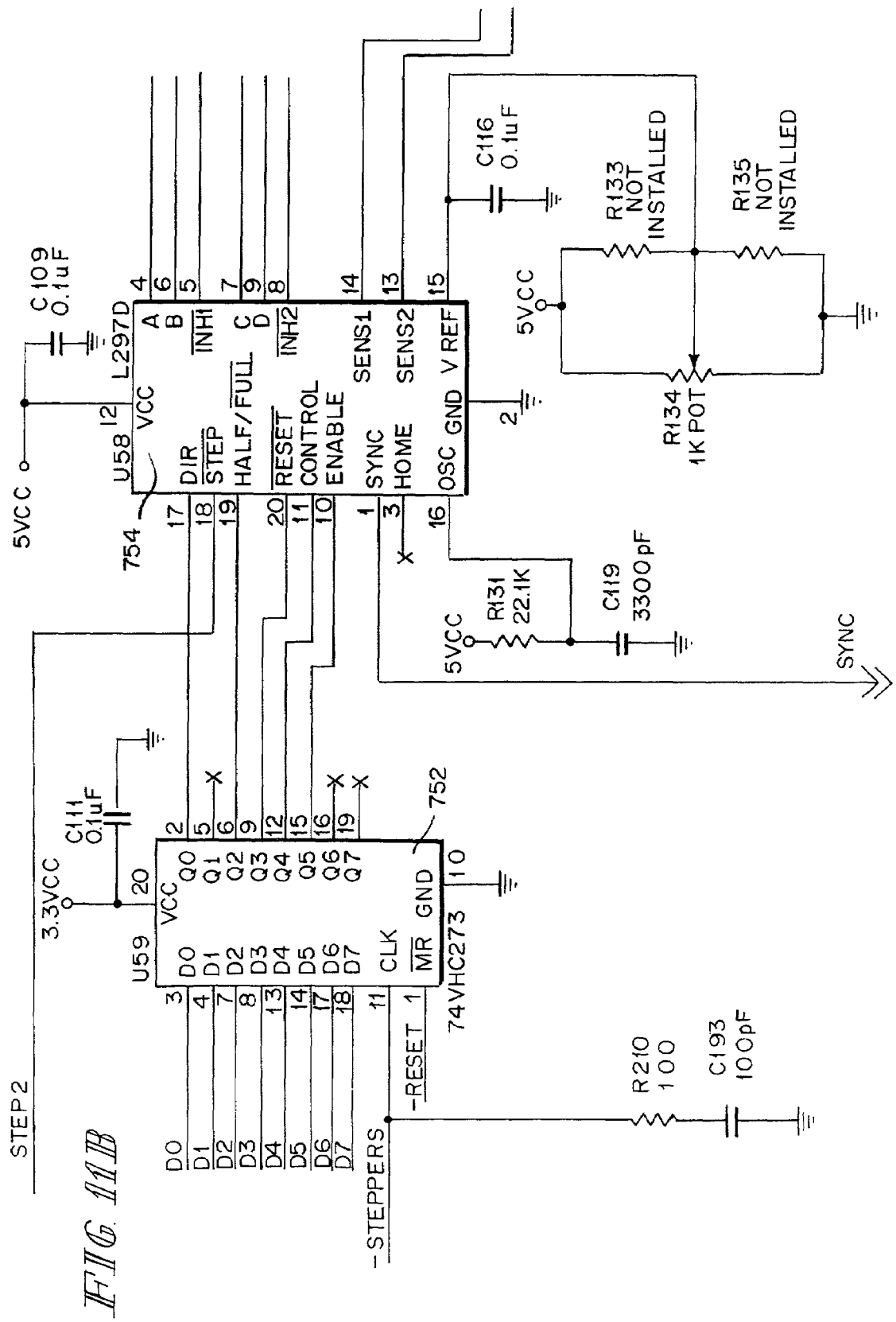
Figure 11C:
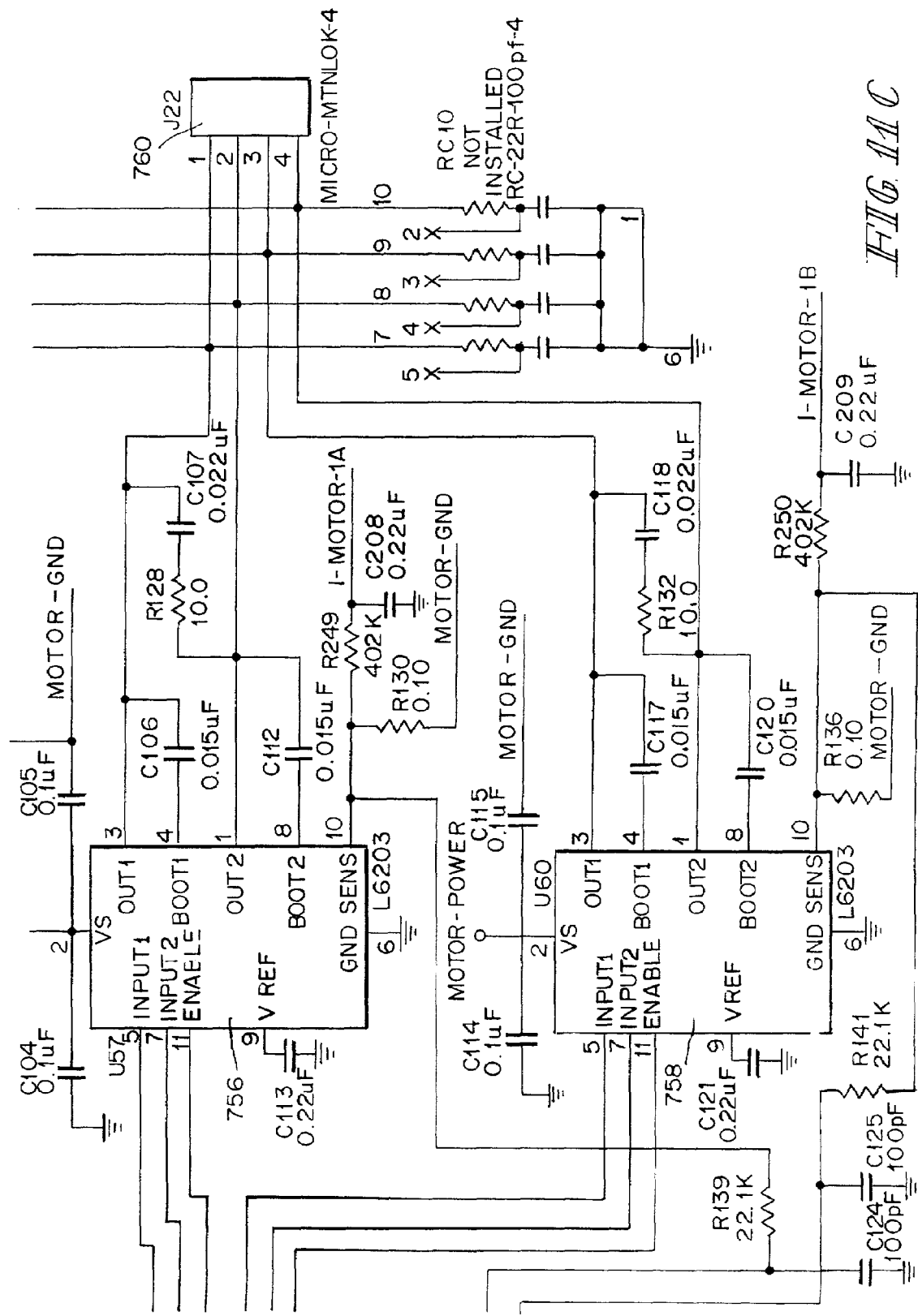
Figure 12:
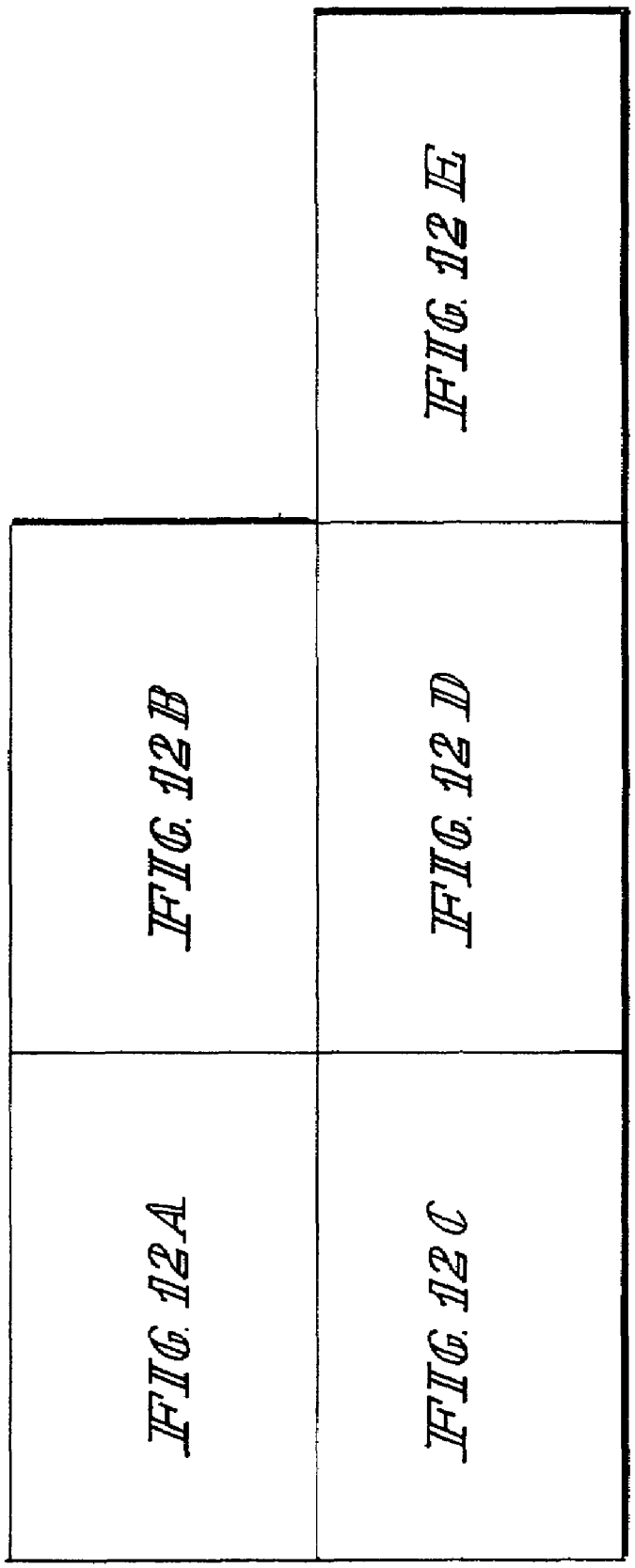
Figure 12A:
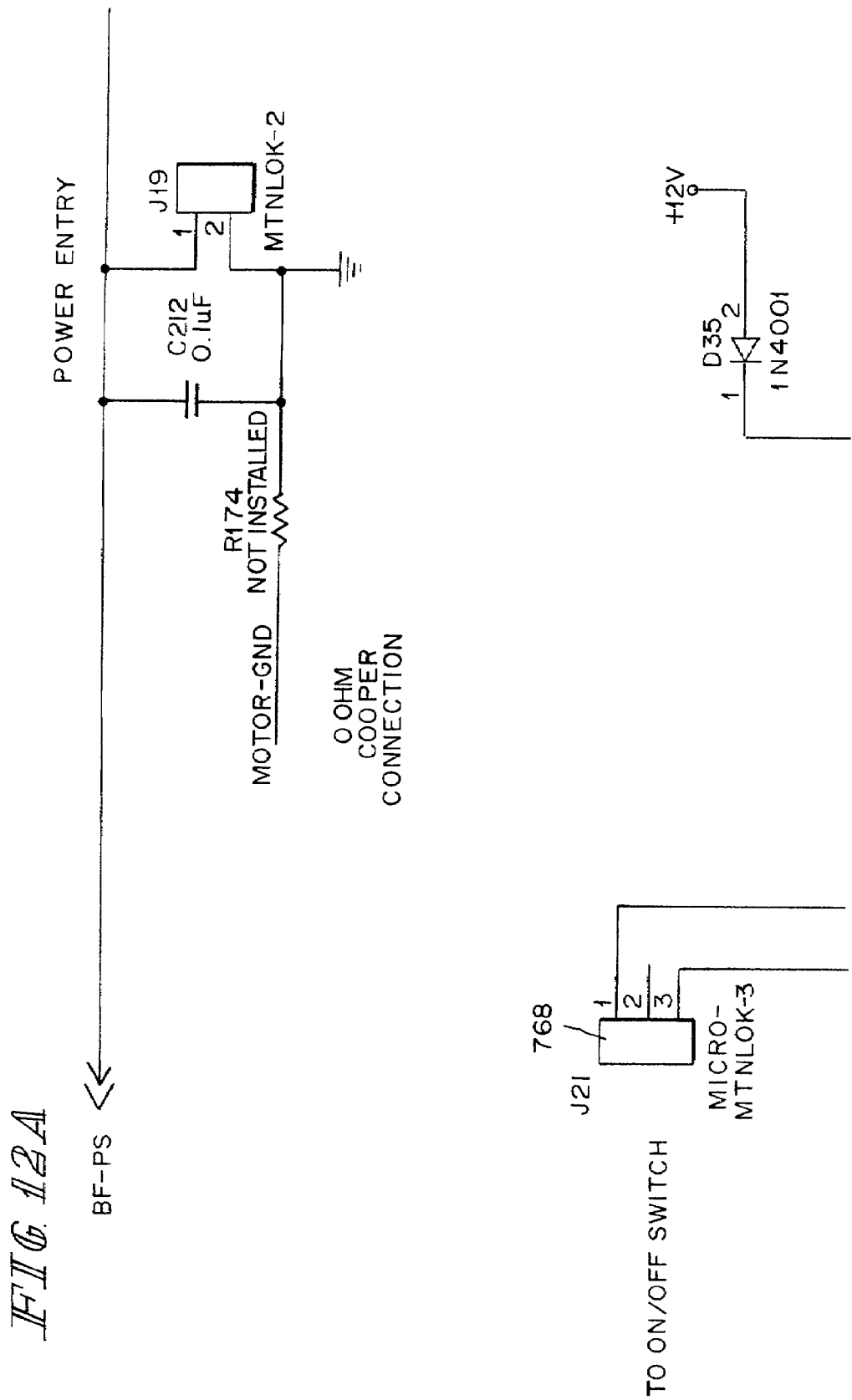
Figure 12C:
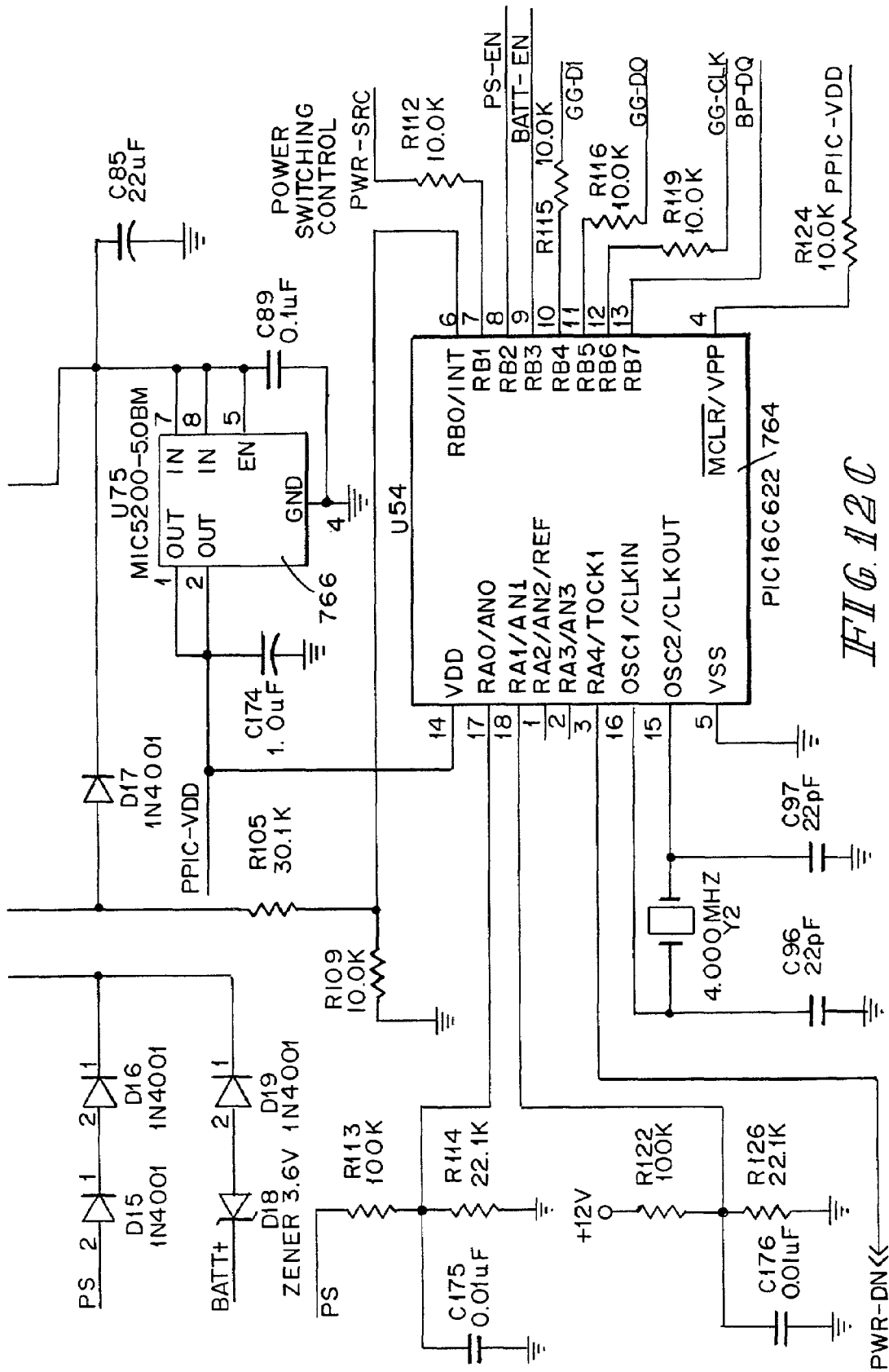
Figure 12D:
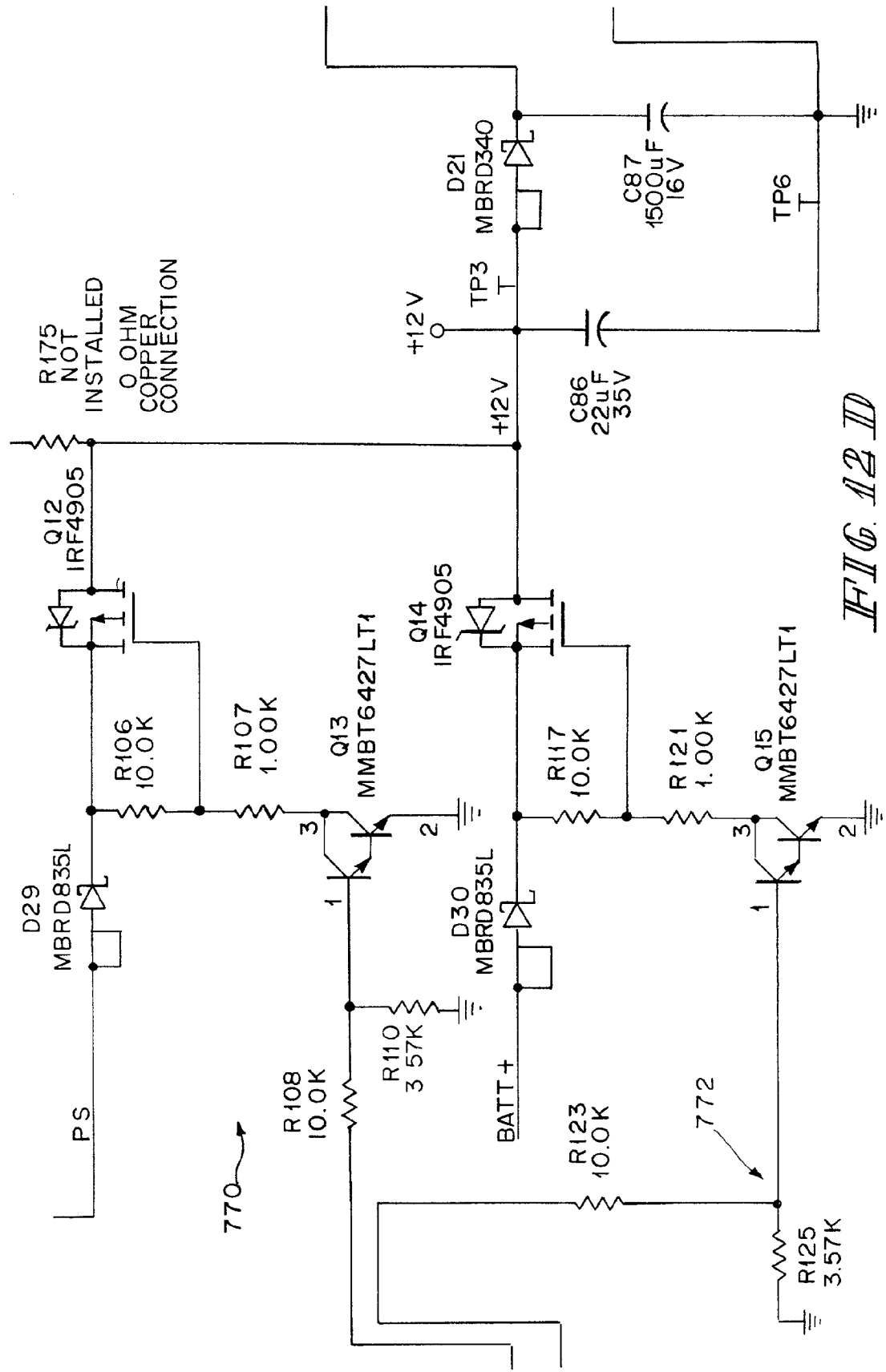
Figure 42E:
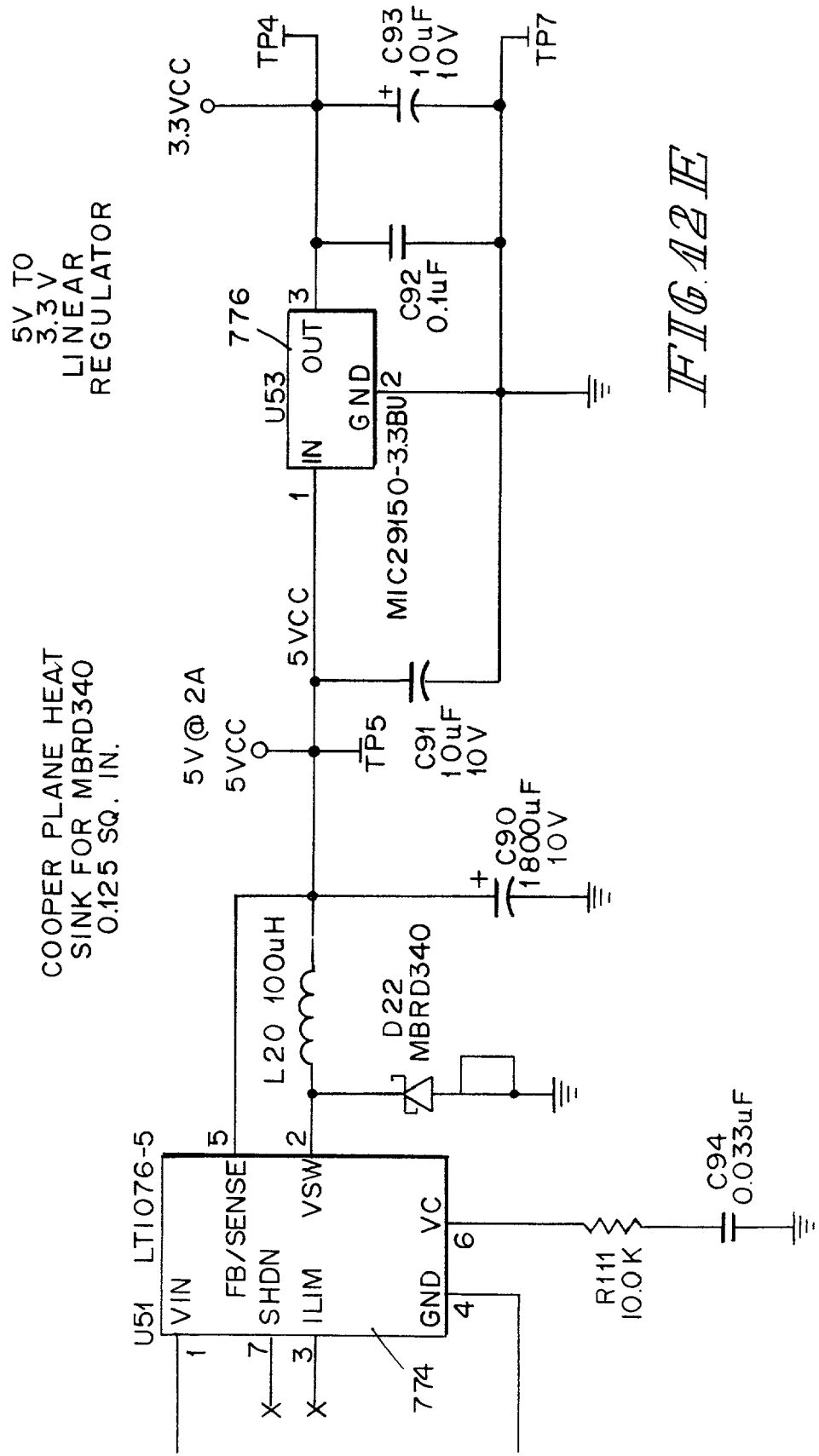
Figure 13:
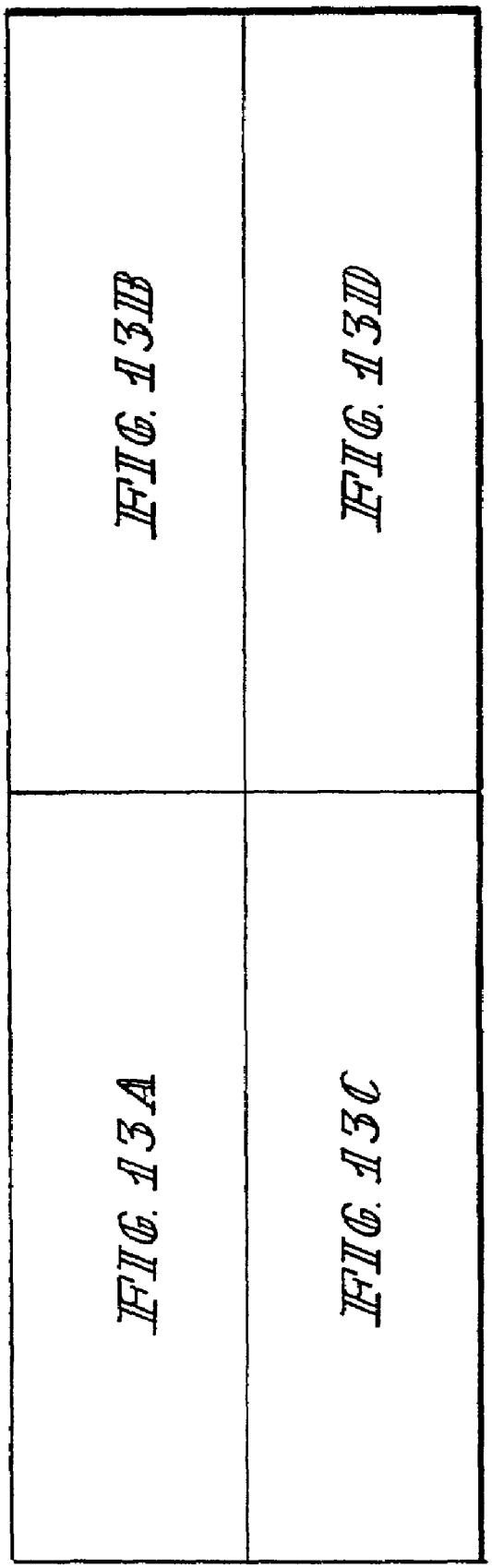
Figure 13A:
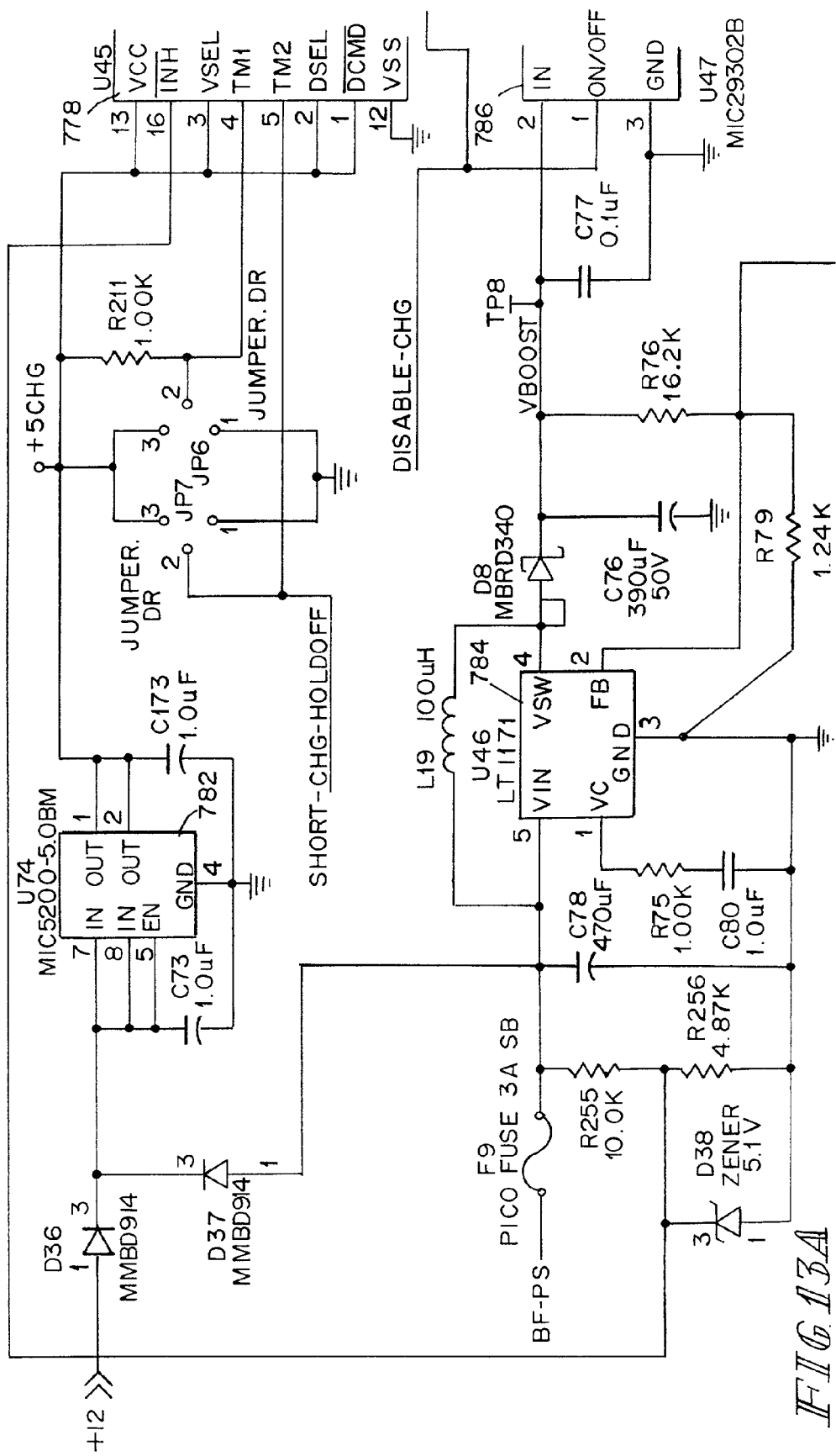
Figure 13B:
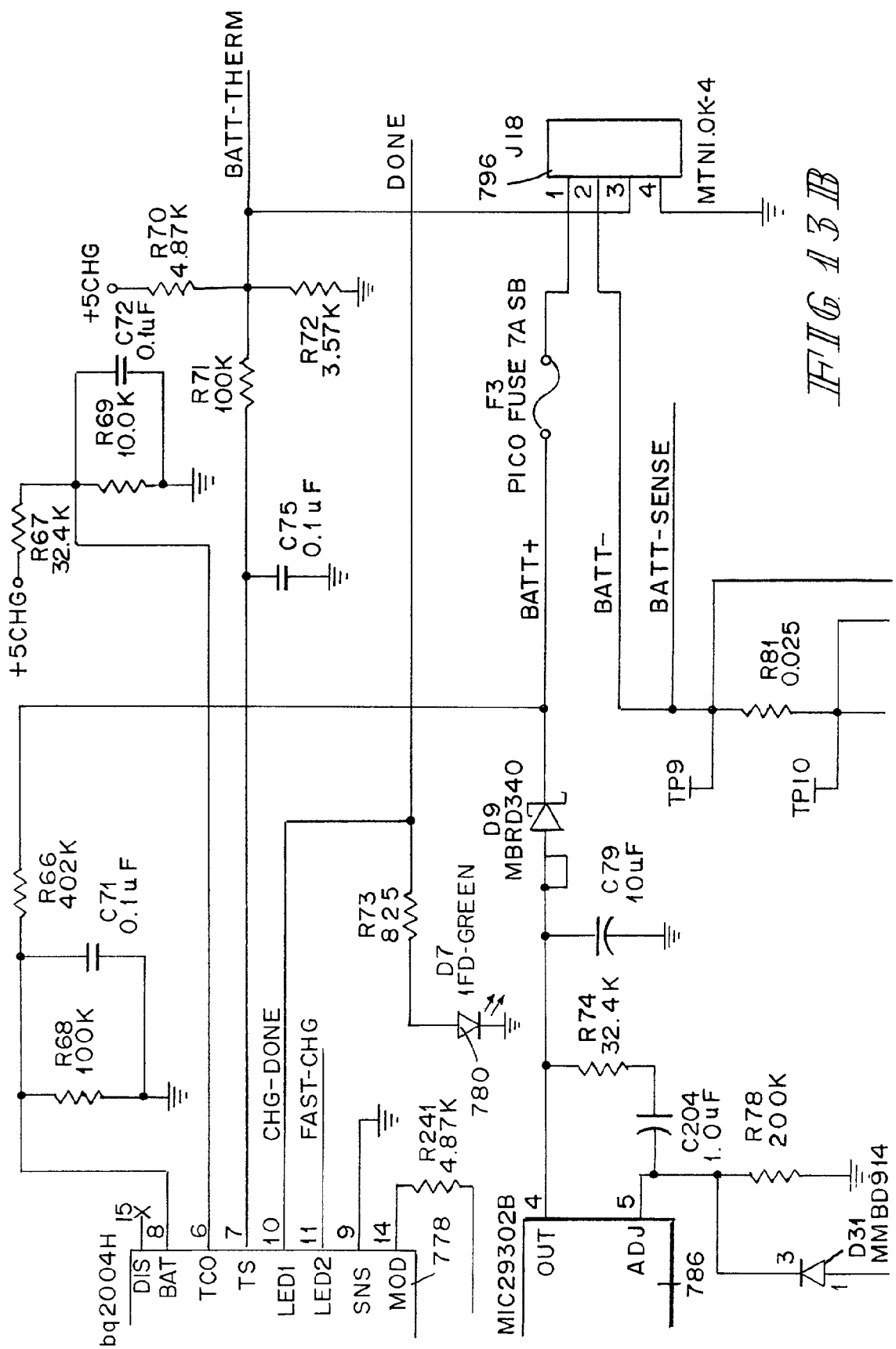
Figure 13C:
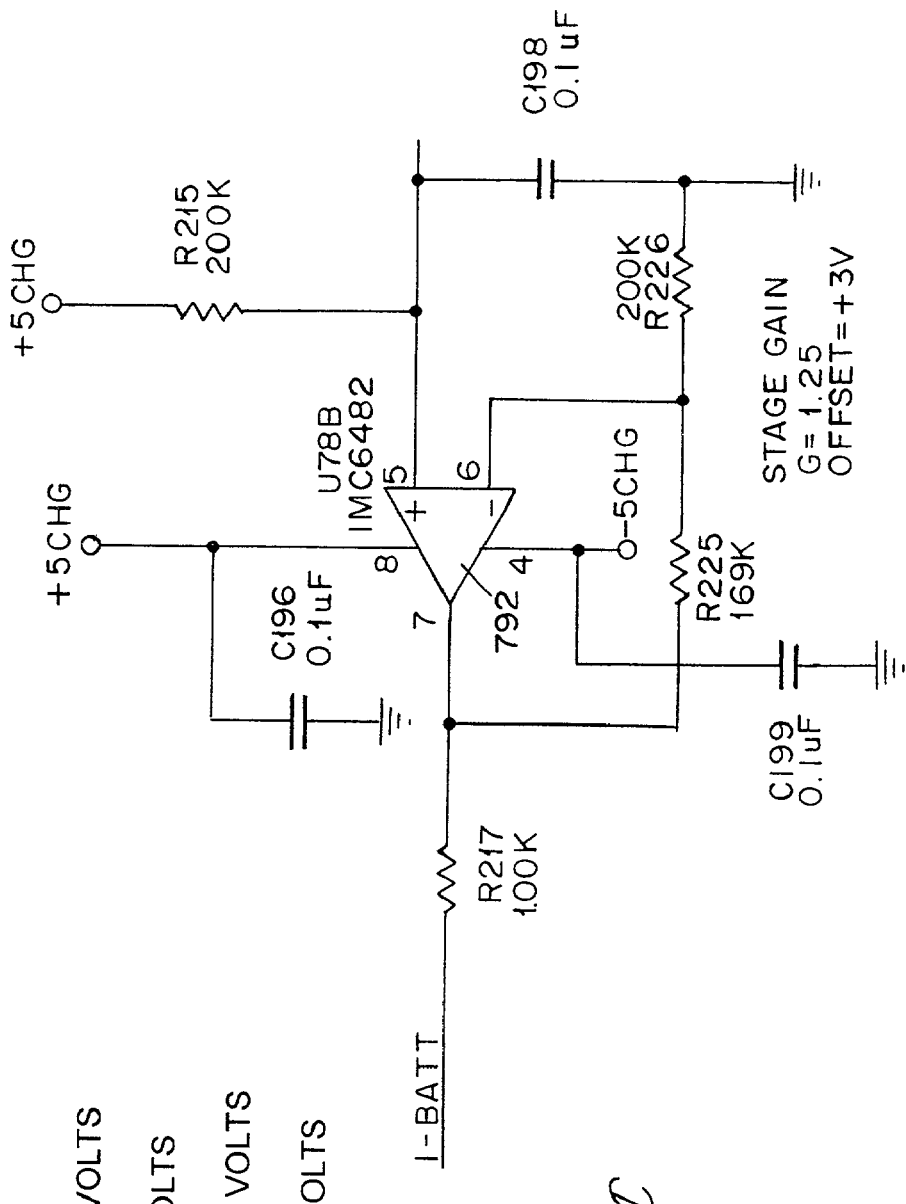
Figure 13D:
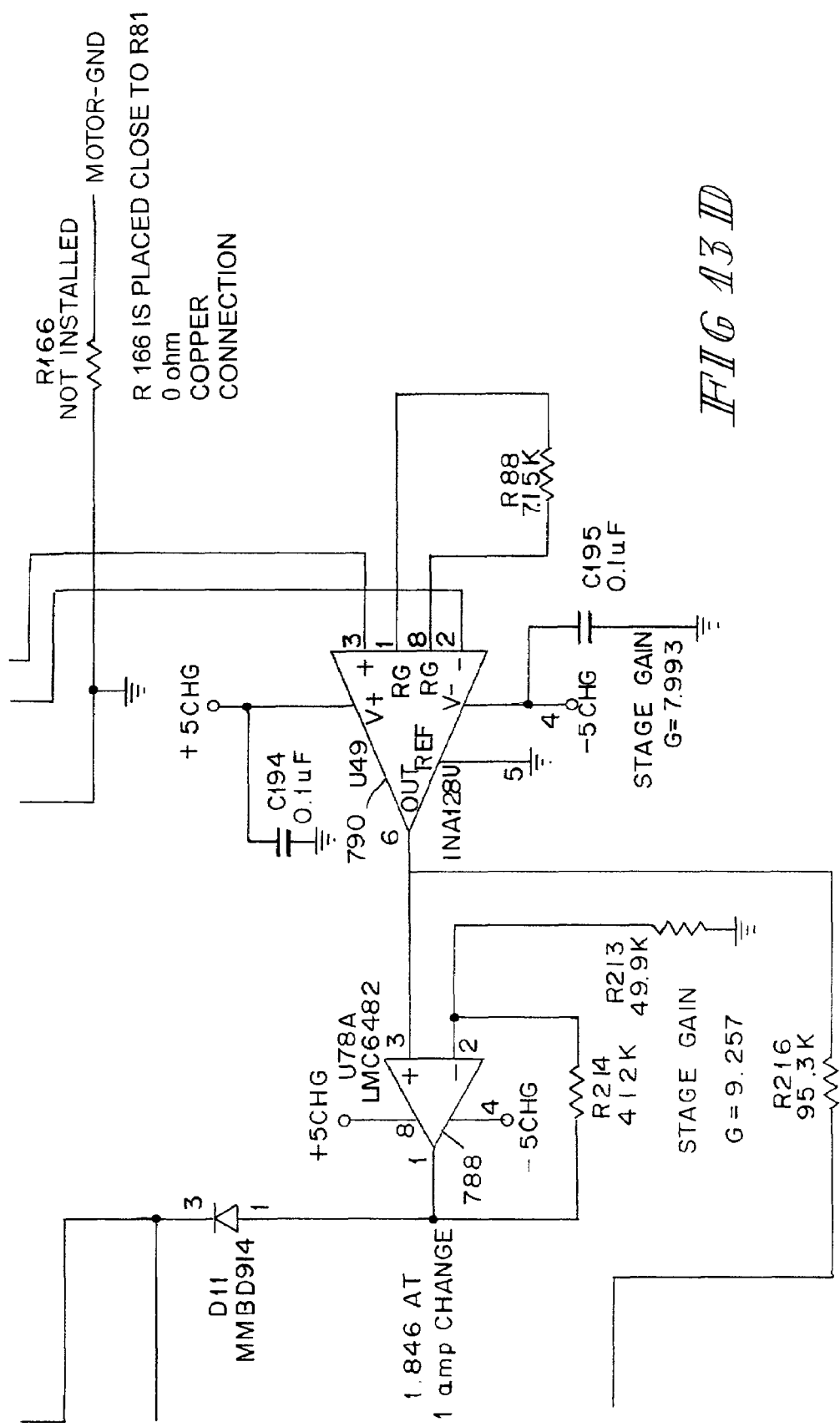

Referring now to FIGS. 11A–11C, systems 14, 16 include controls for the separate syringe drive motors 72, 172, respectively. Only one of these control circuits will be described, with the understanding that the other is substantially identical except where noted otherwise. The system notSTEPPERS line is coupled to the CLocK terminal of an octal D-type flip-flop 752, illustratively a Fairchild 74VHC273 Octal D-Type Flip-Flop. The VCC, GRounD, and MasterReset terminals of flip-flop 752 are coupled to the system 3.3VCC line, ground, and the system notRESET line, respectively. In addition, the VCC terminal of flip-flop 752 is coupled to ground through a 0.1 µF capacitor.

The input terminals, D0–D7, of flip-flop are coupled to the system data bus D0–D7, respectively. The output terminals Q0, Q2, Q3, Q4, and Q5 of flip-flop 752 are coupled, respectively, to the DIRection, HALF/notFULL, notRESET, CONTROL, and ENABLE terminals of a stepper motor controller 754, for example a SGS-Thomson L297 Stepper Motor Controller. The VCC, GRounD, and STEP terminals of controller 754 are coupled to the system 5VCC, ground, and STEP2 lines, respectively. In addition the VCC terminal of controller 754 is coupled to ground through a 0.1 µF capacitor. The OSCillator terminal of controller 754 is coupled to ground through a 3,300 pF capacitor and to the system 5VCC line through a 22.1 Kohm resistor.

The SYNChronize terminal of controller 754, which is associated with drive motor 72, is coupled to the controller circuit for drive motor 172. The VoltageREFerence terminal of controller 754 is coupled to ground through a 0.1 µF capacitor and to the wiper of a 1 Kohm resistor pot. The first terminal this 1 Kohm resistor pot is coupled to the system 5VCC line and the second terminal is connected to the system ground. The motorphaseA, motorphaseB, and notINHibit1 terminals of controller 754 are coupled to the INPUT1, INPUT2, and ENABLE terminals of a first full bridge driver 756, illustratively an SGS-Thomson L6203 DMOS Full Bridge Driver. The motorphaseC, motorphaseD, and notINHibit2 terminals of controller 754 are coupled to the INPUT1, INPUT2, and ENABLE terminals of a second full bridge driver 758. The SENSe1 and SENSe2 terminals of controller 754 are coupled to the SENSe terminals of drivers 756, 758, respectively, through respective 22.1 Kohm resistors. The SENSe1 and SENSe2 terminals of controller 754 are also coupled to ground through respective 100 pF capacitors.

The VoltageREFerence terminals of drivers 756,758 are coupled to ground through respective 0.22 µF capacitors. The VoltageSupply terminals of drivers 756,758 are coupled to the system MOTOR-POWER line, to ground through respective 0.1 µF capacitors, and to the system MOTOR-GND line through respective 0.1 µF capacitors. The system MOTOR-GND line is also coupled to the system MOTOR-POWER line through a 22 µF capacitor and to the SENSe terminals of drivers 756, 758 through respective 0.1 ohm resistors. The SENSe terminals of drivers 756, 758 are also coupled to the system I-MOTOR-1A and I-MOTOR-1B lines, respectively, through respective 402 Kohm resistors. The system I-MOTOR-1A and I-MOTOR-1B lines are also coupled to ground through respective 0.22 µF capacitors.

The OUTput1 terminal of drivers 756, 758 is coupled to the BOOT1 terminal of drivers 756,758, respectively, through respective 0.015 µF capacitors. Similarly, the OUTput2 terminal of drivers 756,758 is coupled to the BOOT1 terminal of drivers 756,758, respectively, through respective 0.015 µF capacitors. The OUT1 terminal of drivers 756,758 are also coupled to the OUT2 terminal of drivers 756,758 through respective series combinations of a 10 ohm resistor and a 0.022 µF capacitors. The OUT1 and OUT2 terminals of driver 756 and the OUT1 and OUT2 terminals of driver 758 are coupled to pins 1–4, respectively, of flush drive connector 760 and to the INput3, INput4, INput5, and INput6 terminals, respectively, of an electronic protection array 762, illustratively a Harris SP723 Electronic Protection Array. The Voltage+ and Voltage− terminals of protection array 762 are coupled to the system MOTOR-POWER and MOTOR-GND lines, respectively.

Turning now to FIGS. 12A–12E, the power controller for wound treatment apparatus 10 is shown. The power controller includes an 8-Bit CMOS microcontroller 764, illustratively a Microchip PIC16C622 EPROM-Based 8-Bit CMOS Microcontroller. A 4 Megahertz (MHz) clock circuit is coupled across the OSCillator1/CLocKIN and OSCillator2/CLocKOUT terminals of microcontroller 764. This circuit includes a 4 MHz crystal coupled across the OSC1/CLKIN and OSC2/CLKOUT terminals of microcontroller 764. The OSC1/CLKIN and OSC2/CLKOUT terminals are also coupled to ground through respective 22 pF capacitors. The RportA0/ANaloginput0 and RportA1/ANaloginput1 terminals of microcontroller 764 are coupled to ground through respective parallel combinations of a 22.1 Kohm resistor and a 0.01 µF capacitor. The RA0/AN0 and RA1/AN1 terminals are also coupled to the system PS and +12V lines, respectively, through separate 100 Kohm resistors.

The RportA4/TOCK1, VDD, and VSS terminals of microcontroller 764 are coupled to the system PWR-DN line, the system PPIC-VDD line, and ground, respectively. The RportB0/INTerrupt terminal is coupled to ground through a 10 Kohm resistor. The remaining B port terminals, RB1–RB7, and notMasterCLeaR terminal are coupled to the system PWR-SRC, PS-EN, BATT-EN, GG-DI, GG-DD, GG-CLK, BP-DQ, and PPIC-VDD lines, respectively, through respective 10 Kohm resistors. The system PPIC-VDD line is also coupled to ground through a 1.0 µF capacitor and to the OUTput terminal, pins 1 and 2, of a linear voltage regulator 766, such as a Micrel MIC5200 Low-Dropout Regulator.

The Input terminals, pins 7 and 8, and the ENable terminal of regulator 766 are coupled to ground through a 22 µF capacitor and to the cathode terminal of a first and a second rectifier diode. In addition, the EN terminal of regulator 766 is coupled to ground through a 0.1 µF capacitor. The anode of the first rectifier diode is coupled to the system +12V line. The anode of the second rectifier diode is coupled to pin 1 of an ON/OFF switch connector 768 and to the RB0/INT terminal of microcontroller 764 though a 30.1 Kohm resistor. Pin 3 of switch connector 768 is connected to the cathode of a first and a second rectifier diode. The anode of the first rectifier diode is coupled to the cathode of a third rectifier diode and the anode of the third rectifier diode is coupled to the system PS line. The anode of the second rectifier diode is coupled to the anode of a 3.6 volt zener diode. The anode of the 3.6 volt zener diode is coupled to the system BATT+ line.

The system PS-EN and BATT-EN lines are coupled to discrete amplifier circuits 770, 772. Only the PS-EN amplifier circuit 770 will be described, with the understanding that the BATT-EN amplifier circuit 772 is substantially identical except where noted otherwise. The system PS-EN line is coupled to a voltage divider circuit formed from the series connection to ground of a 10 Kohm resistor and a subsequent 3.57 Kohm resistor. The base of a Darlington transistor, for example a MMBT6427LT1 Darlington transistor, is coupled to the center tap of the voltage divider circuit. The collector of the Darlington transistor is coupled to ground. The emitter of the Darlington transistor is coupled to the gate of a HEXFET MOSFET, illustratively an IRF4905 HEXFET Power MOSFET, through a 1 Kohm resistor.

The source terminal of the HEXFET MOSFET is coupled to the gate terminal of the MOSFET through a 10 Kohm resistor and to the anode of a Schottky barrier rectifier diode. The cathode of the Schottky diode is coupled to the system PS line in amplifier circuit 770 and to the system BATT+ line in amplifier circuit 772. In circuit 770, the PS line is coupled to the system BF-PS line through a 7 amp fuse. The BF-PS line is coupled to pin 1 of a power entry connector. Pin 2 of the power entry connector is coupled to pin 1 thereof through a 0.1 µF capacitor, to the system MOTOR-GND line, and to ground. In circuit 772, the 7 amp fuse and power entry connector are omitted.

The drain terminals of the HEXFET MOSFETs of amplifier circuits 770, 772 are coupled to the system MOTOR-POWER and +12V lines. The system +12V line is coupled to ground through a 22 µF capacitor and to the anode of a Schottky barrier rectifier diode. The cathode of said Schottky diode is coupled to ground through a 1,500 µF capacitor and to the VoltageIN terminal of a 12V to 5V buck regulator 774, illustratively a Linear Technology LT1076-8 Step-Down Switching Regulator. The GrouND terminal of regulator 774 is coupled to the system ground. The voltage reference, Vc, terminal of regulator 744 is also coupled to ground through a series R-C network consisting of a 10 Kohm resistor and a 0.033 µF capacitor.

The VoltageSWitch and FeedBack/SENSE terminals of regulator 744 are coupled together through a 100 micro-Henries (µH) inductor. The Vsw terminal of regulator 744 is also coupled to the anode of a Schottky barrier rectifier diode. The cathode of this Schottky diode is coupled to ground. The FB/SENSE terminal of regulator 744 is also coupled to the system 5VCC line and to ground through a 1,800 µF capacitor. The system 5VCC line is also coupled to ground through a 10 µF capacitor and to the INput terminal of a high current voltage regulator 776, for example a Micrel MIC29150-3.3BU High-Current Low-Dropout Regulator. The GrouND terminal of regulator 776 is coupled to ground. The OUTput terminal of regulator 776 is coupled the system 3.3VCC line and to ground through about 11 µF of capacitance.

Now referring to FIGS. 13A–13D, the battery charging system for wound treatment apparatus 10 is shown. The battery charging system includes a fast charge controller 778, illustratively an Unitrode BQ2004H Fast-Charge IC. The BATteryvoltage terminal of controller 778 is coupled to ground through a parallel R-C network consisting of a 100 Kohm resistor and a 0.1 µF capacitor. The BATT terminal is also coupled to the system BATT+ line through a 402 Kohm resistor. The TemperatureCutOff terminal of controller 778 is coupled to ground through a parallel R-C network consisting of a 10 Kohm resistor and a 0.1 µF capacitor. The TCO terminal is also coupled to the system +5CHG line through a 32.4 Kohm resistor.

The TemperatureSense terminal of controller 778 is coupled to ground through a 0.1 µF capacitor and to the system BATT-THERM line through a 100 Kohm resistor. The BATT-THERM line is coupled to ground through a 3.57 Kohm resistor and to the system +5CHG line through a 4.87 Kohm resistor. The LED1 terminal of controller 778 is coupled to the system DONE line and to the anode of LED 780 through an 825 ohm resistor. The cathode of LED 780 is coupled to ground.

The SeNSe and system ground (VSS) terminals of controller 778 are also coupled to ground. The LED2 terminal of controller 778 is coupled to the system FAST-CHG line. The charging current control, MOD, terminal of controller 778 is coupled the system notDISABLE-CHG line through a 4.87 Kohm resistor. The notINHbit terminal of controller 778 is coupled to ground through a 4.87 Kohm resistor and to the anode of a 5.1 volt zener diode. The cathode of the 5.1 volt zener diode is coupled to ground. The voltage supply (VCC), VoltageSELect, DisplaySELect, and notDischarge-CoMmanD terminals of controller 778 are each coupled to the system +5CHG line.

The TimerMode1 terminal of controller 778 is coupled to the system +5CHG line through a 1 Kohm resistor. The TM1 terminal may also be coupled to ground or directly to the system +5CHG line through a selectable jumper. The TimerMode2 terminal of controller 778 is coupled to the system SHORT-CHG-HOLDOFF line. The TM2 terminal may also be directly to ground or the system +5CHG line through a selectable jumper.

The system +5CHG line is coupled to the OUTput terminals, pins 1 and 2, of a voltage regulator 782, illustratively a Micrel MIC5200-5.0BM Low-Dropout Regulator, and to the GrouND terminal of regulator 782 through a 1.0 μF capacitor. The GND terminal of regulator 782 is coupled to ground. The INput, pins 7 and 8, and the ENable terminal of regulator 782 are coupled to the GND terminal of regulator 782 through a 1.0 μF capacitor.

The IN and EN terminals of regulator 782 are also coupled to the cathodes of a first and a second rectifier diode. The anode of the first rectifier diode is coupled to the system +12V line. The anode of the second rectifier diode is coupled to the VoltageINput terminal of a switching regulator 784, illustratively a Linear Technology LT1171 High Efficiency Switching Regulator, to ground through a 470 μF capacitor, to the system BF-PS line through a 3 amp fuse, and to the notINH terminal of controller 778 through a 10 Kohm resistor.

The operating voltage terminal (Vc) of regulator 784 is coupled to ground through a series combination of a 1 Kohm resistor and a 1 μF capacitor. The GrouND terminal of regulator 784 is also coupled to ground. The Vin and VoltageSWitch terminals of regulator 784 are coupled together through a 100 μH inductor. The VSW terminal of regulator 784 is also coupled to the anode of a Schottky barrier rectifier diode. The cathode of this Schottky diode is coupled to the system VBOOST line, to ground through a 390 μF capacitor, and to the FeedBack terminal of regulator 784 through a 16.2 Kohm resistor. The FeedBack terminal of regulator 784 is also coupled to ground through a 1.24 Kohm resistor.

The system VBOOST line is coupled to ground through a 0.1 μF capacitor and to the INput terminal of a high current voltage regulator 786, such as a Micrel MIC29302B High-Current Low-Dropout Regulator. The ON/OFF and GrouND terminals of regulator 786 are coupled to the system notDISABLE-CHG line and to ground, respectively. The OUTput terminal of regulator 786 is coupled to ground through a 10 μF capacitor and to the anode of a Schottky diode. The cathode of this Schottky diode is coupled to the system BATT+ line.

The OUT and ADJust terminals of regulator 786 are coupled together through a series R-C network consisting of a 32.4 Kohm resisotor and a 1.0 μF capacitor. The ADJ terminal of regulator 786 is also coupled to ground through a 200 Kohm resistor and to the cathode of a first rectifier diode. The anode of this first rectifier diode is coupled to the cathode of a second rectifier diode and to the FB terminal of regulator 784. The anode of this second rectifier diode is coupled to the output terminal, pin 1, of an operational amplifier 788, illustratively a National Semiconductor LMC6482 CMOS Dual Rail-to-Rail Input and Output Operational Amplifier, and to the inverting input (−) of amplifier 788 through a 412 Kohm resistor.

The inverting input terminal of amplifier 788 is coupled to ground through a 49.9 Kohm resistor. The positive voltage terminal, pin 5, and the negative voltage terminal, pin 4, of amplifier 788 are coupled to the system +5CHG and −5CHG lines, respectively. The non-inverting terminal (+) of amplifier 788 is coupled to the non-inverting input (+) of an operational amplifier 792, illustratively a National Semiconductor LMC6482 CMOS Dual Rail-to-Rail Input and Output Operational Amplifier, through a 95.3 Kohm resistor. The non-inverting terminal of amplifier 792 is also coupled to the system +5CHG line through a 200K ohm resistor and to ground through a 0.1 μF capacitor.

The inverting input terminal (−) of amplifier 792 is coupled to ground through a 200 Kohm resistor. The inverting and output terminals of amplifier 792 are coupled together through a 169 Kohm resistor. The output terminal of amplifier 792 is also coupled to the system −BATT line through a 1.0 Kohm resistor. The positive voltage supply, V+, and negative voltage supply, V−, terminals of amplifier 792 are coupled to the system +5CHG and −5CHG lines, respectively, and to ground through respective 0.1 μF capacitors.

The non-inverting input terminal of amplifier 788 is also coupled to the output terminal of an instrumentation amplifier 790, such as a Burr-Brown INA128U Low Power Instrumentation Amplifier. The REFerence terminal of amplifier 790 is coupled to ground. The positive voltage supply and negative voltage supply terminals of amplifier 790 are coupled to the system +5CHG and −5CHG lines, respectively, and to ground through respective 0.1 μF capacitors. A 7.15 Kohm gain adjusting resistor is coupled across the RG terminals of amplifier 790.

The non-inverting input terminal (+) of amplifier 790 is coupled to the system BATT− and BATT-SENSE lines. The inverting terminal (−) of amplifier 790 is coupled to the ground and to the system MOTOR-GND line. The non-inverting input terminal (+) and the inverting terminal (−) of amplifier 790 are coupled together through a 0.025 ohm resistor.

The system BATT-TERM line is coupled to ground through a 3.57 Kohm resistor, to the system +5CHG line through a 4.87 Kohm resistor, and to pin 3 of a battery connector 796. The system BATT+ line is coupled to pin 1 of connector 796 through a 7 amp fuse. The system BATT− line is coupled to pin 2 of connector 796. Pin 4 of connector 796 is coupled to ground.

Figure 14:
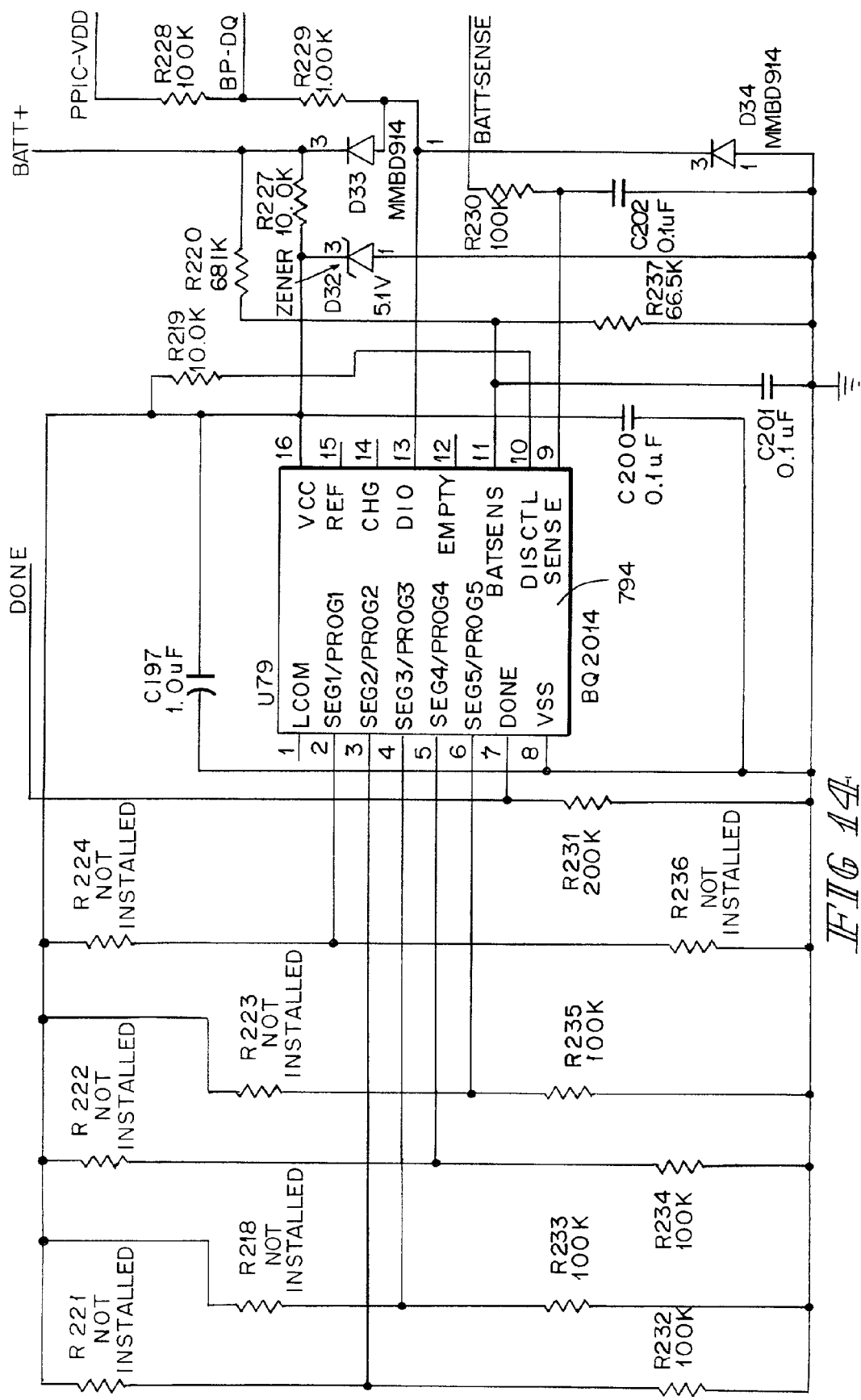
Figure 15A:
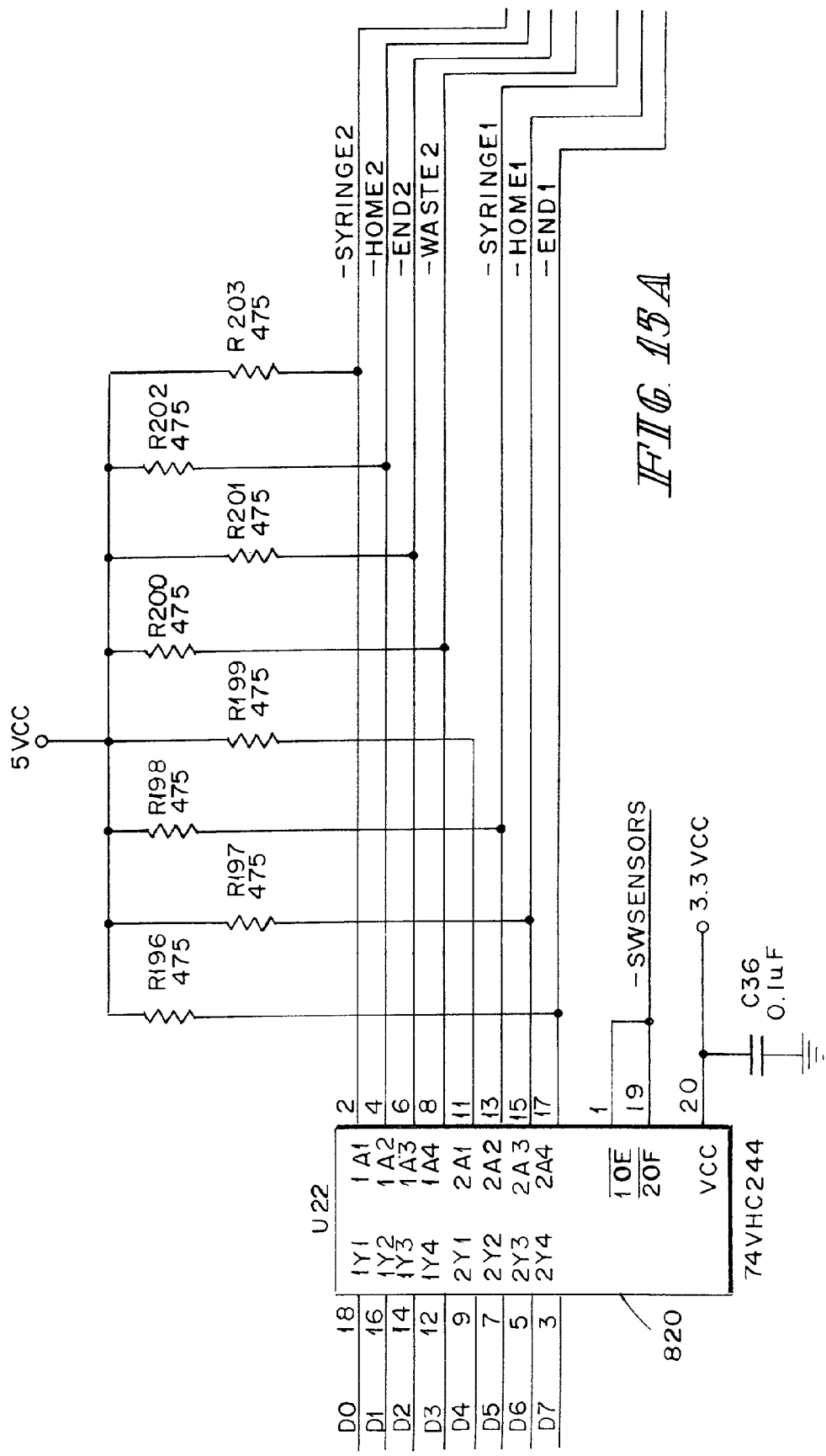
Figure 13B:
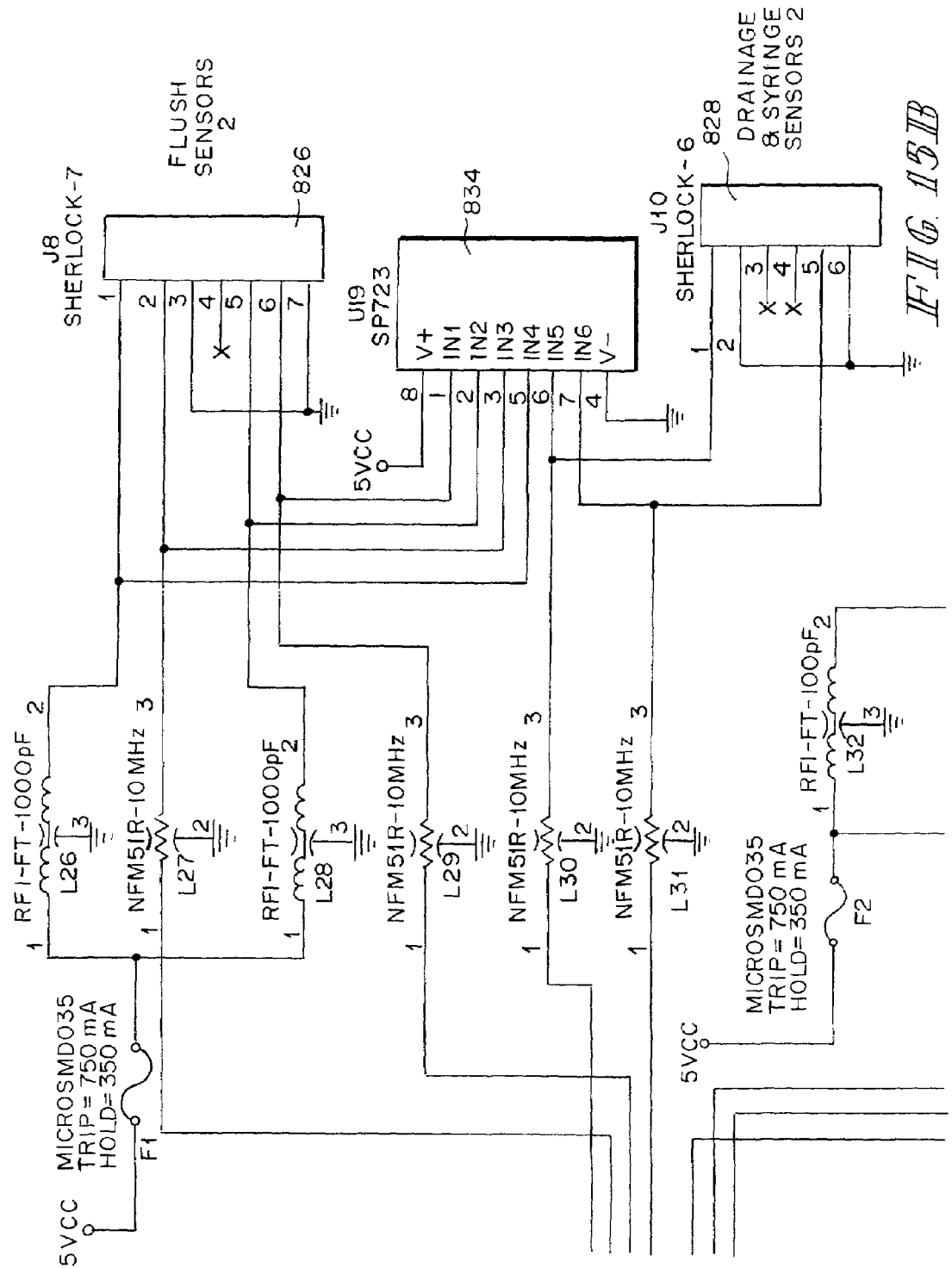
Figure 15C:
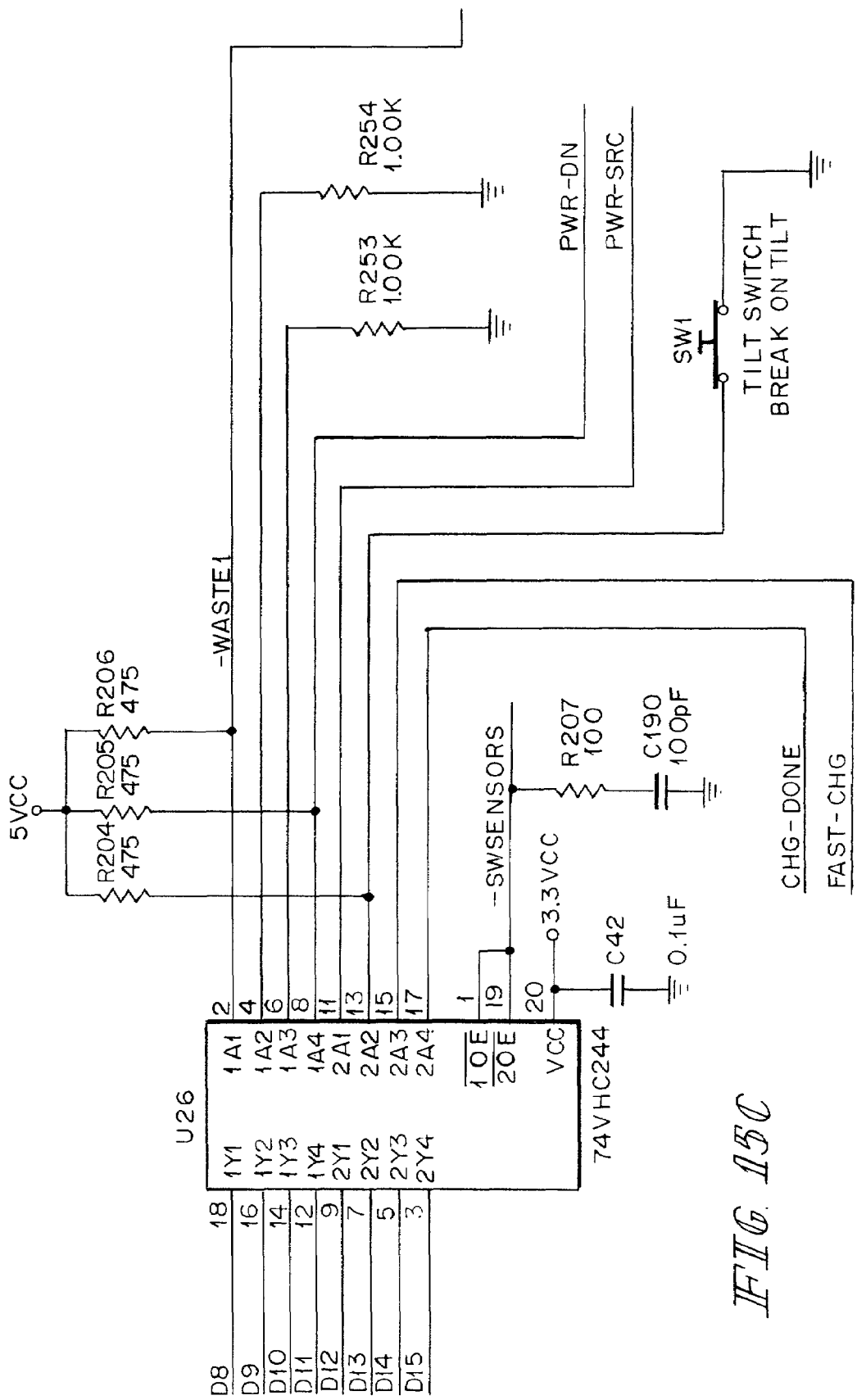
Figure 15D:
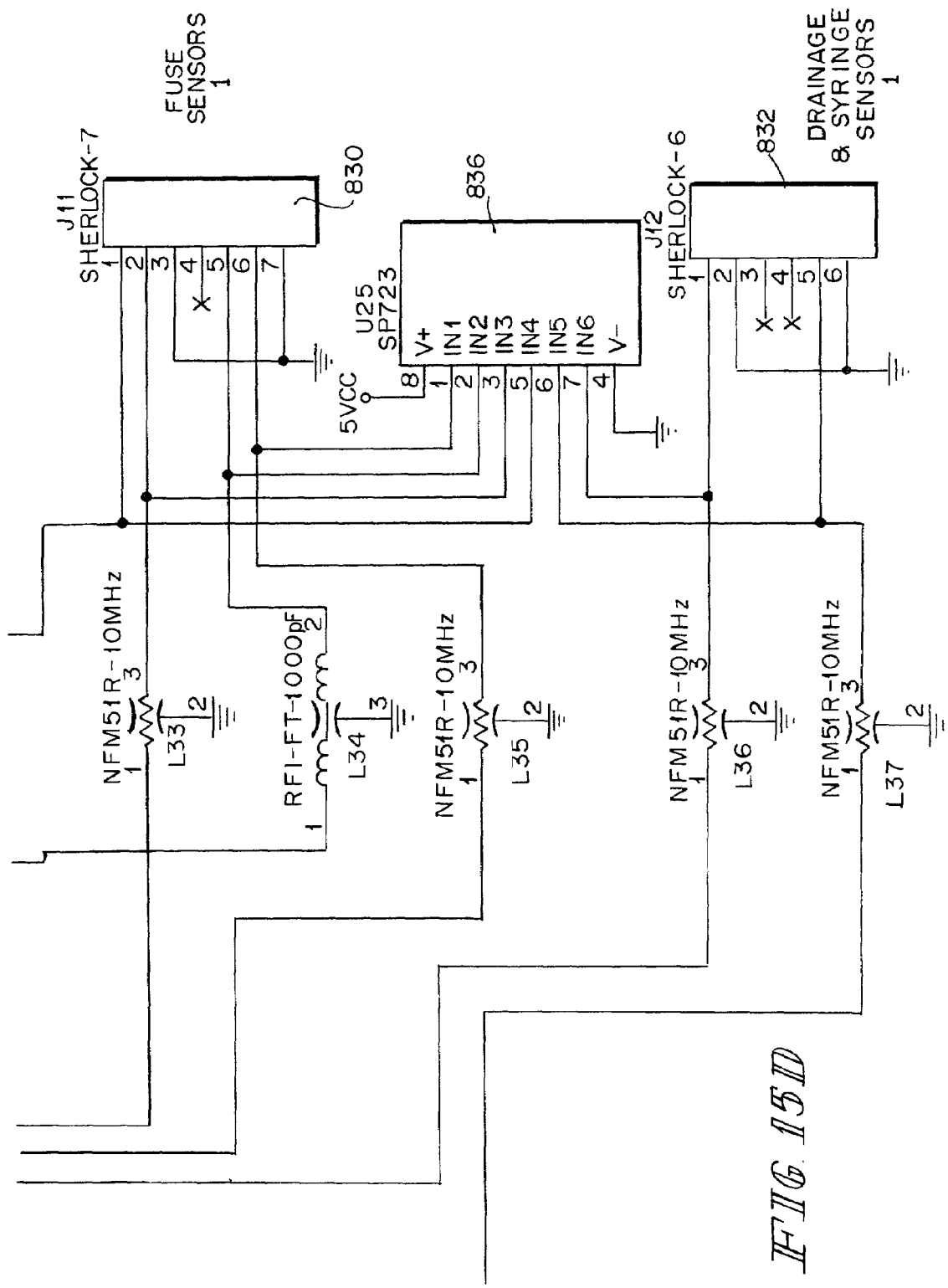

Referring now to FIG. 14, the battery charging system also includes a battery charge monitor 794, for example a Unitrode BQ2014 Gas Gauge IC with External Charge Control. The SEG2/PROG2, SEG3/PROG3, SEG4/PROG4, and SEG5/PROG5 terminals of monitor 794 are each coupled to ground through respective 100 Kohm resistors. The DONE terminal of monitor 794 is coupled to the system DONE line and to ground through a 200 Kohm resistor. The ground terminal, VSS, of monitor 794 is coupled to ground. The VSS terminal of monitor 794 is also coupled to the supply terminal, VCC, of monitor 794 through a capacitance of about 1.1 μF. A 10 Kohm resistor is coupled across the VCC and DISCTL terminals of monitor 794.

The VCC terminal of monitor 794 is also coupled to the cathode of a 5.1 volt zener diode and to the system BATT+ line through a 10 Kohm resistor. The cathode of this 5.1 zener diode is coupled to ground. The DisplayInputOutput terminal of monitor 794 is coupled to the anode of a first rectifier diode and the cathode of a second rectifier diode. The cathode of this first rectifier diode is coupled to the system BATT+ line. The anode of the second rectifier diode is coupled to ground. The DIO terminal of monitor 794 is also coupled to the system BP-DQ line through a 1 Kohm resistor. The system BP-DQ is further coupled to the system PPIC-VDD line through a 100 Kohm resistor.

The BATTerySENSe terminal of monitor 794 is coupled to the system BATT+ line through a 681 Kohm resistor and to ground through a parallel combination of a 0.1 μF capacitor and a 66.5 Kohm resistor. The SENSE terminal of monitor 794 is coupled to ground through a 0.1 μF capacitor and to the system BATT-SENSE line through a 100 Kohm resistor.

Referring now to FIGS. 15A–15D, the data bus lines D0–D7 are coupled to the output terminals, 1Y1-1Y4 and 2Y1-2Y4, respectively, of an octal 3-state buffer 820, for example a Fairchild 74VHC244 Octal Buffer/Line Driver with 3-STATE Outputs. The not1OutputEnable and not2OutputEnable terminals of buffer 820 are coupled to the system notSWSENSORS line. The supply voltage terminal, VCC, is coupled to the system 3.3VCC line and to the ground through a 0.1 μF capacitor. The input terminals, 1A1-1A4, of buffer 820 are coupled to the system notSYRINGE2, notHOME2, notEND2, and notWASTE2, respectively. The input terminals, 2A2-2A4, of buffer 820 are coupled to the system notSYRINGE1, notHOME1, and notEND1 lines, respectively. The input terminals of buffer 820, 1A1-1A4 and 2A1-2A4, are each coupled to the system 5VCC line through respective 475 ohm resistors.

The data bus lines D8–D15 are coupled to the output terminals, 1Y1-1Y4 and 2Y1-2Y4, respectively, of an octal 3-state buffer 822, for example a Fairchild 74VHC244 Octal Buffer/Line Driver with 3-STATE Outputs. The not1OutputEnable and not2OutputEnable terminals of buffer 822 are coupled to the system notSWSENSORS line and to ground through an R-C series network consisting of a 100 ohm resistor and a 100 pF capacitor. The supply voltage terminal, VCC, is coupled to the system 3.3VCC line and to the ground through a 0.1 μF capacitor.

The input terminals 1A1, 1A4, 2A1, 2A3, and 2A4 of buffer 822 are coupled to the system notWASTE1, PWR-ON, PWR-SRC, FAST-CHG, and CHG-DONE lines, respectively. The input terminals 1A2 and 1A3 of buffer 822 are coupled to ground through respective 1.0 Kohm resistors. The input terminal 2A2 of buffer 822 is also coupled to ground through a tilt switch. Input terminals 1A1, 1A4, and 2A2 are each coupled to the system 5VCC line through respective 475 ohm resistors.

The system notHOME2 and notEND2 lines are coupled through respective 10 MHz filters of a filter array 824 to pins 2 and 6 of flush sensor connector 826, respectively. Pins 2 and 6 of connector 826 are coupled to the INput3 and INput1 terminals, respectively, of an electronic protection array 834, illustratively a Harris SP723 Electronic Protection Array For ESD And Over-Voltage Protection. The system notSYRINGE2 and notWASTE2 lines are coupled through respective 10 MHz filters of filter array 824 to pin 1 and pin 5, respectively, of a drainage and syringe sensor connector 828. Pins 1 and 5 of connector 828 are coupled to the INput5 and INput6 terminals, respectively, of protection array 834.

The system notHOME1 and notEND1 lines are coupled through respective 10 MHz filters of filter array 824 to pins 2 and 6 of a flush sensor connector 830. Pins 2 and 6 of connector 830 are coupled to the INput3 and INput1 terminals, respectively, of an electronic protection array 836, illustratively a Harris SP723 Electronic Protection Array For ESD And Over-Voltage Protection. The system notSYRINGE1 and notWASTE1 lines are coupled through respecitve 10 MHz filters of filter array 824 to pin 1 and pin 5, respectively, of a drainage and syringe sensor connector 832. Pins 1 and 5 of connector 832 are coupled to the INput6 and INput5 terminals, respectively, of protection array 836.

The INput4 terminals of protection arrays 834, 836 are coupled to pin 1 of connectors 826, 830, respectively, and to the system 5VCC through respective 1,000 pF filters of filter array 824. The voltage supply pins, V+, and ground pins, V−, of protection arrays 834,836 are coupled to the system 5VCC line and ground, respectively. Pins 3 and 7 of connectors 826, 830 are coupled to ground. Pins 5 of connectors 826, 830 are coupled to INput2 terminals of protection arrays 834, 836, respectively, and to the 5VCC line through respective 1,000 pF filters of filter array 824. Pins 2 and 6 of connectors 828, 832 are coupled to ground.

Figure 16:
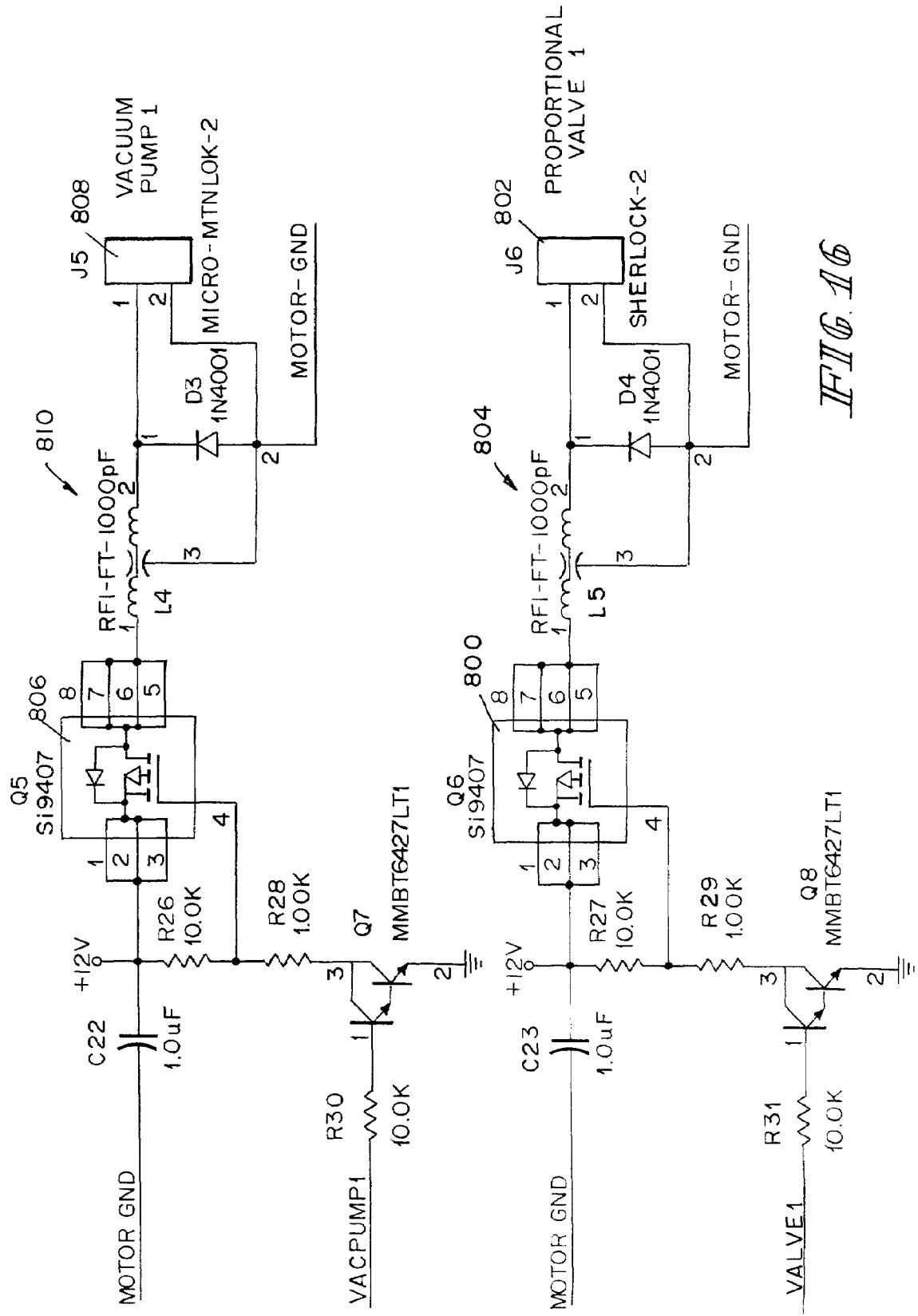

Turning now to FIG. 16, systems 14, 16 each include respective proportional valves and vacuum pumps. Only one valve connector circuit and one vacuum pump connector circuit will be described, with the understanding that others of these are substantially identical except where noted otherwise. The system MOTOR-GND line is coupled, through a 1.0 μF capacitor, to the system +12V line, the source terminal of a p-channel enhancement mode MOSFET 800, iullustratively a TEMIC SI9407 P-Channel Enhancement Mode MOSFET, and the gate of MOSFET 800 through a 10.0 Kohm resistor. The system VALVE1 line is coupled to the base of a Darlingtion transistor through a 10.0 Kohm resistor. The collector terminal of this Darlington transistor is coupled to the gate of MOSFET 800 through a 1 Kohm resistor and the emitter terminal is coupled to ground. The drain of MOSFET 800 is coupled to pin 1 of a proportional valve connector 802 through a 1,000 pF filter 804. The system MOTOR-GND line is coupled to pin 2 of connector 802 and to the anode of a rectifier diode. The cathode of this rectifier diode is coupled to pin 1 connector 802. The MOTOR-GND line is also coupled to filter 804

The system MOTOR-GND line is coupled, through a 1.0 μF capacitor, to the system +12V line, the source terminal of a p-channel Enhancement mode MOSFET 806, illustratively a TEMIC SI9407 P-Channel Enhancement Mode MOSFET, and the gate of MOSFET 806 through a 10.0 Kohm resistor. The system VACPUMP1 line is coupled to the base of a Darlingtion transistor through a 10.0 Kohm resistor as shown in FIG. 16. The collector terminal of this Darlington transistor is coupled to the gate of MOSFET 806 through a 1 Kohm resistor and the emitter terminal is coupled to ground. The drain of MOSFET 806 is coupled to pin 1 of vacuum pump connector 808 through a 1,000 pF capacitor filter 810. The system MOTOR-GND line is coupled to pin 2 of connector 808 and to the anode of a rectifier diode. The cathode of this rectifier diode is coupled to pin 1 of connector 808. The MOTOR-GND line is also coupled to filter 810.

Figure 17:
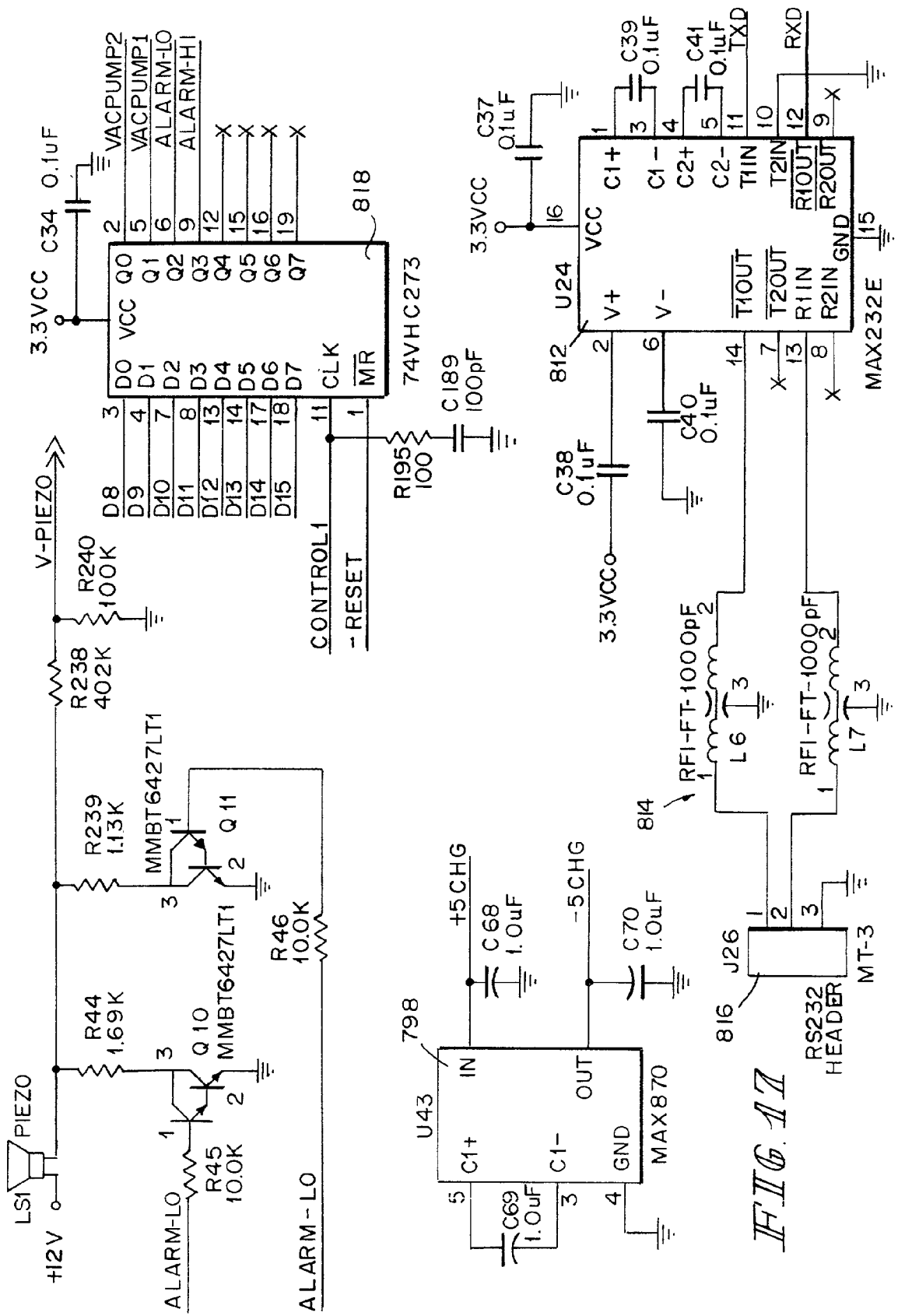

Referring now to FIG. 17, the system +5CHG line is coupled to ground through a 1.0 μF capacitor and to the INput terminal of a voltage inverter 798, illustratively a MAXIM MAX870 Switched-Capacitor Voltage Inverter. The OUTput terminal of inverter 798 is coupled to ground through a 1.0 μF capacitor and to the system −5CHG line. The internal oscillator Capacitor1 and Capacitor2 terminals of inverter 798 are coupled together through a 1.0 μF capacitor. The GrouND terminal of inverter 798 is coupled to ground.

The system TXD line is coupled to the Transmitter1-INput terminal of a RS-232 transceiver 812, illustratively a MAXIM MAX232E +5V RS-232 Transceiver as shown in FIG. 17. The system RXD line is coupled to the Reciever1OUTput of transceiver 812. The Transmitter2-INput and GrouND terminals of transceiver 812 are coupled to ground. The positive charge pump Capacitor1+ and Capacitor1− terminals of transceiver 812 are coupled together through a 0.1 μF capacitor. The negative charge pump Capacitor2+ and Capacitor2− terminals of transceiver 812 are coupled together through a 0.1 μF capacitor. The supply voltage terminal, VCC, of transceiver 812 is coupled to the system 3.3VCC line and to ground through a 0.1 μF capacitor. The charge pump voltage terminals, V+ and V−, are coupled to the system 3.3VCC line and ground, respectively, through respective 0.1 μF capacitors. The Transmitter1-OUTput and Receiver1OUTput terminals of transceiver 812 are coupled to pins 1 and 2, respectively, of connector 816 through respective 1,000 pF filters of a filter array 814. Pin 3 of connector 816 is coupled to ground.

The system data bus lines D8–D15 are coupled to the Data0–Data7 input terminals, respectively, of an octal D-type flip-flop 818, illustratively a Fairchild 74VHC273 Octal D-Type Flip-Flop as shown in FIG. 17. The data output terminals, Q0–Q3, of flip-flop 818 are coupled to the system VACPUMP2, VACPUMP1, ALARM-LO, and ALARM-HI lines, respectively. The supply voltage terminal, VCC, of flip-flop 818 is coupled to the system 3.3VCC line and to ground through a 0.1 μF capacitor. The notMasterReset and CLocK terminals of flip-flop 818 are coupled to the system CONTROL1 and notRESET lines, respectively. The CLK terminal of flip-flop 818 is also coupled to ground through an R-C series network consisting of a 100 ohm resistor and a 100 pF capacitor.

The system V-PIEZO line is coupled to ground through a 100 Kohm resistor and to the A terminal of a PIEZO horn through a 402 Kohm resistor as shown in FIG. 17. The B terminal of the PIEZO horn is coupled to the system +12V line. The A terminal of the PIEZO horn is also coupled to the collector of a first and a second Darlington transistor through a 1.69 Kohm resistor and a 1.13 Kohm resistor, respectively. The emitters of the first and second Darlington transistors are coupled to ground. The bases of the first and second Darlington transistors are coupled to the system ALARM-LO and ALARM-HI lines, respectively, through respective 10 Kohm resistors.

Although a vacuum wound therapy device and a method of providing vacuum wound therapy to a wound have been described in detail with reference to a certain preferred embodiment, variations and modifications of the device and method are within the scope and spirit of the invention as described and defined in the following claims.

The invention claimed is:

1. A vacuum wound therapy device for providing a negative pressure at a wound bed, the vacuum wound therapy device comprising:
 a vacuum bandage configured to fluidly communicate with the wound bed,
 a vacuum source fluidly coupled to the vacuum bandage to provide negative pressure for presentation at the wound bed, and
 a controller controlling the time rate of change of negative pressure presented at the wound bed to be less than a predetermined maximum allowable rate.

2. The device of claim 1 and further comprising an electrically actuated valve electrically coupled to the controller and fluidly coupled between the vacuum source and the vacuum bandage.

3. The device of claim 2 wherein the controller generates a modulated signal.

4. The device of claim 2 and further comprising a pressure transducer in fluid communication with the wound bed and electrically coupled to the controller.

5. The device of claim 1:
 wherein the controller implements a proportional, integral derivative (PID) control algorithm.

6. The vacuum wound therapy device of claim 1, wherein the controller comprises:
 a regulator configured to regulate the negative pressure provided at the wound bed by the vacuum bandage and vacuum source in response to a pressure regulation signal,
 a pressure transducer positioned to detect the negative pressure at the wound bed and provide a pressure signal indicative of the negative pressure at the wound bed,
 setpoint circuitry configured to provide a setpoint signal indicative of a desired negative pressure at the wound bed, and
 control circuitry electrically coupled to the pressure transducer, the setpoint circuitry and the regulator,
 the control circuitry being configured to generate the pressure regulation signal in response to the pressure signal and setpoint signal to limit the time rate of change of negative pressure at the wound bed while adjusting the negative pressure at the wound bed to the desired negative pressure.

7. The vacuum wound therapy device of claim 6 wherein the setpoint circuitry is manually adjustable by a caregiver.

8. The vacuum wound therapy device of claim 6 wherein the regulator comprises an electrically actuated valve fluidly coupled to the bandage and the vacuum source and electrically coupled to the control circuitry.

9. The device of claim 4, wherein the pressure transducer in fluid communication with the wound bed and electrically coupled to the controller is positioned in the fluid path between the vacuum source and the wound bed.

10. The device of claim 9, further comprising a vacuum canister,
 wherein the vacuum canister is positioned in the fluid path between the wound bed and the pressure transducer.

11. A vacuum wound therapy device for providing a negative pressure at a wound bed, the vacuum wound therapy device comprising:
 a vacuum bandage configured to fluidly communicate with the wound bed,
 a vacuum source fluidly coupled to the vacuum bandage to provide negative pressure for presentation at the wound bed,
 a controller controlling the rate of change of negative pressure presented at the wound bed,
 an electrically actuated valve electrically coupled to the controller and fluidly coupled between the vacuum source and the vacuum bandage, and
 a pressure transducer in fluid communication with the wound bed and electrically coupled to the controller,
 wherein the controller implements a proportional, integral derivative (PID) control algorithm and a filter to limit the control signal generated by the PID control algorithm within bounds.

12. A controller for regulating a negative pressure provided to a wound bed of a patient through a vacuum bandage fluidly coupled to a vacuum source, the controller comprising:
 a regulator configured to regulate the negative pressure provided at the wound bed by the vacuum bandage and vacuum source in response to a pressure regulation signal,
 a pressure transducer positioned to detect the negative pressure at the wound bed and provide a pressure signal indicative of the negative pressure at the wound bed,
 setpoint circuitry configured to provide a setpoint signal indicative of a desired negative pressure at the wound bed, and control circuitry electrically coupled to the pressure transducer, the setpoint circuitry and the regulator, whereby the control circuitry generates the pressure regulation signal in response to the pressure signal and setpoint signal to limit the time rate of change of negative pressure to a predetermined maximum allowable rate at the wound bed while adjusting the negative pressure at the wound bed to the desired negative pressure, wherein the regulator comprises an electrically actuated valve fluidly coupled to the bandage and the vacuum source and electrically coupled to the control circuitry, and wherein the valve is a proportional yalve.

13. The controller of claim 12 wherein the control circuitry generates a modulated signal to control the valve.

14. The regulator of claim 12, wherein the proportional valve is actuated by the control circuitry to a number of positions between a fully opened position and a fully closed position.

15. A method of providing vacuum wound therapy to a wound bed comprising the steps of providing a vacuum bandage in fluid communication with the wound bed, adjusting the air pressure at the wound bed through the vacuum bandage, and controlling the time rate of change of the air pressure at the wound bed to be less than a predetermined maximum allowable rate.

16. The method of claim 15 further comprising the step of measuring the air pressure at the wound bed.

17. The method of claim 16 further comprising the step of providing a desired air pressure at the wound bed and wherein the controlling step includes adjusting the air pressure at the wound bed until the measured air pressure approximates the desired air pressure.

18. A method for applying a vacuum to a space above an open wound bed, thereby to enhance the rate of healing of the wound, the method comprising:

establishing a predetermined vacuum pressure level to be achieved in the space, applying a suction from a vacuum source to the space, the suction being applied through a proportional valve, and controlling the proportional valve in incremental steps to increase the vacuum up to the predetermined pressure.

19. The method of applying a vacuum of claim 18, wherein application of the suction from a vacuum source to the space is further applied through a vacuum canister positioned between the wound bed and the vacuum source 20. The method of applying a vacuum of claim 19, further comprising the step of monitoring of the vacuum pressure through pressure sensor positioned between the vacuum source and the vacuum canister.

* * * * *